US007105678B2

(12) United States Patent
Meltzer et al.

(10) Patent No.: US 7,105,678 B2
(45) Date of Patent: Sep. 12, 2006

(54) BOAT TROPANES

(75) Inventors: Peter C. Meltzer, Lexington, MA (US); Paul Blundell, Somerville, MA (US); Bertha C. Madras, Newton, MA (US)

(73) Assignees: Organix, Inc., Woburn, MA (US); President and Fellows of Harvard College, Cambridge, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 09/975,586

(22) Filed: Oct. 11, 2001

(65) Prior Publication Data

US 2002/0131931 A1  Sep. 19, 2002

Related U.S. Application Data

(60) Continuation-in-part of application No. 09/875,523, filed on Jun. 6, 2001, which is a continuation of application No. 09/671,534, filed on Sep. 27, 2000, which is a continuation of application No. 09/568,106, filed on May 10, 2000, now Pat. No. 6,548,041, which is a division of application No. 09/314,441, filed on May 19, 1999, now Pat. No. 6,353,105, which is a division of application No. 08/893,921, filed on Jul. 11, 1997, now Pat. No. 5,948,933, and a continuation-in-part of application No. 08/552,584, filed on Sep. 3, 1995, now Pat. No. 6,171,576.

(60) Provisional application No. 60/133,761, filed on May 12, 1999.

(51) Int. Cl.
 C07D 451/02 (2006.01)
 C07D 451/00 (2006.01)
(52) U.S. Cl. ...................... 546/132; 546/124; 546/112
(58) Field of Classification Search ................ 546/132, 546/124, 112
 See application file for complete search history.

(56) References Cited

U.S. PATENT DOCUMENTS

| 3,813,404 | A | * | 5/1974 | Clarke et al. ............... 546/132 |
| 4,434,151 | A | | 2/1984 | Byrne et al. ................. 424/1.1 |
| 4,673,562 | A | | 6/1987 | Davison et al. .............. 424/1.1 |
| 4,746,505 | A | | 5/1988 | Jones et al. .................. 424/1.1 |
| 5,122,361 | A | | 6/1992 | Kung et al. .................. 424/1.1 |
| 5,128,118 | A | | 7/1992 | Carroll et al. ................ 424/1.1 |
| 5,310,912 | A | | 5/1994 | Neumeyer et al. .......... 546/132 |
| 5,334,728 | A | | 8/1994 | Kung et al. .................. 548/402 |
| 5,380,848 | A | | 1/1995 | Kuhar et al. ................. 546/124 |
| 5,413,779 | A | | 5/1995 | Kuhar et al. ................. 424/1.85 |
| 5,426,189 | A | | 6/1995 | Kung et al. .................. 548/402 |
| 5,439,666 | A | | 8/1995 | Neumeyer et al. .......... 424/1.85 |
| 5,493,026 | A | | 2/1996 | Elmaleh et al. ............. 346/132 |
| 5,496,953 | A | * | 3/1996 | Kuhar et al. ................. 546/125 |
| 5,760,055 | A | * | 6/1998 | Davies ......................... 514/304 |
| 5,980,860 | A | | 11/1999 | Kung et al. .................. 424/1.65 |
| 6,008,227 | A | * | 12/1999 | Davies et al. ............... 514/304 |
| 6,350,758 | B1 | | 2/2002 | Kozikowski et al. ........ 514/304 |
| 6,358,492 | B1 | * | 3/2002 | Kuhar et al. ................ 424/1.85 |

FOREIGN PATENT DOCUMENTS

| EP | 0 135 160 | 5/1985 |
| WO | WO 93/09814 | 5/1993 |
| WO | WO 94/26274 | 11/1994 |
| WO | WO 95/11901 | 5/1995 |
| WO | WO 97/14445 | 4/1997 |
| WO | WO 97 16210 A | 5/1997 |
| WO | WO 97 47328 A | 12/1997 |
| WO | WO 98/24788 | 11/1998 |

OTHER PUBLICATIONS

Cesati R R III et al; "Synthesis of cyclopentadienyl tricarbonyl technetium phenyl-tropane derivatives by direct double ligand transfer with ferrocene precursors." Journal of Labelled Compounds and Radiopharmaceuticals; vol. 42; Suppl. 1, Jun. 1999; pp. S150-S152.

Fang P et al; "Radiopharmacology study of 99mTc-TRODAT-1 as a dopamine transporters imaging agent." Journal of Labelled Compounds and Radiopharmaceuticals; vol. 42; Suppl. 1, Jun. 1999, pp. S336-S338.

Hoepping, A. et al; "11. Improved synthesis and biological evaluation of [99mTc] technepine and comparison with a modified technepine containing a hexyl linker (hexyltecnepine)" Forschungszent. Rossendorf, 'BER.! FZR, 1997; vol. FZR-200; pp. 33-36.

Hoepping A. et al; "Novel rhenium complexes derived from alpha-tropanol as potential ligands for the dopamine transporter." Bioorganic & Medicinal Chemistry; vol. 6; No. 10, pp. 1663-1672, 1998.

Hoepping A et al; "Retropane—a new Rhenium Complex as a potential Ligand to label the Dopamine Transporter" Bioorganic & Medicinal Chemistry Letters, vol. 6; No. 23, Dec. 3, 1996, pp. 2871-2874.

(Continued)

Primary Examiner—Charanjit S. Aulakh
(74) Attorney, Agent, or Firm—Edwards Angell Palmer & Dodge LLP; George Neuner; Mark D. Russett

(57) ABSTRACT

Radiopharmaceutical compounds are disclosed. A tropane compound is linked through the N atom at the 8-position to a chelating ligand capable of complexing technetium or rhenium to produce a neutral labeled complex that selectively binds to the dopamine transporter over the serotonin transporter with a ratio of 10 or more. These compounds can be prepared as separate diastereoisomers as well as a mixture of diastereoisomers. Also disclosed are radiopharmaceutical kits for preparing the labeled radiopharmaceutical compounds.

12 Claims, 14 Drawing Sheets

OTHER PUBLICATIONS

Hoepping A. et al; "TROTEC-1; A new high-affinity ligand for labeling of the dopamine transporter"; Journal of Medicinal Chemistry, Nov. 5, 1998, vol. 41; No. 23, pp. 4429-4432.

Madras et al; "Technepine: a high-affinity 99Technetium probe to label the dopamine transporter in brain by SPECT imaging" Synapse, vol. 22; No. 3; Mar. 1996, pp. 239-246.

Meegalla, Sanath K. et al; "Synthesis and Charactrerization of Technetium-99m-Labeled Tropanes as Dopamine Transporter-Imaging Agents"; J. Med. chem., 1997, vol. 40; No. 1, pp. 9-17.

Meltzer PC et al; "A technetium-99m SPECT imaging agent which targets the dopamine transporter in primate brain." Journal of Medicinal Chemistry; Jun. 6, 1997, vol. 40; No. 12, pp. 1835-1844.

Meltzer PC et al; "Substituted 3-Phenyltropane Analogs of Cocaine: Synthesis, Inhibition of Binding at Cocaine Recognition Sites, and Positron Emission Tomography Imaging"; Journal of Medicinal Chemistry; vol. 36; 1993, pp. 855-862.

Meltzer et al; "Structure-activity-relationships of Inhibition of the Dopamine Transporter by 3-Arylbicyclo [3.2.1] octanes"; Medicinal Chemistry Research, vol. 8; No. 1/2, 1998, pp. 12-34.

S. Meegalla, et al.; "First Example of a $^{99m}$Tc Complex as a Dopamine Transporter Imaging Agent"; J. Am. Chem. Soc.; 1995; pp. 11037-11038.

S. Meegalla, et al.; "Tc-99m-Labeled Tropanes as Dopamine Transporter Imaging Agents"; Bioconjugate Chem.l, 1996 pp. 421-429.

Brandau, et al., *Nucl. Med. Biol.* 21, No. 8, pp. 1073-1081. (1994).

Bryson, et al., *Inorg. Chem.* 1988, 27, pp. 2154-2161.

Davison, A., et al., *Inorg. Chem.* 1981, vol. 20, No. 6, pp. 1629-1632.

DiZio, J. P., et al., *Bioconj. Chem.* 1991, 2, pp. 353-366.

DiZio, J.P., et al., *J. Nucl. Med.* 1992, vol. 33, No. 4, pp. 558-569.

Fritzberg et al., *J. Nucl. Med.* 1981, vol. 22, No. 3, pp. 258-263.

Fritzberg et al., *J. Nucl. Med.* 1982, vol. 23, No. 7, pp. 592-598.

Gustavson, L.M., et al., *Tet. Lett.* 1991, 32, pp. 5484-5488.

Hansen, et al., *J. Nucl. Med.* 1994, vol. 35, No. 7, pp. 1198-1205.

Jones, et al., *J. Nucl. Med.* 1982, vol. 23, No. 9, pp. 801-809.

Steignman, et al., *The Chemistry of Technetium in Medicine* 1992, pp. 117-127.

Archer, et al., *New Hydrophilic Ligands for $^{99m}$Tc-Based Radiopharmaceuticals, Technetium and Rhenium in Chemistry and Nuclear Medicine 4*, eds. M. Nicolini, G. Bandoli, U. Mazzi, Servizi Grafici Editoriali, Padua, 1995, pp. 177-179.

Baldwin, et al., *Synthesis and Biodistribution of $^{99m}$Tc Aromatic Amine-Amide-Thiol-Thioether $N_2S_2$ Complexes, Technetium and Rhenium in Chemistry and Nuclear Medicine 4*, eds. M. Nicolini, G. Bandoli, U. Mazzi, Servizi Grafici Editoriali, Padua, 1995, pp. 329-332.

Kelly, et al., *Low Lipophilicity Technetium-99m Complexes for Radiopharmaceutical Applications, Technetium and Rhenium in Chemistry and Nuclear Medicine 4*, eds. M. Nicolinin, G. Bandoli, U. Mazzi, Servizi Grafici Editoriali, Padua, 1995, pp. 259-263.

Kung, H.F., et al., *New TcO (III) and ReO (III) $N_2S_2$ Complexes as Potential CNS 5-$HT_{1A}$ Receptor Imaging Agents, Technitium and Rhenium in Chemistry and Nuclear Medicine 4*, eds. M. Nicolini, G. Bandoli, U. Mazzi, Servizi Grafici Editoriali, Padua, 1995, pp. 293-298.

Liu, et al., *New $N_zS_2$ Diamidedithiol and $N_3S$ Triamidethiols as Bifunctional Chelating Agents for Labelling Small Peptides with Technetium-99m, Technetium and Rhenium in Chemistry and Nuclear Medicine 4*, eds. M. Nicolini, G. Bandoli, U. Mazzi, Servizi Grafici Editoriali, Padua, 1995, pp. 383-393.

Mahmood, et al., *Technetium and Rhenium Complexes of Amine Amide Dithiol Ligands: Ligand Synthesis and Metal Complexes, Technetium and Rhenium in Chemistry and Nuclear medicine 4*, eds. M. Nicolini, G. Bandoli, U. Mazzi, Servizi Grafici Editoriali, Padua, 1995, pp. 211-215.

Volkert, W.A., *Ligand System Useful in Designing High Specific Activity $^{99m}$Tc or $^{186/188}$Re Radiopharmaceuticals, Technetium and Rhenium in Chemistry and Nuclear Medicine 4*, eds. M. Nicolini, G. Bandoli, U. Mazzi, Servizi Grafici Editoriali, Padua, 1995, pp. 17-26.

Davies et al., (1994), *J. Med. Chem.* vol. 37, pp. 1262-1268, "Synthesis of α-acyl-3B-aryl-8-azgbicyclo [3.2.1] octanes and their binding affinities at Dopamine and Serotonin transport sites in rat striatum and frontal cortex".

Bennett et al (Mar. 1995) *The Journal of Pharmacology and Experimental Theraupeutics*, vol. 272, No. 3. pp. 1176-1186. "Novel 2-substituted cocaine analogs: uptake and Ligand Binding studies at depainine, serotonin, and norepinephrine transport sites in the rat brain.".

T.N. Rao, et al., *Monoamide Monoamine Dithiolate Ligands (MAMA) As Chelating Agents for Technetium: Kinetic And Mechanistic Studies of Complex Formation*, in Eight International Symposium on Radiopharmaceutical Chemistry, 1990, pp. 39-40.

H. Spies, et al., *Technetium And Rhenium Complexes As Potential Receptor Biding Ligands*, Abstract in Eleventh International Symposium on Radiopharmaceutical Chemistry, 1995, pp. 319-320.

P.D. Mozley, et al., Abstract No. 123, in *The Journal of Nuclear Medicine, IPT Spect Imaging in Healthy Volunteers: Evaluating Changesin the Dopamine Reuptake Transporter With Normal Againg*, vol. 36, No. 5, May 1995, pp. 32P.

A.M. Myers, et al., Abstract No. 505, in *The Journal of Nuclear Medicine, Metabolite Analysis of I-123 IPT: a New Dopamine Reuptake Site Imaging Agent*, vol. 36, No. 5, May 1995, pp. 124P.

A.J. Kim, et al., Abstract No. 511, in *The Journal of Nuclear Medicine In Vivo Quantification of Presynaptic Dopamine Transporter Binding Parameters in Human Brains with [I-123]IPT Spect.*, vol. 36, No. 5, May 1995, pp. 125P.

A.J. Kim, et al., Abstract No. 808, in *The Journal of Nuclear Medicine, Absolute Activity Measurements of in Vivo Monkey Brain Using a Triple Headed Spect and a New Radioligand: [I-123] IPT.*, vol. 36, No. 5, May 1995, pp. 178P-179P.

P.D. Mozley, et al., Abstrct No. 826, in *The Journal of Nuclear Medicine, The Dosimetry of [I-123] IPT: a Cocaine Analog for Imaging the Dopamine Reuptake Transporter.*, vol. 36, No. 5, May 1995, pp. 183P.

Meegalla et al., [Nov. 1995] *J. Am. Chem. Soc.*, vol. 117, No. 44, pp. 11037-11038, "First Example of a 99m-Tc Comples as a Dopamine Transporter Imaging Agent."

Meegalla et al., [1996] , *Bioconjugate Chem.*, vol. 7, No. 4, pp. 421-429, "Tc-99m Labeled Tropanes as Dopamine Transporter Imaging Agnets.".

Clarke et al., *Compounds Affecting the Central Nervous System. 4. 3-Phenyltropane-2-carboxylic Esters and Analogs, Journal of Medicinal Chemistry*, 1973, vol. 16, No. 11, pp. 1260-1267.

Ohmomo et al., *New Conformationally Restricted $^{99m}$Tc $N_2S_2$ Complexes as Myocardial Perfusion Imaging Agents, J. Med. Chem.*, 1992, 35, pp. 157, 162.

Carroll et al., *Cocaine and 3-(4'-Substituted phenyl) tropane-2-carboxylic Acid Ester and Amide Analogues. New High-Affinity and Selective Compounds for the Dopamine Transporter, J. Med. Chem.*, 1995, 38, pp. 379-388.

Keverline, et al., "Synthesis o the 2β, 3α- and 2β, 3β-Isomers of 3-(p-Substituted phenyl)tropane-2-carboxylic Acid Methyd Esters," Tetrahedron Letters, 36:3099-3102 (1995).

Meltzer, et al., "2-Carbomethoxy-3-aryl-8-oxabicyclo[3.2.1]octanes: Potent Non-Nitrogen Inhibitors of Monoamine Transporters," Journal of Medical Chemistry, 40:2661-2673 (1997).

Holmquist, et al., "3α-(Substituted Phenyl) Tropane-2β-Carboxylic Acid Esters: Ligands with Unexpected High Affinity and Selectivity at the Dopamine Transporter," Americal Chemical Society (Abstract), 213: Abstract No. 191 (1997).

Holquist, et al., "3α-(4'-Substituted phenyl)tropane-2β-carboxylic Acid Methyl Esters: Novel Ligands with Affinity and Selectivety at the Dopamine Transporter," J. med. Chem., 39:4139-4141 (1996).

Meltzer, et al., "Bicyclo[3.2.1]Octanes: Synthesis and Inhibition of Binding at the Dopamine and Serotonin Transporters," Bioorganic and Medicinal Chemistry Letters 9:857-862 (1999).

Lieske, et al., "(-)-3β-Substituted Ecgonine Methyl Esters as Inhibitors for Cocaine Binding and Dopamine Uptake," J. Med. Chem. 41:864-876 (1998).

Copy of European Search Report dated Jan. 14, 2005.

* cited by examiner

BOAT TROPANES

CROSS-REFERENCE TO RELATED APPLICATIONS

This is a continuation application of application Ser. No. 09/568,106 filed May 10, 2000, now U.S. Pat. No. 6,548,041 which claims the benefit of provisional application 60/133,761 filed May 2, 1999, and is a continuation in part of application Ser. No. 09/875,523 filed Jun. 6, 2001, now U.S. Pat. No. 6,670,375, which is a continuation of application Ser. No. 09/671,534 filed Sep. 27, 2000, now U.S. Pat. No. 6,417,221, which is a division of Ser. No. 09/314,441 filed May 19, 1999, now U.S. Pat. No. 6,353,105, which is a division of Ser. No. 08/893,921 filed Jul. 11, 1997, now U.S. Pat. No. 5,948,933, and is a continuation in part of Ser. No. 08/552,584 filed Nov. 3, 1995, now U.S. Pat. No. 6,171,576.

STATEMENT OF GOVERNMENT SUPPORT

This invention was made with government support under Grant Numbers DA06303 and DA11558 awarded by the NIH/NIDA. The government has certain rights in the invention.

FIELD OF THE INVENTION

The present invention relates to coordination complexes comprising a radiolabeled ligand with high binding affinity and good selectivity for the dopamine transporter (DAT). Such agents can be useful for the early diagnosis and treatment of neurodegenerative disorders.

BACKGROUND OF THE INVENTION

The dopamine transporter (DAT) plays a critical role in physiological, pharmacological and pathological processes in brain. The transport system is a primary mechanism for terminating the effects of synaptic dopamine, thereby contributing to the maintenance of homeostasis in dopamine systems. It also appears to be a principal target of cocaine in the brain. (Kennedy and Hanbauer, *J. Neurochem.* 1983, 41, 172–178; Shoemaker et al., *Naunyn-Schmeideberg's Arch. Pharmacol.* 1985, 329, 227–235; Reith et al., *Biochem Pharmacol.* 1986, 35, 1123–1129; Ritz et al., *Science* 1987, 237, 1219–1223; Madras et al., *J. Pharmacol. Exp. Ther.* 1989a, 251, 131–141; Bergman et al., *J. Pharmacol. Exp. Ther.* 1989, 251, 150–155; Madras and Kaufman, *Synapse* 1994, 18, 261–275). Furthermore, the dopamine transporter may be a conduit for entry of neurotoxins into dopamine containing cells.

The striatum has the highest levels of dopamine terminals in the brain. A high density of DAT is localized on dopamine neurons in the striatum and appears to be a marker for a number of physiological and pathological states. For example, in Parkinson's disease, dopamine is severely reduced and the depletion of DAT in the striatum has been an indicator for Parkinson's disease (Schoemaker et al., *Naunyn-Schmeideberg's Arch. Pharmacol.* 1985, 329, 227–235; Kaufman and Madras, *Synapse* 1991, 9, 43–49). Consequently, early or presymptomatic diagnosis of Parkinson's disease can be achieved by the quantitative measurement of DAT depletion in the striatum. (Kaufman and Madras, *Synapse* 1991, 9, 43–49). Simple and noninvasive methods of monitoring the DAT are quite important. Depletion could be measured by a noninvasive means such as brain imaging using a scintillation camera system and a suitable imaging agent (Frost et al., *Ann. Neurology* 1993, 34, 423–431; Hantraye et al., *Neuroreport* 1992, 3, 265–268). Imaging of the dopamine transporter also would enable the monitoring of progression of the disease and of reversal of the disease such as with therapies consisting of implants of dopamine neurons or drugs that retard progression of the disease.

Other neuropsychiatric disorders, including Tourette's Syndrome and Lesch Nyhan Syndrome and possibly Rett's syndrome, are also marked by changes in DAT density. The DAT also is the target of the most widely used drug for attention deficit disorder, methylphenidate. The capacity to monitor the transporter in persons suffering from this disorder can have diagnostic and therapeutic implications. Furthermore, an age-related decline in dopamine neurons can be reflected by a decline in the dopamine transporter (Kaufman and Madras, *Brain Res.* 1993, 611, 322–328; van Dyck et al., *J. Nucl. Med.* 1995, 36, 1175–1181) and may provide a view on dopamine deficits that lie outside the realm of neuropsychiatric diseases.

The density of the DAT in the brains of substance abusers has also been shown to deviate from that in normal brain. For example, the density is elevated in post-mortem tissues of cocaine abusers (Little et al., *Brain Res.* 1993, 628, 17–25). On the other hand, the density of the DAT in chronic nonviolent alcohol abusers is decreased markedly. (Tiihonen et al., *Nature Medicine* 1995, 1, 654–657). Brain imaging of substance abusers can be useful for understanding the pathological processes of cocaine and alcohol abuse and monitoring restoration of normal brain function during treatment.

Accordingly, a radiopharmaceutical that binds to the DAT can provide important clinical information to assist in the diagnosis and treatment of these various disease states.

In order to be effective as an imaging agent for the disorders described above, it must have a specific binding affinity and selectivity for the transporter being targeted, e.g. DAT. Brain imaging agents must also have blood brain barrier (BBB) permeability. Yet, it has been difficult to produce a metal chelate which can cross the blood brain barrier while still retaining binding affinity and selectivity for its receptor site. Therefore, it is very desirable to find a suitable agent that satisfies these criteria and will complex with a desired radionuclide, such as $^{99m}$Tc.

In addition, to be an effective imaging agent, a specific target:nontarget ratio is necessary. In the case of an agent selective for DAT one must take into account the fact that the striatum, the region of the brain having the highest density of the dopamine transporter, also contains serotonin transporter (SET). The SET is normally present at one-tenth to one-fifteenth the concentration of the dopamine transporter. Imaging agents that bind very strongly to DAT sometimes also exhibit a degree of binding to SET. Although such a nontarget binding typically poses no serious problem in the imaging of normal brains due to the greater number of DAT compared to SET, under disease conditions in which DAT are selectively reduced (or in which SET may be selectively increased), binding to the SET may make it difficult to quantify DAT. Moreover, binding to SET in other brain regions such as the hypothalamus and thalamus can reduce striatal contrast and diminish accuracy in localizing and imaging the striatum. Therefore, the target to nontarget binding ratio of DAT:SET can be important. Presently, among the most effective compounds for viewing and quantifying the DAT are phenyltropane derivatives that are labelled with positron emitters, such as $^{11}$C and $^{18}$F, and gamma emitters, such as $^{123}$I.

The radionuclide, technetium-99m, $^{99m}$Tc ($T_{1/2}$ 6.9 h, 140 KeV gamma ray photon emission) is a preferred radionuclide for use in imaging because of its excellent physical decay properties and its chemistry. For example, its half-life of about 6 hours provides an excellent compromise between rate of decay and convenient time frame for an imaging study. Thus, it is much preferred to other radionuclides such as $^{123}$I, which has a substantially longer half life, or $^{18}$F, which has a substantially shorter half-life, and which are much more difficult to use. Its emission characteristics also make it easy to image. Further, it can be conveniently generated at the site of use. $^{99m}$Tc is currently the radionuclide of choice in diagnostic centers around the world. It would be desirable to have a coordination complex with technetium for imaging DAT. Such a complex could be used for detecting conditions in which the DAT is useful as a marker.

However, a number of difficulties arise in the use of technetium for radioimaging agents because of its chemistry. For example, $^{99m}$Tc must typically be bound by a chelating agent. Consequently it is much more difficult to design and prepare a $^{99m}$Tc radioligand than it is to prepare a radioligand using other radionuclides such as $^{123}$I, which can be attached covalently to the ligand. The size of the chelating agent for technetium also can create problems when using this radionuclide in imaging agents. This can be an especially difficult problem when attempting to design receptor-based imaging agents using Tc.

Imaging agents being tested to determine their ability as diagnostic tools for neurodegenerative diseases typically are $^{123}$I labeled radioiodinated molecules. See, for example, RTI-55 (Boja, J. W., et al., *Eur. J. Pharmacol.* 1991, 194, 133–134; Kaufman and Madras, *Synapse*, 1992, 12, 99–111) or β-CIT (Neumeyer, J. L., et al., *Med. Chem.* 1991, 34, 3144–3146) and an iodoallyltropane, altropane (Elmaleh, D. R., et al., U.S. Pat. No. 5,493,026.

Although the tropane family of compounds are known to bind to the dopamine transporter, the addition of bulky chelating ligands for binding technetium or rhenium would be expected to affect potency and ability to cross the blood brain barrier of the resulting labeled complex. Kung, et al., in *Technetium and Rhenium in Chemistry and Nuclear Medicine* 4, eds. M. Nicolini, G. Bandoli, U. Mazzi, Servizi Grafici Editoriali, Padua, 1995, report that a $^{99}$Tc-labelled $N_2S_2$ ligand complexed with an arylpiperazine known to have selective binding to serotonin$_{1A}$ had only moderate binding affinity in vitro and failed to penetrate the intact blood-brain barrier.

It would be desirable to have a technetium or rhenium radio-labelled DAT imaging agent which is capable of crossing the blood brain barrier and has a high binding affinity and selectivity for the DAT.

SUMMARY OF THE INVENTION

The present invention provides radiopharmaceutical compounds that form coordination complexes with a technetium or rhenium radionuclide and that selectively bind to dopamine transporters, thereby providing novel radio labeled agents. Preferred such agents include radioimaging agents which are capable of crossing the blood brain barrier to image DAT in the brain.

The compounds of the present invention comprise a tropane compound linked through the N atom at the 8-position to a chelating ligand capable of complexing a technetium or rhenium radionuclide to produce a neutral labeled complex that selectively binds to the dopamine transporter. These compounds can be prepared as separate diastereoisomers as well as a mixture of diastereoisomers.

Tropane compounds useful in the practice of the present invention bind to the dopamine transporter. Preferred radiopharmaceutical compounds of the invention can be represented by the following structural formula:

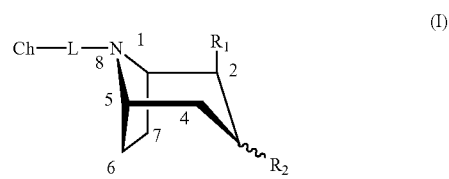

(I)

wherein $R_1$ is α or β and is selected from $COOR^a$, $COR^a$, and $CON(CH_3)OR^a$;

$R_2$ is α or β and is selected from $C_6H_4X$, $C_6H_3XY$, $C_{10}H_7X$, and $C_{10}H_6XY$;

$R^a$ is selected from $C_1$–$C_5$ alky, e.g. methyl, ethyl, propyl, isopropyl, etc.;

X and Y are independently selected from $R^a$, H, Br, Cl, I, F, OH, and $OCH_3$;

L is $—(CH_2)_n$ where n is an integer from 1 to 6, or $—(CH_2)_n$-(aryl, arylalkyl, ethenyl or ethynyl)-$(CH_2)_m$ where the sum of n plus m is an integer from 1 to 6; and Ch is a tridentate or tetradentate chelating ligand that forms a neutral complex with technetium or rhenium, and further wherein the bond between $C_2$ and $C_3$ is either a single bond or a double bond.

Thus, $R_1$ and $R_2$ can be in the α or β configuration. Further, $R_1$ preferably can be substituted at the $C_2$ or $C_4$ when the tropane has a 1R or 1S configuration, respectively. The chelating ligand, if chiral, can be syn or anti with R, S, or RS.

The imaging agents of the present invention are useful for detecting tropane recognition sites including neuronal transporters such as the dopamine transporter. For purposes of the present invention, a tropane recognition site is any receptor or transporter site that binds to the tropane compound. Thus, the compounds of this invention can be used as diagnostic agents, prognostic agents and therapeutic agents for neurodegenerative diseases.

The present invention also provides a method of using the coordination complex as an imaging agent for detecting neurodegenerative and neuropsychiatric disorders characterized by a change in density of DAT or dopamine neurons. For example, a method for detecting the change in DAT resulting from a neurodegenerative disease, such as Parkinson's disease, comprises injecting a labeled compound of the present invention in a dose effective amount for detecting DAT in the particular mammal and obtaining images of the labeled compound bound to DAT. Rhenium labeled compounds can also be useful for therapeutic treatments.

The present invention also provides kits for producing the compounds of the present invention labeled with technetium or rhenium. The kits typically comprise a sterile, non-pyrogenic container containing lyophilized compound and a reducing agent to form a complex of the compound with technetium or rhenium. The kits permit ready reconstitution and labeling with aqueous solutions containing the radionuclide, e.g. pertechnetate, preferably having a pH in the range of about 5 to about 8.

DETAILED DESCRIPTION OF THE INVENTION

Figure 1:
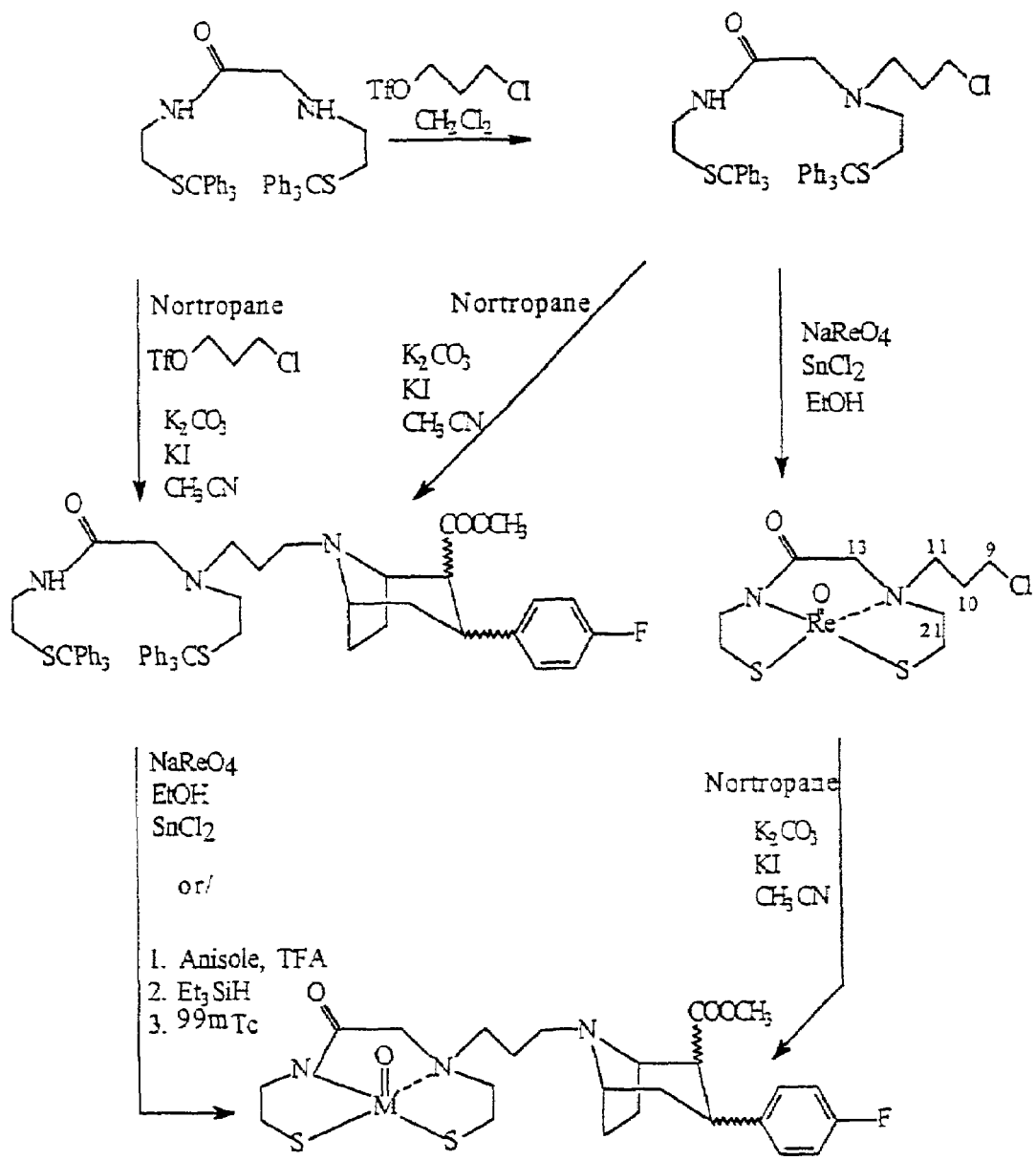
FIG. 1 is an illustration of alternative general reaction schemes for linking a $N_2S_2$ chelating ligand to a nortropane analog and labeling with a metal "M", which can be technetium or rhenium.

The compounds of the present invention comprise a tropane compound or ligand that selectively binds to tropane recognition sites, e.g., neuron transporters such as the DAT. The tropane ligand is radiolabeled with a radioactive technetium or rhenium by a chelating ligand which is attached to the tropane ligand by a linker. The unlabeled compounds of this invention are schematically represented by the formula Ch-L-Tr, wherein Ch is the chelating ligand, L is the linker and Tr is the tropane ligand.

Tropane compounds or ligands useful in the practice of the present invention can generally be represented by formula II where $R_1$ and $R_2$ are defined as above and where $R_1$ can also be substituted at the $C_4$ position of the tropane ring:

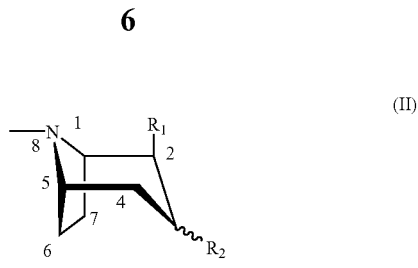

Any tropane compound of the general formula II is useful in the present invention so long as it binds to DAT. Examples of particularly useful tropanes are: 2-carbomethoxy-3-(4-fluorophenyl)-N-methyltropane ("WIN 35,428") (Clarke, R. L., et al., *J. Med. Chem.* 1973, 16, 1260–1267) which binds potently ($IC_{50}$=11.0 nM) and with specificity to the DAT (Meltzer, P. C., et al., *J. Med. Chem.* 1993, 36, 855–862); 2-carbomethoxy-3-(3,4-dichlorophenyl)-N-methyltropane ("O-401"; $IC_{50}$=1.09 nM) (Meltzer, P. C., et al., *J. Med. Chem.* 1993, 36, 855–862). Tropane analogs that have a 3α-group are of the boat configuration. Other tropanes having a 3β-oriented group are of the chair configuration.

Chelating ligands useful in the practice of the present invention comprise any tridentate or tetradentate ligand that binds technetium or rhenium to form a neutral complex. The chelating ligand is covalently attached to the linker L, as described below. Preferred chelating ligands contain a plurality of N or S atoms for complexing with the radionuclide.

Examples of suitable ligands are the $N_2S_2$ compounds represented by the following structural formulas:

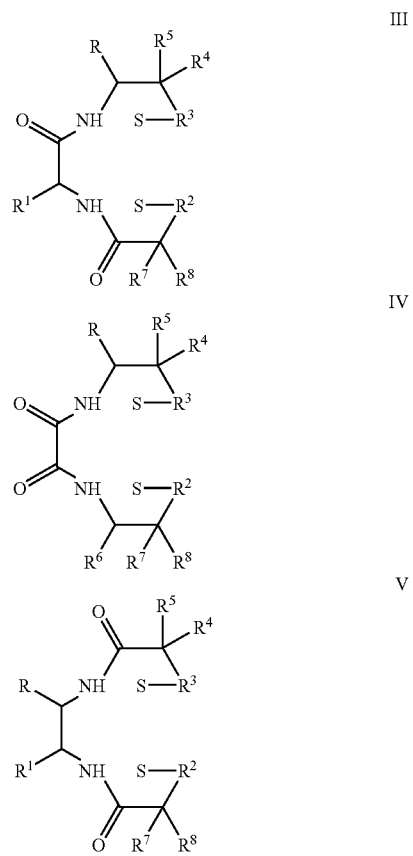

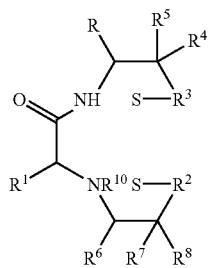

VI

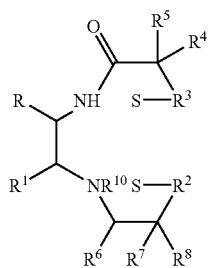

VII

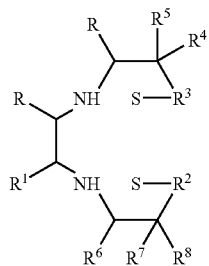

VIII wherein R, $R^6$, and $R^{10}$ are each selected from hydrogen, substituted or unsubstituted lower alkyl alkyl$R^9$, or —COR$^9$ where $R^9$ is selected from hydroxy, substituted lower alkoxy, substituted or unsubstituted amino, glycine ester, halide (chloro, bromo, iodo) or OR (OR is a leaving group such as mesylate, triflate, or tosylate) or an activated leaving group; $R^1$ is selected from hydrogen, or substituted or unsubstituted lower alkyl; $R^2$ and $R^3$ are each selected from hydrogen or a thiol protecting group, or an inter or intramolecular disulfide; and $R^4$, $R^5$, $R^7$ and $R^8$ are each selected from hydrogen or lower alkyl.

When R, $R^6$ or $R^{10}$ is a carboxylic acid derivative, $R^9$ can be an activated leaving group. For purposes of this invention the leaving group $R^9$ is defined such that (compound)-COR$^9$ is an acylating agent. Examples of activated leaving groups suitable for the practice of this invention include, for example: halide; substituted or unsubstituted aryloxy groups such as phenoxy, pentachlorophenoxy, etc.,; oxy-heterocyclic groups such as N-oxy-succinimido, etc.; mercapto; lower alkylthio; arylthio; oxyphosphonium; and other groups known to those skilled in the art to be useful as leaving groups.

$R^2$ and $R^3$ can be hydrogen or any known thiol protecting group. Examples of such groups include lower alkylaminocarbonyl such as ethylaminocarbonyl, lower alkanoylaminomethyl, aroylaminomethyl, t-butyl, acetamidomethyl, arylmethyl such as triphenylmethyl (trityl) and diphenylmethyl, aroyl such as benzoyl, aryloxycarbonyl such as phenoxycarbonyl, arylloweralkoxycarbonyl, preferably arylmethoxycarbonyl, benzyloxycarbonyl, and lower alkoxycarbonyl such as t-butoxycarbonyl. Preferred thiol protecting groups include trityl, t-butyl, diphenylmethyl, acetamidomethyl and benzoyl and an inter or intramolecular disulfide.

The term "lower alkyl" when used herein designates aliphatic saturated branched or straight chain hydrocarbon monovalent substituents containing from 1 to 6 carbon atoms such as methyl, ethyl, isopropyl, n-propyl, n-butyl, etc., more preferably 1 to 4 carbons. The term "lower alkoxy" designates lower alkoxy substituents containing from 1 to 6 carbon atoms such as methoxy, ethoxy, isopropoxy, etc., more preferably 1 to 4 carbon atoms.

The terms substituted lower alkyl or substituted lower alkoxy when used herein include alkyl and alkoxy groups substituted with halide, hydroxy, carboxylic acid, or carboxamide groups, etc. such as, for example, —CH$_2$OH, —CH$_2$CH$_2$COOH, —CH$_2$CONH$_2$, —OCH$_2$CH$_2$OH, —OCH$_2$COOH, —OCH$_2$CH$_2$CONH$_2$, etc.

The term substituted amino when used herein includes such groups mono or di and tri-substituted with lower alkyl, and —NH$_3^+$ or mono, di and tri-substituted ammonium groups substituted with lower alkyl with a pharmacologically suitable anion.

The term glycine ester as used herein means the lower alkyl esters of glycine, preferably the methyl and ethyl esters. These chelating ligands can be complexed with a radionuclide, e.g., technetium, to form the following complexes:

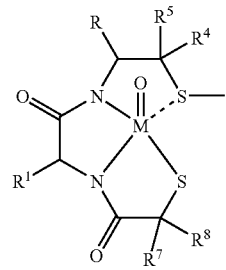

XI

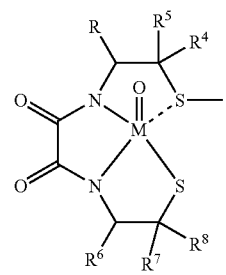

X

-continued

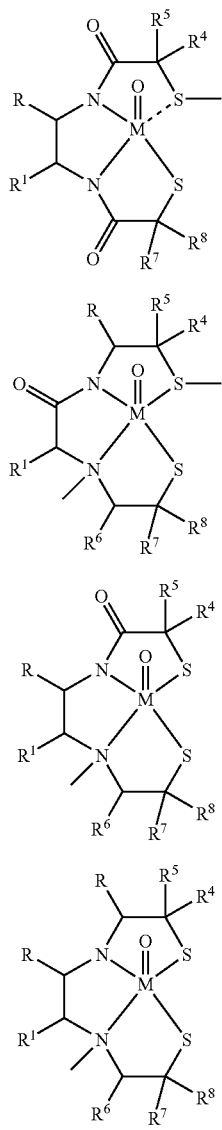

XI

XII

XIII

XIV where the R groups are defined as above.

Preferred embodiments of the invention use chelating ligands that are formed from monoaminomonoamide compounds having structures of formula V, VI or VII, e.g., N-{2-((2-(((triphenylmethyl)-thio)-ethyl)amino) acetyl}-S-(triphenylmethyl)-2-aminoethanethiol ("MAMA'").

Any organic linker having a backbone chain length of 1 to about 6 carbon atoms can be used to attach the chelating ligand, typically through its nitrogen, sulfur, R, $R^1$ or $R^6$, to the 8-nitrogen atom of the tropane ligand (which binds the dopamine transporter). Examples of linkers include —$(CH_2)_n$— where n is an integer from 1 to 6, or —$(CH_2)_n$-(aryl, arylalkyl, ethenyl or ethynyl)-$(CH_2)_m$ where the sum of n plus m is an integer from 1 to 6.

Preferred radiolabeled compounds of the present invention cross the blood brain barrier and exhibit desired target:non-target specificity. Preferably, the selectivity ratio of binding (DAT:SET) is about 30 or more, more preferably 50 or more. Thus, they are useful as brain imaging agents, for example, for imaging DAT.

The tropane ligands can be linked to the chelating ligand by an initial conversion to nortropanes. Syntheses of nortropanes are known in the art, for example, as disclosed in Meltzer, P. C., et al., *J. Med. Chem.* 1993, 36, 855–862; Meltzer, P. C., et al., *J. Med. Chem.* 1994, 37, 2001–2010 (the disclosure of which is incorporated herein by reference). Tropanes can be synthesized from tropinone or cocaine by techniques known in the art. Synthesis of the nortropanes can then be achieved by N-demethylation of the tropane, which can be readily accomplished by various methods known in the art, e.g., with α-chloroethyl chloro formate (ACE-Cl).

The chelating ligand is preferably prepared separately and, then, either attached to the nortropane and metallated, or metallated first followed by attachment to the appropriate nortropane. When the radiolabeled compounds of the invention are required to cross the blood brain barrier, the chelating ligands useful in the present invention form neutral complexes with the radionuclide and are lipid soluble. Chelating ligands that form neutral $^{99m}Tc(V)$ complexes which are useful in the present invention include a substituted oxime (Loberg, M. D., et al., *J. Nucl. Med.* 1979, 20, 1181–1188), $N_2S_2$ compounds (Davison, A., et al., *Inorg. Chem.* 1981, 20, 1629–1632; Davison, A., et al., *J. Nucl. Med.* 1979, 20, 641 (abstr)), bisaminoethanethiol ("BAT") (Kung, H. F., et al., *J. Med. Chem.* 1985, 28, 1280–1284; Kung, H. F., et al., *J. Nucl. Med.* 1986, 27, 1051; Kung, H. F., et al., *J. Med. Chem.* 1989, 32, 433–437; Kung, H. F., et al., *J. Nucl. Med.* 1984, 25, 326–332; Francesconi, L. C., et al., *Inorg. Chem.* 1993, 32, 3114–3124), and diaminodithiol ("DADT") (Lever, S. Z., et al., *J. Nucl. Med.* 1985, 26, 1287–1294). Additional examples of useful chelating ligands include N,N'-bis(2-mercapto-1-methyl)-2-aminobenzylamine ("U-BAT") (Francesconi, L. C., et al., *J. Med. Chem.* 1994, 37, 3282–3288), propylene amine oximes ("HMPAO"), diamidodithiol ("DADS") (Rao, T. N., et al., *J. Am. Chem. Soc.* 1990, 112, 5798–5804; Stepniak-Biniakiewicz, D., et al., *J. Med. Chem.* 1992, 35, 274–279), phenylenediamine-thiol-thioether ("PhAT") (McBride, B. J., et al., *J. Med. Chem.* 1993, 36, 81–86), bis(mercaptoethyl)-2-aminoethylamine ("SNS") or bis(mercaptoethyl)-2-thioethylamine (Mastrostamatis, S. G., et al., *J. Med. Chem.* 1994, 37, 3212–3218), monoamine amide ("MAMA") (Gustavson, L. M., et al., *Tet. Lett.* 1991, 32, 5485–5488) and N-{2-((2-(((triphenylmethyl)thio)ethyl)amino)acetyl}-S-(triphenylmethyl)-2-aminoethanethiol ("MAMA'") (O'Neil, J. P., et al., *Inorg. Chem.* 1994, 33, 319–323). For example, when MAMA' is attached to a lipophilic tropane by a linker in accord with the present invention, a neutral, moderately lipophilic and aqueous stable compound suitable for radiolabeling is formed.

Compounds of formula III and IV can be synthesized according to the methods described in U.S. Pat. No. 4,673,562 which is incorporated herein by reference. Compounds of formula V can be synthesized by methods known in the art (see Fritzberg et al., *J. Nucl. Med.* 1981, 22, 258–263). Compounds of formula VI can also be synthesized by methods known in the art. (See O'Neil, J. P., et al., *Inorg. Chem.* 1994, 33, 319–323).

Radiolabeled complexes of the present invention can be prepared via three general preparation procedures as outlined in the General Scheme (FIG. 1). The general preparation scheme exemplifies the use of trityl protecting groups for the sulfhydryls, however, other protecting groups that are known to be useful for sulfhydryl protection can also be used such as, for example, lower alkylaminocarbonyl such as ethylaminocarbonyl, lower alkanoylaminomethyl, arylaminomethyl, t-butyl, acetamidomethyl, arylmethyl such as triphenylmethyl(trityl) and diphenylmethyl, aryl such as benzoyl, aryloxycarbonyl such as phenoxycarbonyl, aryl loweralkoxycarbonyl, preferably arylmethoxycarbonyl such as benzyloxycarbonyl, and lower alkoxycarbonyl such as t-butoxycarbonyl. Preferred sulfhydryl protecting groups include trityl, t-butyl, diphenylmethyl, acetamidomethyl, disulfide and benzoyl.

The compounds of the invention can be prepared by known means based upon the present disclosure. For example, starting with an appropriate chelating ligand, such as an $N_2S_2$ compound, illustrated in the general scheme in FIG. 1 as N-{2-((2-((triphenylmethyl)thio)ethyl)amino) acetyl}-S-(triphenylmethyl)-2-aminoethanethiol, (MAMA': Katzenellenbogen et al., *Inorg. Chem.*, 1994, 33, 319), the $N_2S_2$ compound can be alkylated with either the haloalkyl triflate or the haloalkylnortropane (prepared from the nortropane: Meltzer et al., *J. Med. Chem.*, 1993, 36, 855), producing the chloroalkyl (propyl shown) MAMA', or the tropanalkyl (propyl shown) MAMA', compounds, respectively. The chloroalkyl (propyl shown) MAMA' compound, can then be attached to a suitable nortropane to provide the tropanalkyl (propyl shown) MAMA' compounds, as shown. Alternatively, the chloroalkyl (propyl shown) MAMA', can be treated to incorporate a metal atom, preferably a radionuclide (such as $^{99}$Tc, $^{99m}$Tc, $^{188}$Re or $^{186}$Re) to provide the M-labeled complex. The resulting complex can then be attached to a suitable nortropane to provide radiopharmaceutical compounds of the present invention, as shown.

Alternatively, the tropanalkyl (propyl shown) MAMA' compounds, can be treated to incorporate a radionuclide (such as $^{99}$Tc, $^{99m}$Tc, $^{188}$Re or $^{186}$Re) to form radiopharmaceutical compounds of the present invention, as shown.

The compounds of the present invention can be either diastereoisomer as well as a mixture of both diastereomers. The diastereoisomers can be separated by column chromatography.

More specifically, alkylation of the $N_2S_2$, with haloalkyl triflate to produce the chloroalkyl (propyl shown) MAMA', can be used to prepare the linker which is used to bind the chelating ligand to the tropane ligand, which selectively binds the dopamine transporter. This alkylation step can be modified by those of ordinary skill in organic chemistry to create various linkers having a backbone chain length of 1 to about 6 carbon atoms, as described above.

Deprotection of the chloroalkyl compound can be accomplished by standard methods well known in the art, e.g., with $H_2S/Hg(OAc)_2$ (O'Neil, J. P., et al., *Inorg. Chem.* 1994, 33, 319–323) or $AgNO_3$/Py (DiZio, J. P., et al., *Bioconj. Chem.* 1991, 2, 353–366), with TFA and phenol, or HBr in acetic acid (Zervas, L., et al., *J. Amer. Chem. Soc.* 1962, 84, 3887–3897) to result in the unprotected bisthiol which can then be immediately treated with a solution of tin (II) chloride ($SnCl_2$) and sodium perrhenate ($Na_2ReO_7$) or an agent such as $Na(^{99m}TcO_4)$/stannous tartrate (Francesconi, L. C., et al., *Inorg. Chem.* 1993, 32, 3114–3124; Canney, D. J., et al., *J. Med. Chem.* 1993, 36, 1032–1040) to produce the labeled complexes. Purification of these chelates can be accomplished by flash chromatography as described by O'Neil (O'Neil, J. P., et al., *Inorg. Chem.* 1994, 33, 319–323). The chloroalkyl chelate, can then be reacted (O'Neil, J. P., et al., *Bioconj. Chem.* 1994, 5, 182–193) with the appropriate nortropane to provide the labeled coordination complexes of the present invention. Alkylation of nortropanes can be accomplished by methods known in the art, e.g., acetonitrile ($CH_3CN$), potassium iodide (KI) and potassium carbonate ($K_2CO_3$). The use of strong base can cause epimerization of the carbomethoxy group at C-2, although sodium carbonate in a solvent such as dimethyl formamide (DMF) can yield alkylated products in reasonable yield.

These compounds can be prepared either as free bases or as a pharmacologically active salt thereof such as hydrochloride, tartrate, sulfate, naphthalene-1,5-disulfonate or the like.

Figure 2:
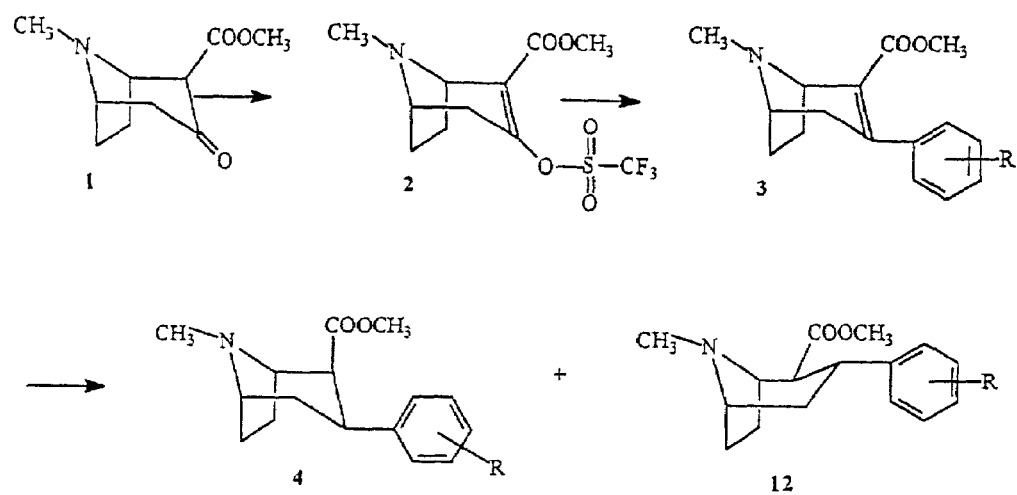
FIG. 2 is an illustration of a general scheme for preparation of 2-carbomethoxy tropanes (Scheme 1) comprising an aryl octene in accord with the present invention and subsequent preparation of 3α and 3β diasteriomers thereof.

Reaction schemes for preparation of various classes of compounds of the present invention are described with reference to the drawings. In Scheme 1, as illustrated in FIG. 2, Keto ester 1 {Meltzer et al., *J. Med. Chem*, 1994, 37, 2001} is converted to the enol triflate 2 by reaction with N-phenyltrifluoromethanesulfonimide and sodium bis(trimethylsilyl)amide in tetrahydrofuran. The enol triflate 2 is then coupled with the appropriate commercial or preformed arylboronic acids by Suzuki coupling in diethoxymethane in the presence of lithium chloride, sodium carbonate and tris(dibenzylideneacetone)dipalladium(0) to provide aryl octenes 3 in excellent yield.

Reduction of the octenes 3 with samarium iodide in tetrahydrofuran/methanol at low temperature (–78° C.) provides a mixture of the 3β- and 3α-diastereomers, 4 and 12 respectively. These diastereomers are readily separated by flash column chromatography.

Figure 8:
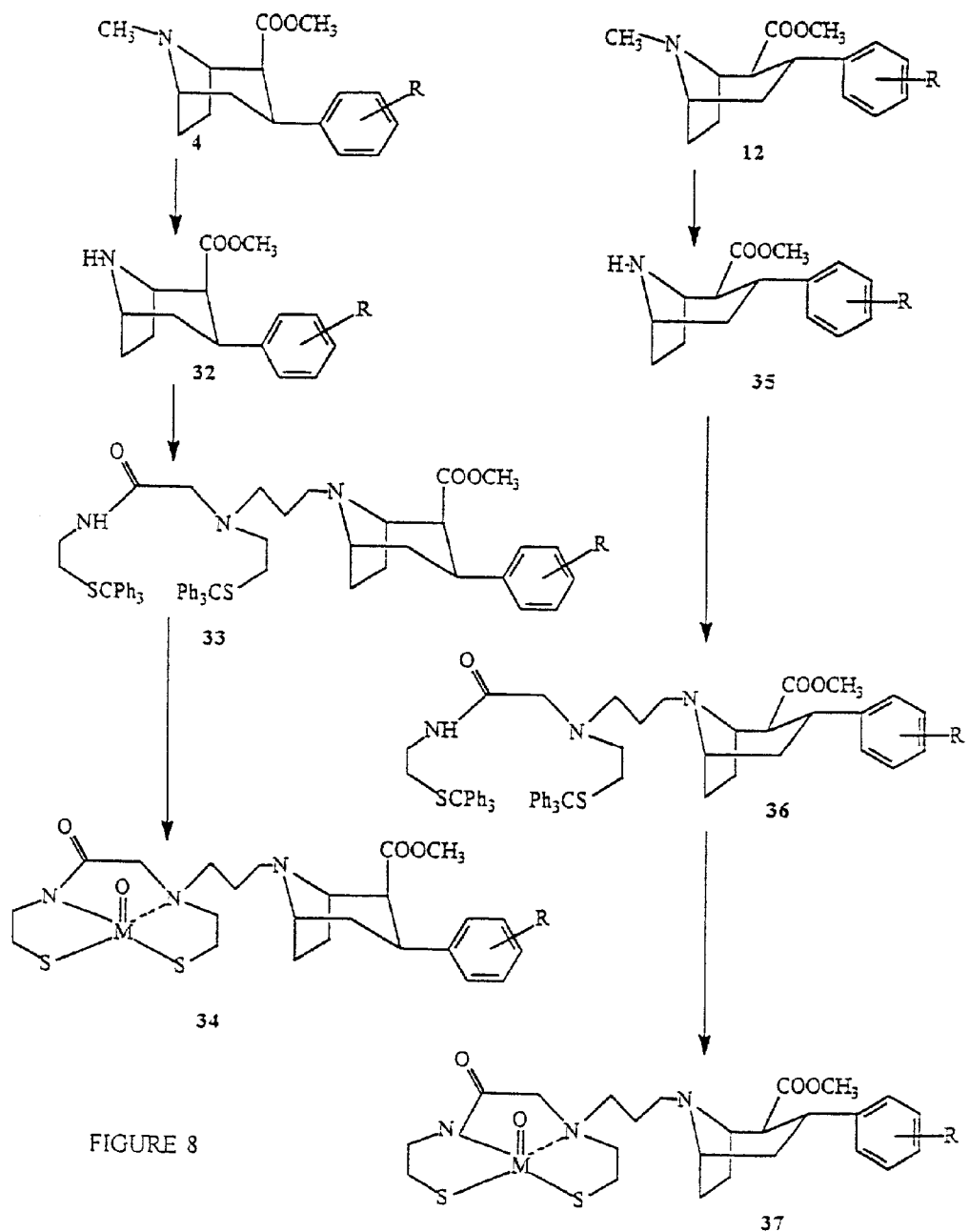
FIG. 8 is an illustration of a general scheme for converting the 3α and 3β diasteriomers of FIG. 2 to bistrityl protected $N_2S_2$ tropanes and labeling with technetium or rhenium (Scheme 7).

In Scheme 7, as illustrated in FIG. 8, the 3β- and 3α-diastereomers 4 and 12 are then treated similarly in their conversion to the bistrityl protected $N_2S_2$ tropanes 33 and 36 respectively and thence to the rhenium analogs 34R and 37R and the technetium analogs 34T and 37T. Thus, the tropanes are N-dealkylated by treatment with ACE-chloride {Meltzer et al., *J. Med. Chem*, 1993, 36, 855} to provide the nortropanes 32 and 35. Introduction of the $N_2S_2$ protected, ligand is then achieved by reaction of the nortropanes with the preformed N-[[[2-[2-(triphenylmethyl)thio]-ethyl](N'-3'-chloropropyl)amino]acetyl]-S-(triphenylmethyl)-2-aminoethanethiol (MAMA'-Cl){Meltzer et al. *J. Med. Chem.*, 40, 1835, 1997} in the presence of potassium iodide and potassium carbonate. Rhenium can then be introduced upon reaction with tin (II) chloride in 0.05 M HCl, followed by sodium perrhenate in 0.05 M HCl. The product is purified by silica gel column chromatography and obtained as a mixture of diastereomers. An alternative approach utilizes N-alkylation of the nortropanes with preformed N-[(2-((3'-chloropropyl)(2-mercaptoethyl)amino)acetyl]-2-aminoethane-thiolato]rhenium (V) oxide {Meltzer et al. *J. Med. Chern.*, 40, 1835, 1997}. Both diastereomers of the metal chelate are prepared.

Figure 3:
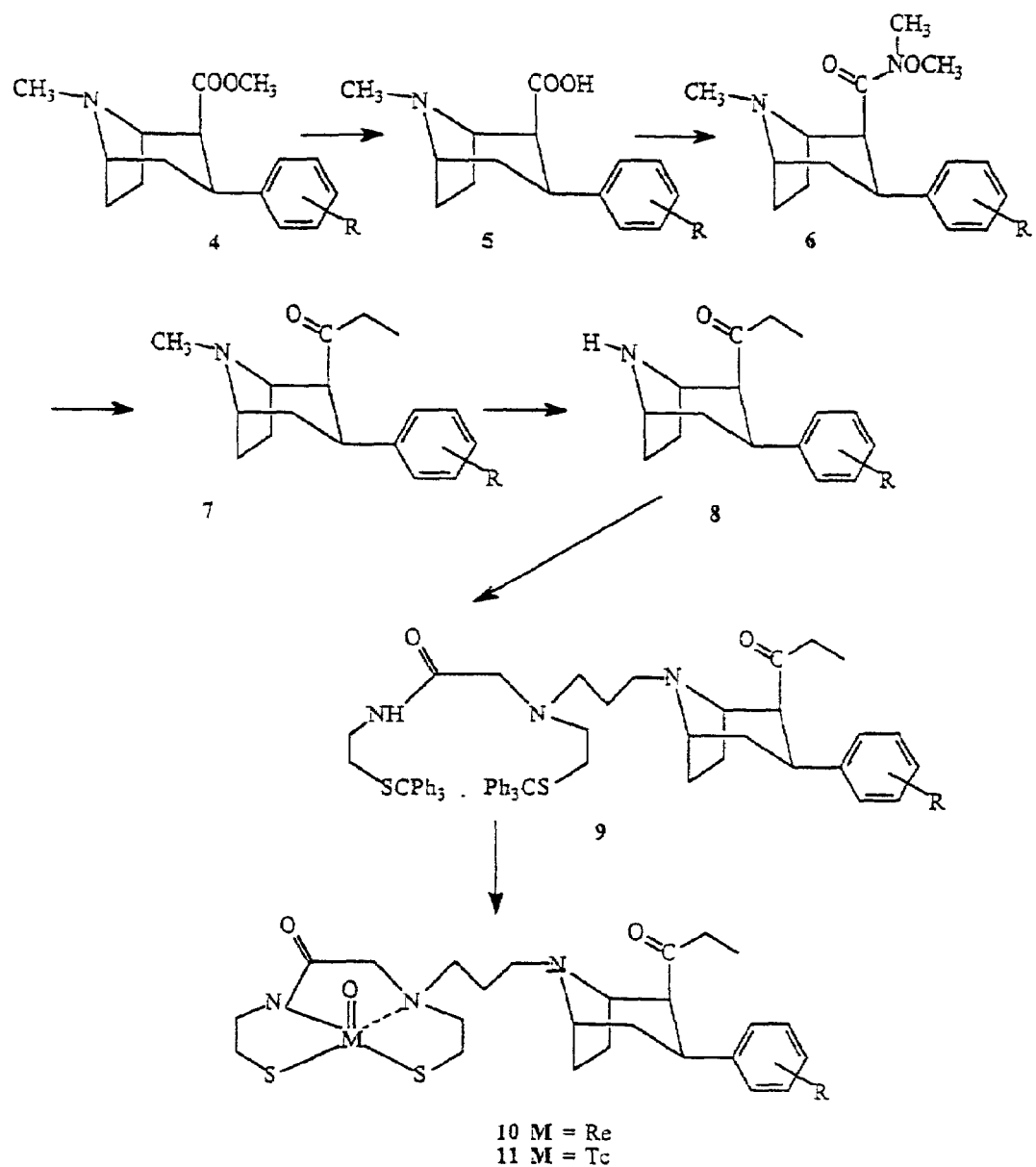
FIGS. 3 and 4 are illustrations of a general scheme for preparation of 2-ethylketo analogs (Schemes 2 and 3) of radiopharmaceutical compounds in accord with a preferred embodiment of the present invention.
Figure 4:
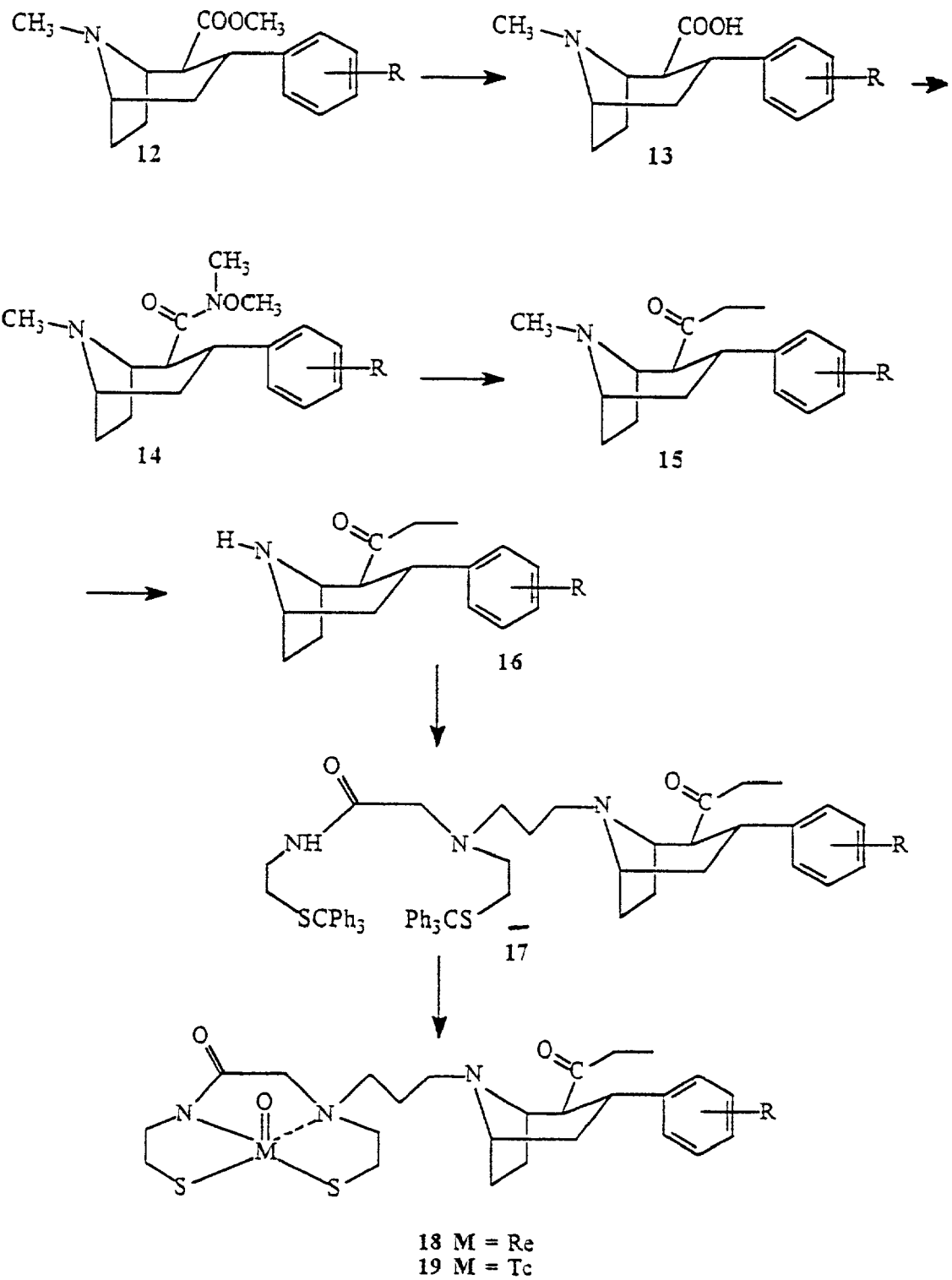

In Schemes 2 and 3, as illustrated in FIGS. 3 and 4, the 2-ethylketo analogs in both the 3α- and 3β-series are prepared as shown. This discussion exemplifies the 3β-diastereomer, as illustrated in FIG. 3. The 3βdiastereomer 4 is hydrolyzed in dioxane/water or with lithium hydroxide to provide the acid, 5 which is converted to the amide through conversion to the acid chloride with oxalyl chloride and then reaction with (MeO)MeNH.HCl to provide 6. Further reaction with alkyl Grignard at low temperature provides the desired ethyl or alkyl ketone 7. The alkyl ketone 7 can be made alternatively by reaction of the ester-tropane (4 or 12) with the appropriate alkyl-Grignard-(ethylmagnesium bromide in this case) (Ref: I. Kikkawa and T. Vorifuji, *Synthesis* (1980), p. 877). Demethylation is by standard treatment with ACE-Cl to obtain 8. The chelating unit is attached by reaction of 8 with MAMA'-Cl in the presence of a base such as potassium carbonate or potassium bicarbonate and potassium iodide. Insertion of rhenium to provide 10 or technetium to provide 11 is accomplished with sodium perrhenate under reductive conditions, of the technetium heptogluconate. Both diastereomers of the metal chelate can be prepared in a similar manner. As seen by comparing Schemes 2 and 3, the 3α-diastereomer of the tropane is prepared in a similar manner.

Figure 5:
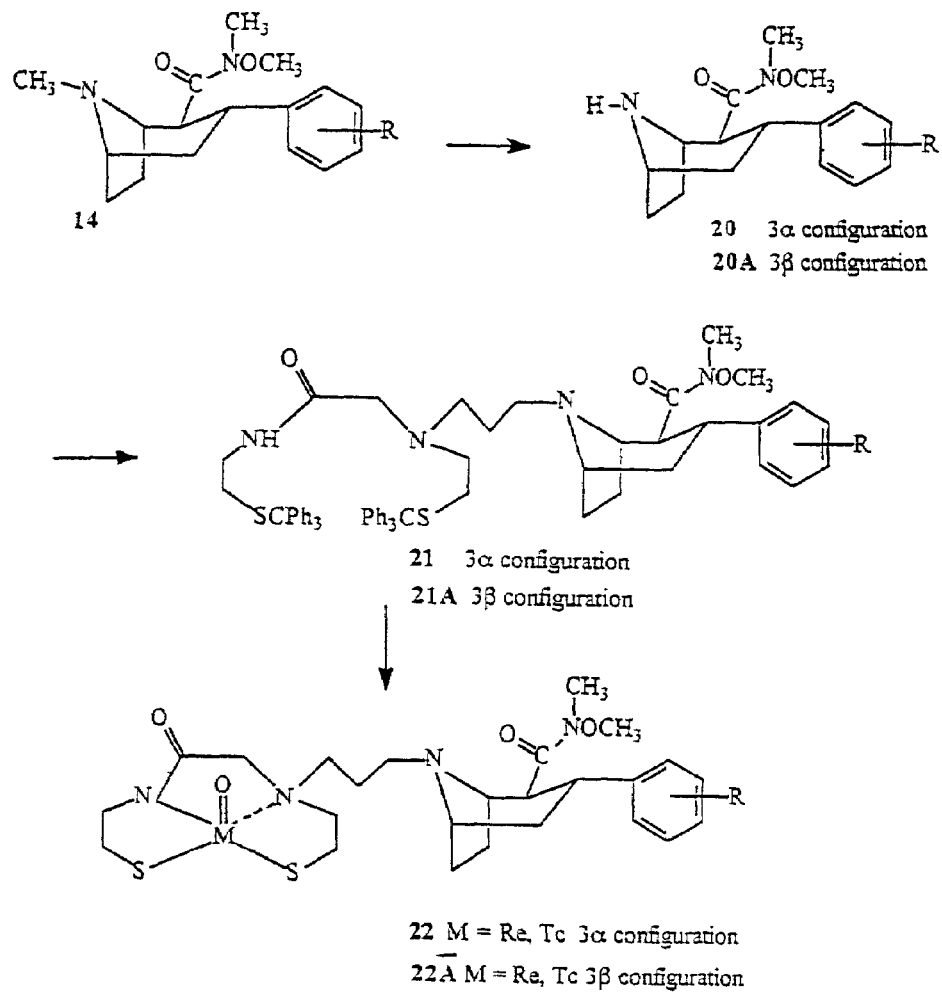
FIG. 5 is an illustration of a general scheme for preparation of 2-carboxamido 3α- or 3β-aryl analogs (Scheme 4) of radiopharmaceutical compounds in accord with a preferred embodiment of the present invention.

In Scheme 4, as illustrated in FIG. 5, the 2-carboxamide analogs 22 and 22A are prepared from 14 by N-demethylation with ACE-Cl as described earlier.

Attachment of the MAMA' group and insertion of the metal (rhenium or technetium) is conducted as described earlier for Schemes 2 and 3.

Figure 6:
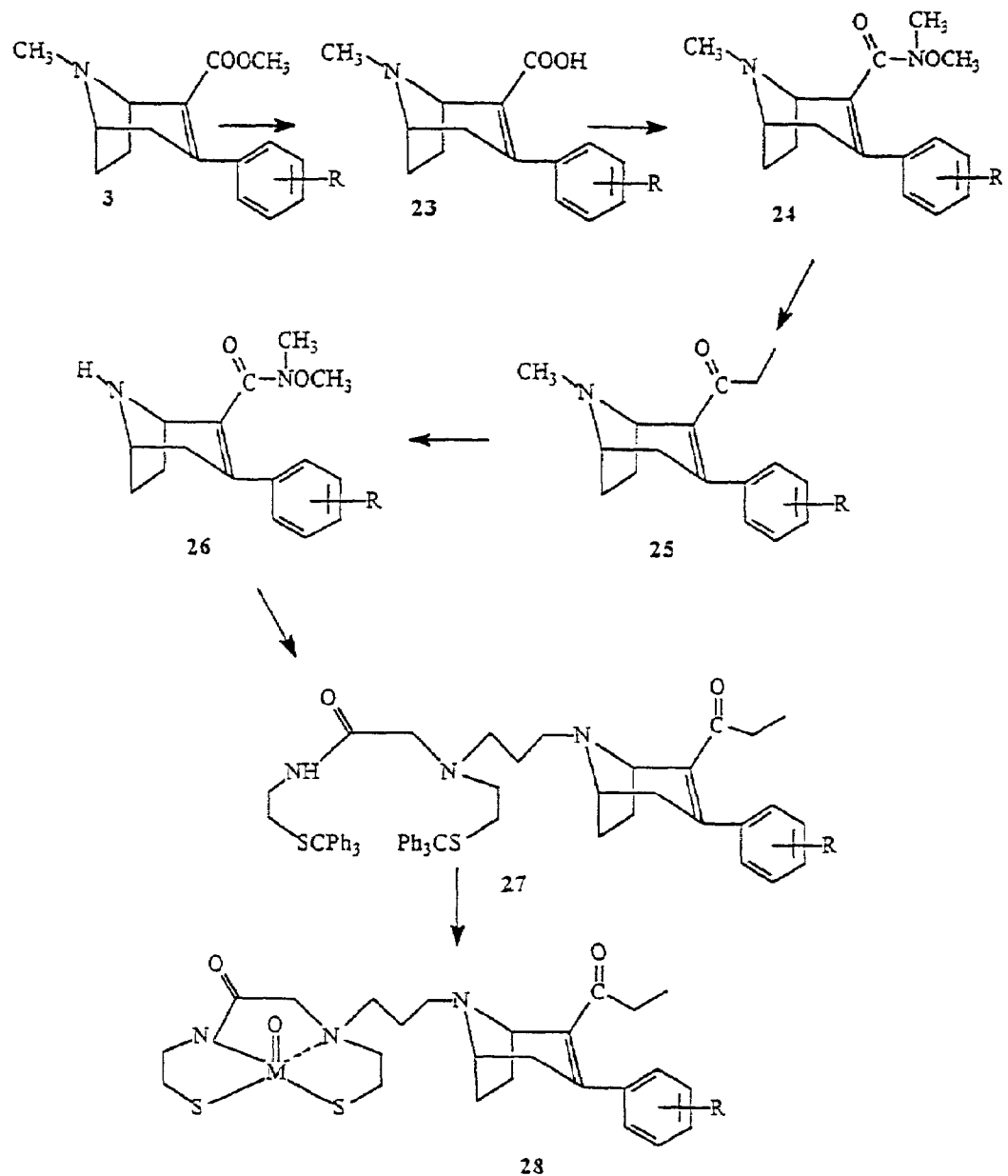
FIG. 6 is an illustration of a general reaction scheme for preparation of 3-aryl-2-ethylketo-2,3-ene analogs (Scheme 5) of radiopharmaceutical compounds in accord with a preferred embodiment of the present invention.

In Scheme 5, as illustrated in FIG. 6, the 2-ethylketo trop-2-ene analogs are prepared as shown in the scheme. Thus, ester 3 is hydrolyzed in dioxane/water or with lithium hydroxide to provide the acid 23 which is converted to the amide through conversion to the acid chloride with oxalyl chloride and then reaction with (MeO)MeNH.HCl to provide 24. Further reaction with alkyl Grignard at low temperature provides the desired ethyl or alkyl ketone 25. The alkyl ketone 25 can be formed altneratively by reaction of the ester tropene (3) with the appropriate alkyl-Grignard-(ethylmagnesium bromide) (Ref: I. Kikkawa and T. Vorifuji, *Synthesis* (1980), p. 877). Demethylation is by standard treatment with ACE-Cl to obtain 26. The chelating unit is attached by reaction of 26 with MAMA'-Cl in the presence of a base such as potassium carbonate or potassium bicarbonate and potassium iodide. Insertion of rhenium or technetium to provide 28 is accomplished with sodium perrhenate under reductive conditions of the technetium heptogluconate. Both diastereomers of the metal chelate 28 are prepared.

Figure 7:
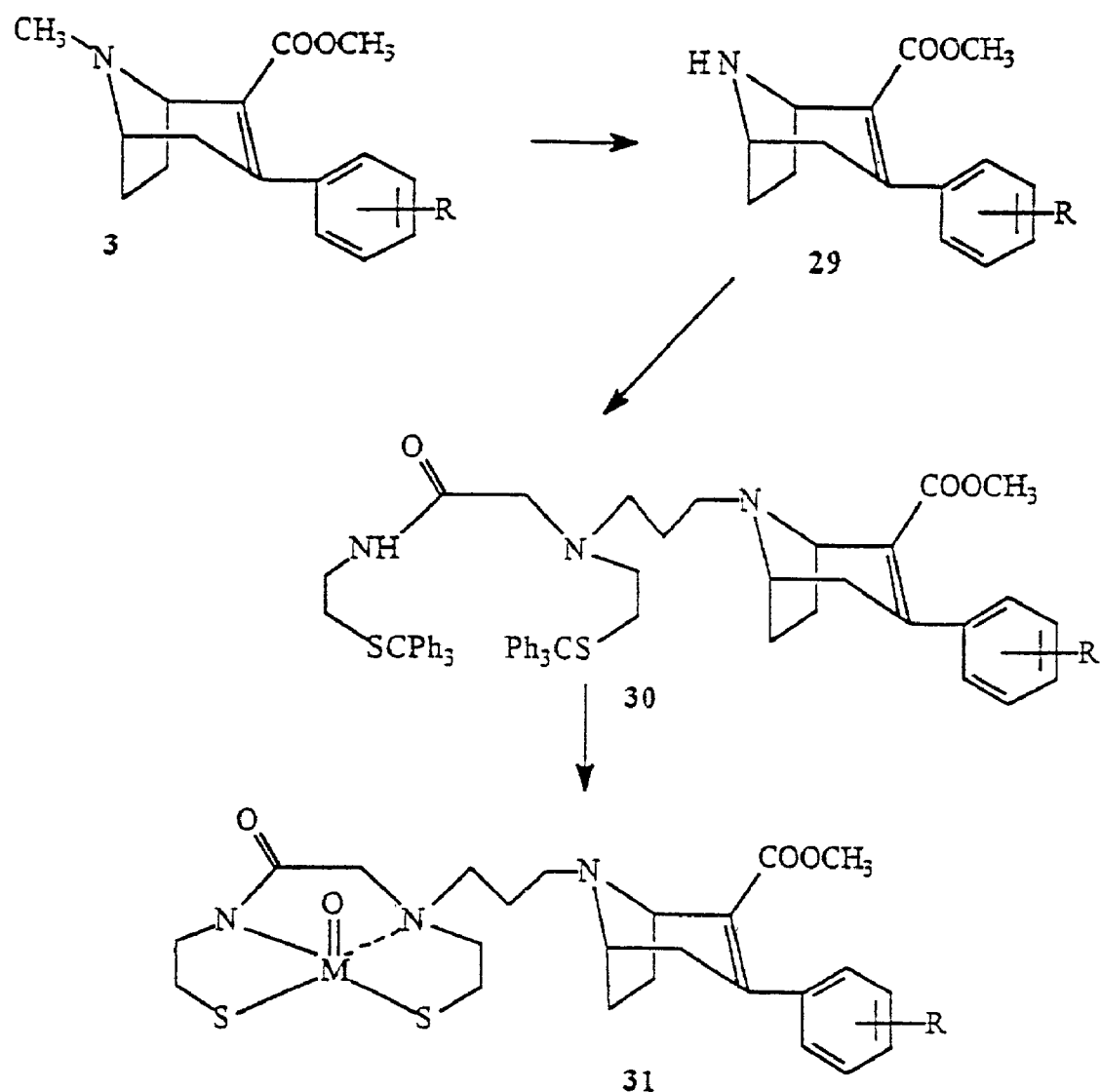
FIG. 7 is an illustration of a general reaction scheme for preparation of 3-aryl-2-carbomethoxy-2,3-ene analogs (Scheme 6) of radiopharmaceutical compounds in accord with a preferred embodiment of the present invention.

In Scheme 6, as illustrated in FIG. 7, the 2-carbomethoxy trop-2-ene analogs are prepared as shown in the scheme. Demethylation of compound 3 is by standard treatment with ACE-Cl to obtain compound 29. The chelating unit is attached by reaction of compound 30 with MAMA'-Cl in the presence of a base such as potassium carbonate or potassium bicarbonate and potassium iodide. Insertion of rhenium or technetium to provide compound 31 is accomplished with sodium perrhenate under reductive conditions, of the technetium heptogluconate. Both diastereomers of the metal chelate 31 are prepared.

Figure 9:
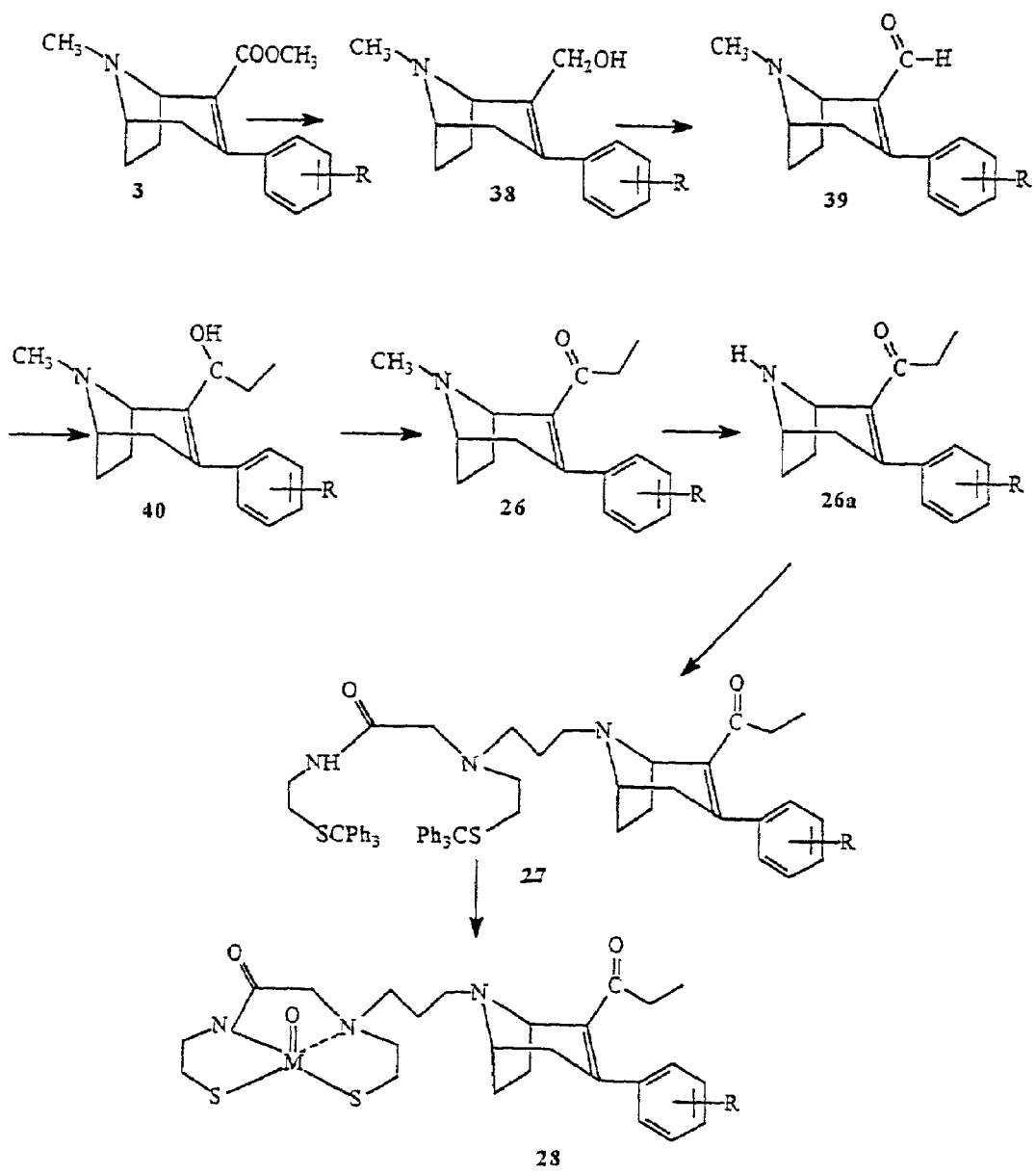
FIG. 9 is an illustration of an alternative general reaction scheme for preparation of 3-aryl-2-ethylketo-2,3-ene analogs (Scheme 8) of radiopharmaceutical compounds in accord with a preferred embodiment of the present invention.

In Scheme 8, as illustrated in FIG. 9, the 2-ethylketo trop-2-ene analogs are prepared as shown in the scheme. Thus, compound 3 is reduced with LAH and reoxidized to obtain the aldehyde 39. Reaction of the aldehyde with ethyl lithium or ethyl Grignard provides the alcohol 40 which is oxidized once again to obtain the ethyl ketone 26. Compounds 27 and 28 are then obtained as above.

Figure 10:
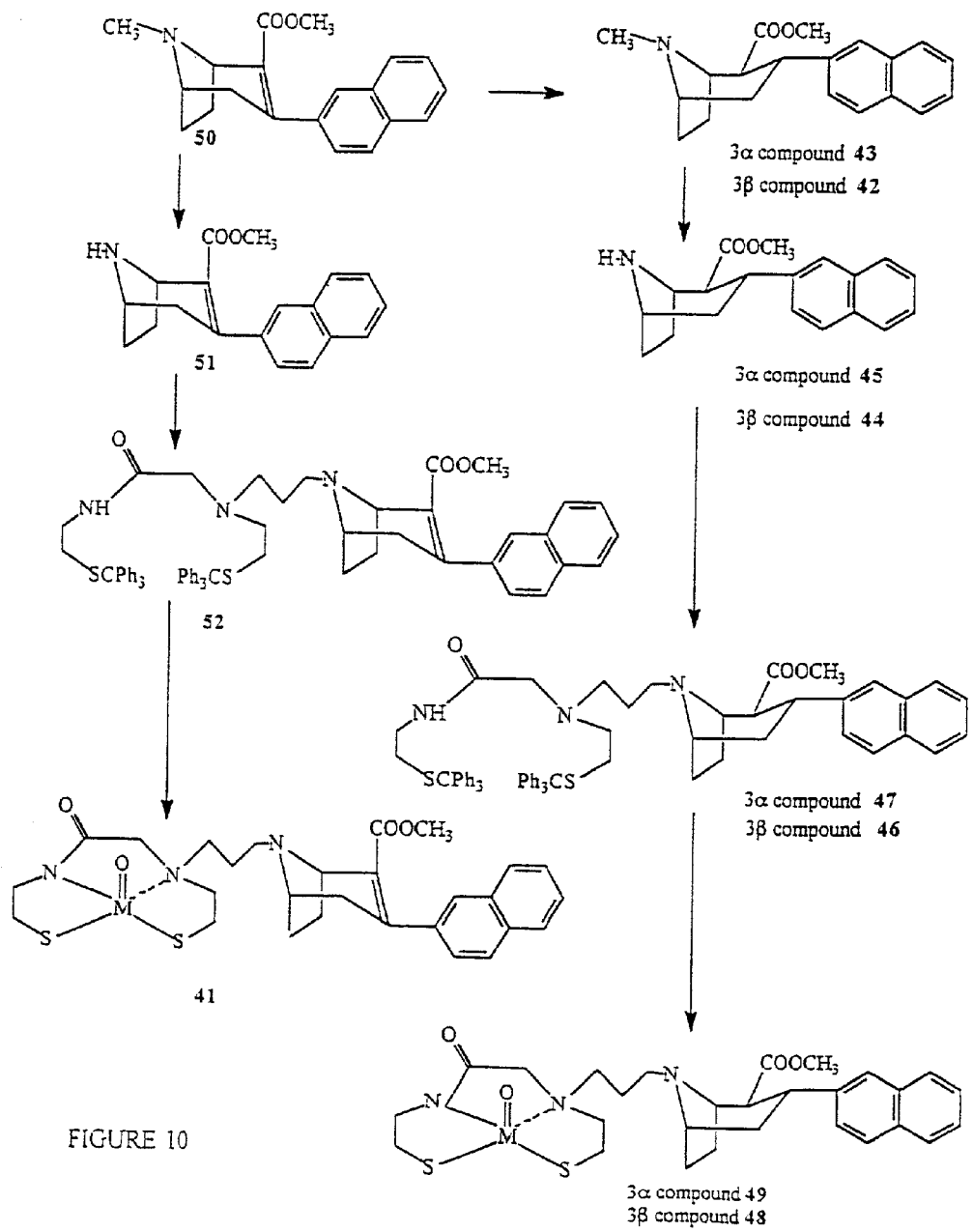
FIG. 10 is an illustration of a general reaction scheme for preparation of 3-naphthyl-2-carbomethoxy-2,3-ene and 3α-naphthyl or 3β-n aphthyl analogs (Scheme 9) of radiopharmaceutical compounds in accord with a preferred embodiment of the present invention.
Figure 11:
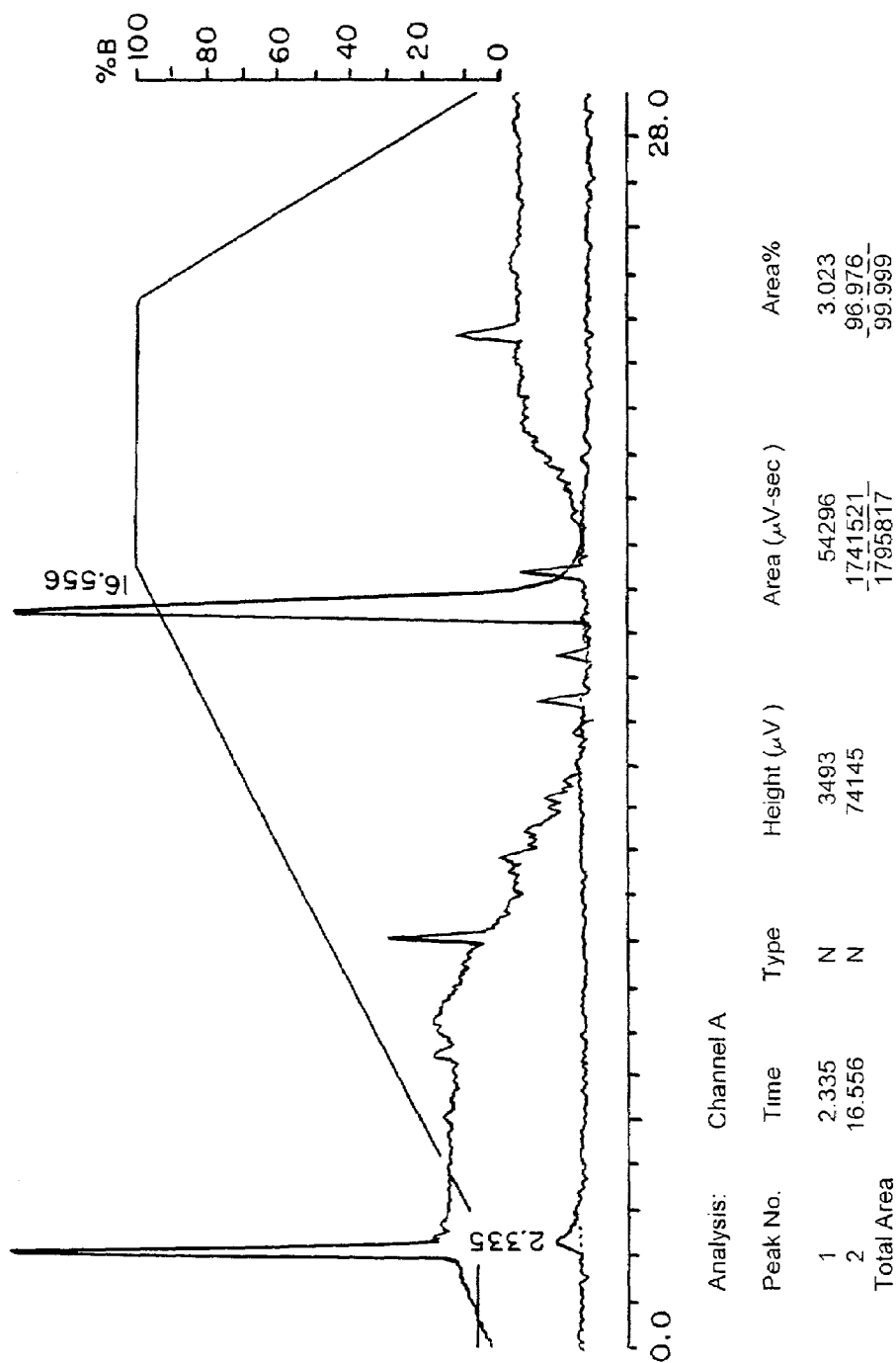
FIG. 11 is a HPLC chromatogram of $^{99m}$Tc labeled O-1505T.
Figure 12:
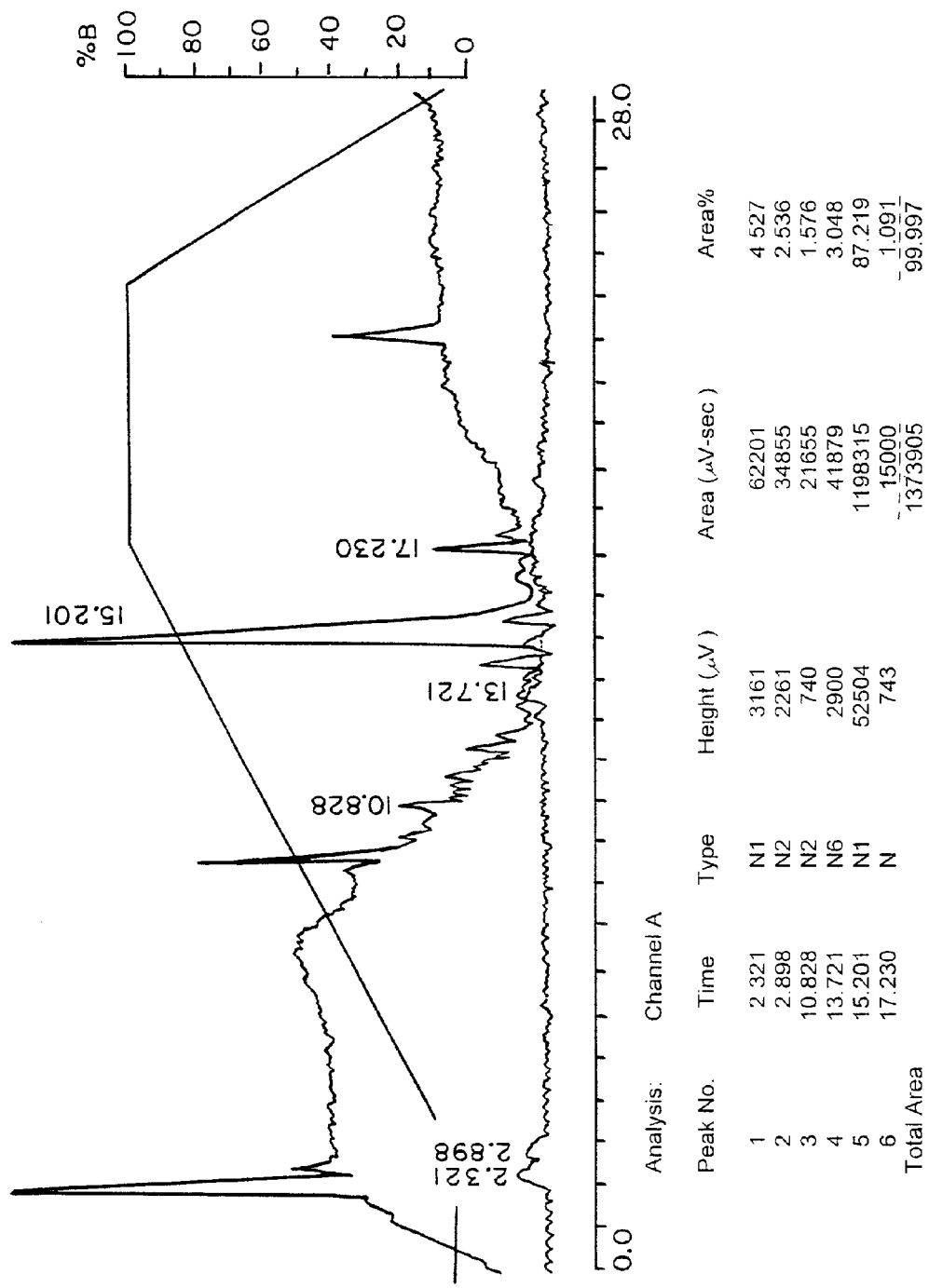
FIG. 12 is a HPLC chromatogram of $^{99m}$Tc labeled O-1508T.
Figure 13:
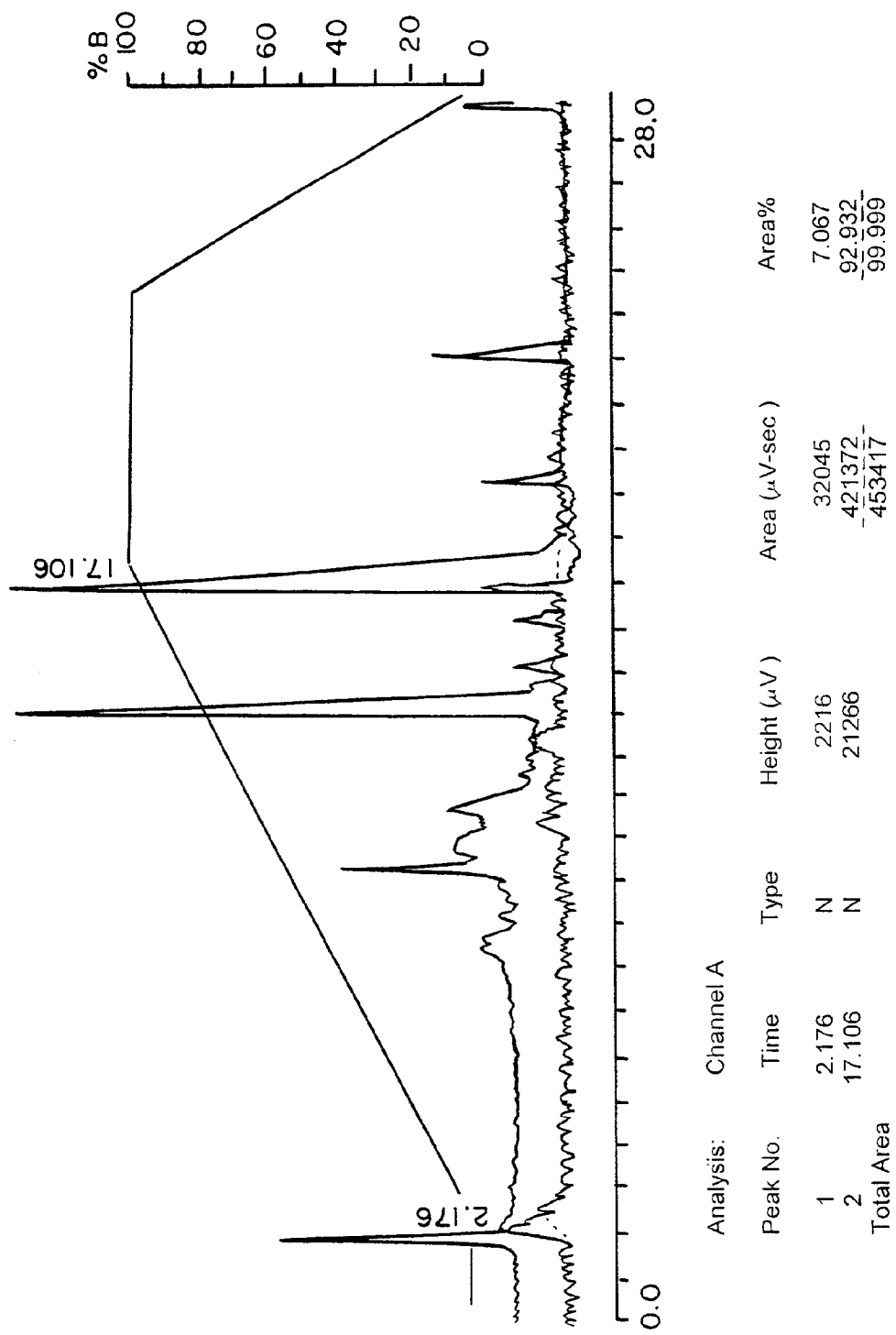
FIG. 13 is a HPLC chromatogram of $^{99m}$Tc labeled O-1561T.
Figure 14:
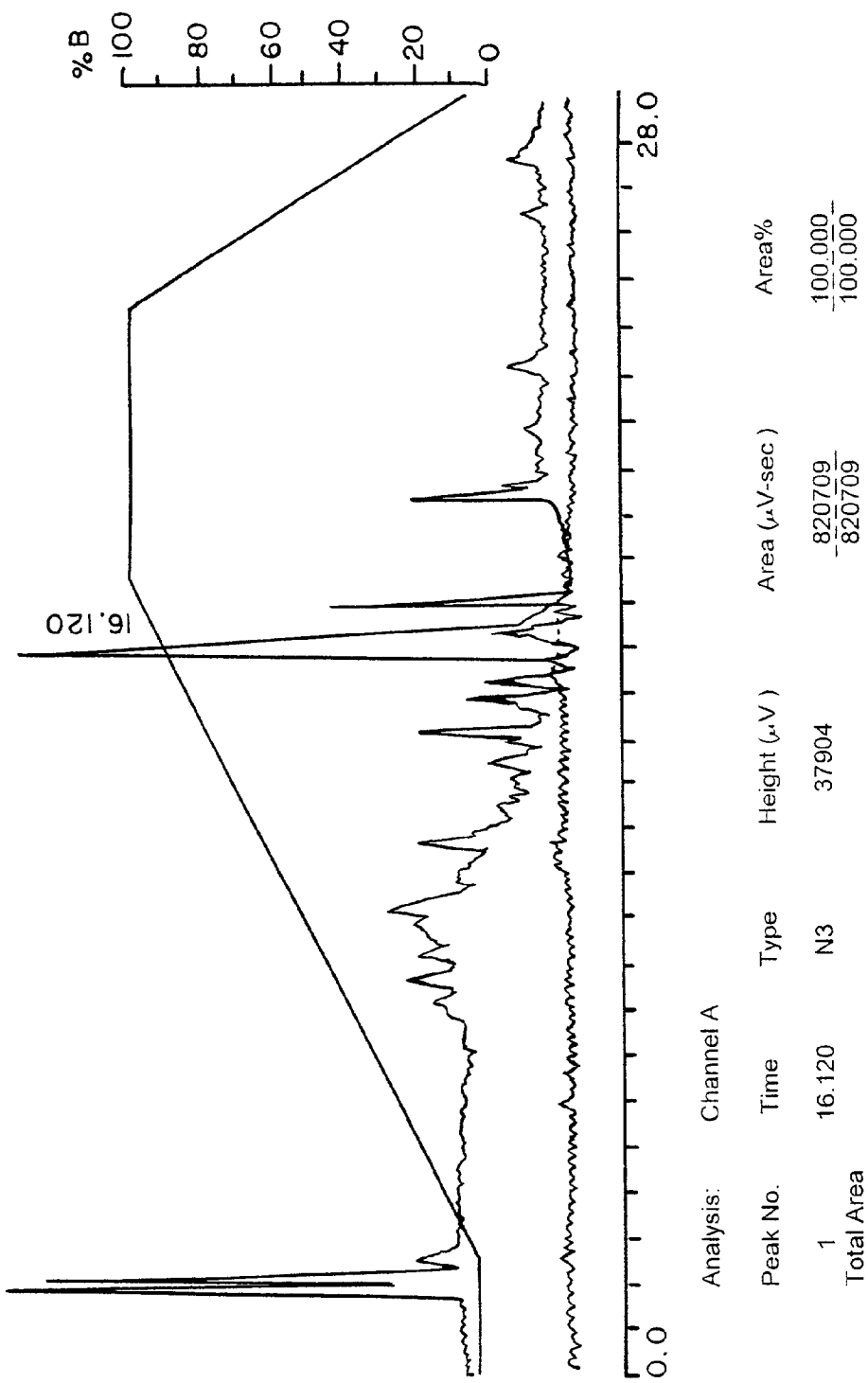
FIG. 14 is a HPLC chromatogram of $^{99m}$Tc labeled O-1560T.

In Scheme 9, as illustrated in FIG. 10, the 3-naphthyl trop-2-ene and 3α- and 3β-tropanes are obtained by similar chemistry to that described earlier. Thus, the trop-2-ene 38 is N-demethylated with ACE-Cl and the MAMA' is attached to provide compound 40. Rhenium or technetium are inserted as before to obtain the diastereomers 41. Alternatively, compound 38 is first reduced with samarium iodide to obtain both the boat and chair configured compounds 43 and 42. The same sequence of reactions then provides the rhenium and technetium diastereomers of both the 3α- and 3β-tropanes, 49 and 48.

The technetium or rhenium radionuclide complexes of this invention can be formed by reacting suitable precursor compounds with either pertechnetate or perrhenate in the presence of a suitable reducing agent in a conventional manner. For example, the compound can be dissolved in a suitable solvent with a reducing agent and then pertechnetate added. The mixture is then heated for a suitable length of time to complete the reaction. Typically, heating in a boiling water bath for about 10 minutes has been found sufficient to obtain very good yields of the radionuclide complex. To form rhenium complexes, $(Ph_3P)_2ReOCl_3$ is added in the presence of basic (NaOAc) methanol. Examples of reducing agents useful in the practice of this invention include stannous salts such as stannous chloride, sodium dithionite, and ferrous salts such as ferrous sulfate.

Rhenium behaves similarly to Tc. Thus, $N_2S_2$ complexes of Re or Tc are equally stable. Both metals form square pyramidal complexes with $N_2S_2$ ligands. (Francesconi, L. C., et al., *Inorg. Chem.* 1993, 32, 3114–3124). Rhenium is a preferred metal for use in studies which do not require the presence of a short half life radiolabel. For complexes with both technetium and rhenium, the oxygen occupies an apical position, therefore both syn and anti-isomers of the metal complexes are possible. The biological activity of Tc and Re chelates are generally similar. (O'Neil, J. P., et al., *Bioconjugate Chem.* 1994, 5, 182–193). $^{99m}Tc$ is a preferred radionuclide for use as an imaging agent. Rhenium is an excellent model for $^{99m}Tc$ and is also useful as a therapeutic agent.

A preferred method for introducing the technetium radionuclide was by reaction of the bistrtityl protected compounds in presence of anhydrous trifluoroacetic acid and then triethylsilane. A portion of the aqueous solution thus obtained was then incubated with $^{99m}Tc$-glucoheptonate solution (Glucoscan kits from Du Pont, Billerica, Mass.). HPLC separation on a $C_8$ reverse phase column equipped provides the major $^{99m}Tc$ labeled product which was reconstituted in sterile saline for injection.

The compounds of this invention are typically enantiomerically pure tropanes (either 1S or 1R configuration) attached by an achiral linker to a chiral chelating ligand. The chiral chelating ligand can be cis or trans with respect to the metal oxo and the linker, but is preferably cis. Each of the cis and trans chelating ligands exist as a pair of two enantiomers. By virtue of the chiral ligand which can exist in each of two enantiomeric forms, and a chiral tropane, each of the whole molecules exists as diastereoisomers. Radiopharmaceutical compositions of the present invention include the separate diastereoisomers of each, as well as mixtures of diastereomeric pairs.

The compounds of the present invention preferably have a target:nontarget ratio, such as a DAT:SET selectivity ratio of greater than 10, and preferably at least 30, to minimize binding of trace levels of the drug to the nontarget, e.g., serotonin transporter.

The present invention also provides pharmaceutical kits, preferably comprising the compounds of formula I with a reducing agent in lyophilized form in a pyrogen-free, sterilized container or vial. In this form the lyophilized composition can be readily reconstituted by adding only water, saline, or a buffer preferably having a pH in the range of 5 to 8, more preferably physiological pH. If technetium is the metal to be used as the radionuclide, pertechnetate solution from a technetium generator can be used for reconstitution.

In general, the radiopharmaceutical preparation kit comprises a sterilized unit dose (or multidose) vial containing the purified compound of formula I and a reducing agent for technetium, preferably lyophilized. Each dose should consist of a sufficient amount of compound and reducing agent to prepare the required dose for imaging, normally about 5 to about 30 mCi of $^{99m}Tc$ depending upon body weight of the mammal to be imaged. In use, the technetium, preferably as $^{99m}Tc$-pertechnetate in saline, is injected aseptically into the vial and the mixture reacted for a sufficient time to form the labeled complex. After reaction, typically, the resulting radiopharmaceutical is ready for use.

To image a desired target, a radiopharmaceutical preparation in accord with this invention having an effective dose of radioactivity for the particular mammal is prepared in a suitable pharmacological carrier, such as normal saline. Preferably, the radiopharmaceutical preparation is injected intravenously into the mammal. The target, e.g., the brain, is then imaged by positioning the mammal under a gamma camera or other suitable device.

In order to obtain high quality images, the radiochemical yield of bound technetium in the desired radiopharmaceutical should preferably be greater than 70% after reconstituting the lyophilized mixture and labelling. Lower yields may result in poorer image quality and undesirable purification steps may be required to produce high quality images.

This invention will be illustrated further by the following examples. These examples are not intended to limit the scope of the claimed invention in any manner.

The final compounds were characterized and their purity analyzed prior to biological evaluation. High field nuclear magnetic resonance (NMR) spectra were measured as well as low and high resolution mass spectra (MS) and infrared spectra (IR). Elemental analyses, thin layer chromatography (TLC) and/or high performance liquid chromatography (HPLC) were used as a measure of purity. A purity of >98% was obtained before biological evaluation of these compounds was undertaken.

In the following examples, NMR spectra were recorded on either a Bruker 100, a Varian XL 400, or a Bruker 300, or a Jeol 300 NMR spectrometer. TMS was used as intern al standard. Melting points are uncorrected and were measured on a Gallenkamp melting point apparatus. Opti cal rotations were measured at the sodium D line at 21° C. using a JASCO DIP 320 polarimeter (1 dcm cell). Thin layer chromatography (TLC) was carried out on Baker Si 250F. plates. Visualization was accomplished with either iodine vapor, UV exposure or treatment with phosphomolybdic acid (PMA). Preparative TLC was carried out on Analtech uniplates Silica Gel GF 2000 microns. Flash chromatography was carried out on Baker Silica Gel 40 M ($SiO_2$). Elemental Analyses were performed by Atlantic Microlab, Atlanta, Ga. A Beckman 1801 Scintillation Counter was used for scintillation spectrometry. 0.1% Bovine Serum Albumin and (−)-Cocaine were purchased from Sigma Chemicals. All reactions were conducted under an atmosphere of dry nitrogen.

[$^3$H]WIN 35,428 and 2β-carbomethoxy-3β-(4-fluorophenyl)-N-[$^3$H]methyltropane (79.4–87.0 Ci/mmol), and [$^3$H]citalopram (86.8 Ci/mmol) were purchased from DuPont-New England Nuclear (Boston, Mass.). TEA is triethylamine. (−)-Cocaine hydrochloride for the pharmacological studies was donated by the National Institute on Drug Abuse [NIDA]. Fluoxetine was donated by E. Lilly & Co. HPLC analyses were carried out on a Waters 510 system with detection at 254 nm on a Waters 8 mm, C-18, 10 m reverse phase column. $Pd_2dba_3$ is trisdibenzylideneacetone dipalladium, TFA is trifluoroacetic acid, THF is tetrahydrofuran, EtOAc is ethyl acetate.

EXAMPLE 1

(1R)-2-(Methoxycarbonyl)-3-[[(trifluoromethyl)sulfonyl]oxy]-trop-2-ene (Compound 2, FIG. 2)

(1R)-(−)-2-Methoxycarbonyl-3-tropinone, 1 {Meltzer et al., *J. Med. Chem*, 1994, 37, 2001} (1 g, 5.07 mmol) was dissolved in anhydrous THF (20 mL) and the resulting solution cooled to −78° C. A solution of sodium bistrimethylsilylamide (1 M, 5.58 mL, 5.58 mmol) was then added to the solution slowly. After 30 min, N-phenyltrifluoro-methane sulfonamide (1.94 g, 5.43 mmol) was added. The resulting solution stirred for a further 45 min at −78° C. and then allowed to attain room temperature and stirred at room temperature for 2 h. All solvent was evaporated and the residue pumped to dryness. Column chromatography was performed on the residue ($SiO_2$ 60 g; 2%–16% methanol in ethyl acetate) and gave 1.62 g (97%) of a yellow oil which crystallized on standing.

$R_f$ 0.65 (10% MeOH/EtOAc). $^1$H-NMR ($CDCl_3$) δ 1.58 (m, 1H), 1.97 (m, 2H), 2.1–2.2 (m, 2H), 2.39 (s, 3H). 2.84 (dd, J=18, 4 Hz, 1H), 3.42 (t, J=6 Hz, 1 H), 3.8 (s, 3 H), 3.92 (d, J=5 Hz, 1H).

EXAMPLE 2

(1R)-N-Methyl-2-methoxycarbonyl-3-(3,4-dichlorophenyl)-8-azabicyclo[3.2.1]oct-2-ene (Compound 3, FIG. 2)

(1R)-2-Methoxycarbonyl-3-[[(trifluoromethyl)sulfonyl]oxy]tropene 2 (620 mg, 1.88 mmol), LiCl (171 mg, 4.03 mmol), $Pd_2dba_3$ (69 mg, 0.075 mmol), aq. $Na_2CO_3$ (2.0 M, 2 mL), diethoxymethane (6.2 mL) were all charged to a flask and stirred vigorously. To this solution was added 3,4-dichlorophenyl boronic acid (474 mg, 2.49 mmol). The reaction was then brought to reflux for 2 h and filtered through celite. The cake was washed with ether and the organic solution was washed with concentrated $NH_4OH$. The washed solvent was dried with $K_2CO_3$, filtered, and evaporated. The residue was charged to a column ($SiO_2$, 60 g, eluted with 5–6% $Et_3N$/EtOAc) and gave 512 mg (83%) of a yellow oil which solidified upon standing.

$R_f$ 0.56 (10% $Et_3N$/EtOAc). IR (KBr) 2941, 1724, 1460, 1418, 1333, 1250, 1212, 1124 $cm^{-1}$. $^1$H-NMR ($CDCl_3$) δ 1.61 (m, 1H), 1.9–2.05 (m, 2H), 2.1–2.3 (m, 2H), 2.43 (s, 3H), 2.76 (dd, J=19, 4.7 Hz, 1H), 3.36 (t, J=4.9 Hz, 1H), 3.52 (s, 3H), 3.86 (d, J=5.5 Hz, 1H), 6.96 (dd, J=8.3, 1.9 Hz, 1H), 7.2 (d, J=2.2 Hz, 1H), 7.37 (d, J=8.2 Hz, 1H). Elemental analysis: calculated C, 58.91; H, 5.25; N, 4.29. found C, 58.84; H, 5.24; N, 4.24.

EXAMPLE 3

(1R)-N-Methyl-2β-methoxycarbonyl-3β-(3,4-dichlorophenyl)-8-azabicyclo[3.2.1]octane (Compound 4 (R=3,4-$Cl_2$), FIG. 2), and (1R)-N-Methyl-2β-methoxycarbonyl-3α-(3,4-dichlorophenyl)-8-azabicyclo[3.2.1]octane (Compound 12 (R=3,4-C12), FIG. 2)

To (1R)-N-Methyl-2-methoxycarbonyl-3-(3,4-dichlorophenyl)-8-azabicyclo[3.2.1]oct-2-ene, 3 (4 g, 12.3 mmol) in THF (43 mL) at −78° C. was added $SmI_2$ solution (0.1 M in THF, 400 mL, 40 mmol) dropwise. After 30 min at −78° C., MeOH (140 mL) was added and the resulting solution stirred at −78° C. for a further 1 h. The reaction was then quenched with TFA (28 mL) and water (285 mL), the cold bath was removed and the solution allowed to attain room temperature. The reaction was then made basic with $NH_4OH$ and diluted with ether and filtered through celite. The filter cake was washed with ether and all the organic phases were combined and washed with a sodium thiosulfate solution and then a brine solution. After drying with $Na_2SO_4$ the solution was filtered and concentrated and gave 3.8 g of the crude products. The title compounds 4 and 12 were isolated by column chromatography ($SiO_2$, 10 g; 2.5% EtOH in $CHCl_3$). Compound 12 was isolated as colorless crystals (1.15 g, 29%).

Mp. 89–91° C. $R_f$ 0.64 (1% $NH_4OH$/EtOAc). $^1$H-NMR ($CDCl_3$) δ 1.28 (ddd, J=1.6, 10.4, 14, 1H), 1.4–1.6 (m, 2H), 2.23 (s, 3H), 2.05–2.3 (m, 2H), 2.35–2.5 (m, 2H), 3.2–3.47 (m, 3H), 3.59 (s, 3H), 7.04 (dd, J=2.2, 8.2 Hz, 1H), 7.27 (d, J=2.2 Hz, 1H), 7.30 (d, J=8.2 Hz, 1H). Elemental analysis: calculated (0.1 $C_6H_{14}$) C, 59.18; H, 6.10; N, 4.16; Cl, 21.05. found C, 59.11; H, 5.90; N, 4.08; Cl, 21.01.

Compound 4 (R=3,4-$Cl_2$) (Meltzer et al., *J. Med. Chem.*, 1993, 36, 855–862) was isolated as a yellow solid (1.04 g, 26%).

Mp. 82.5–83.5° C. $R_f$ 0.43 (IPA/$Et_2O$/pentane; 3/30/67); $^1$H NMR (400 MHz, $CDCl_3$) δ 1.6–1.7 (m, 3H), 2.0–2.1 (m, 2H), 2.21 (s, 3H), 2.50 (ddd, 1H, H-4), 2.86(m, 1H), 2.92 (m, 1H), 3.33 (m, 1H, H-5), 3.52 (s, 3H), 3.55 (m, 1H), 7.07–7.32 (m, 3H). $[\alpha]_D^{21}$-27.0° (c=1, $CH_3OH$). Anal. ($C_{16}H_{19}NO_2Cl_2$) C, H, N, Cl.

EXAMPLE 4

(1R)-N-Methyl-2β-methoxycarbonyl-3β-(4-fluorophenyl)-8-azabicyclo[3.2.1]octane (Compound 4 (R=4-F), FIG. 2) and (1R)-N-Methyl-2β-methoxycarbonyl-3α-(4-fluorophenyl)-8-azabicyclo[3.2.1]octane (Compound 12 (R=4-F), FIG. 2; O-1204)

Using the same general procedure as described above for Example 3, except substituting (1R)-N-Methyl-2-methoxycarbonyl-3-(4-fluorophenyl)-8-azabicyclo[3.2.1]oct-2-ene, 3, compounds 4 and 12 (R=4=F) were obtained.

Compound 4 (R=4-F): white solid; Mp 93–94° C.;

$R_f$ 0.42 (i-Pr$NH_2$.$Et_2O$:pentane::5:30:65); $^1$H-NMR (400 MHz, $CDCl_3$) δ 1.57–1.75 (m, 3H), 2.0–2.2 (m, 2H), 2.23 (s, 3H), 2.54 (ddd, 1H), 2.84 (t, 1H), 2.95 (ddd 1H, J=5.3, 12.7 Hz), 3.36 (m, 1H), 3.50 (s, 3H), 3.55 (m, 1H), 6.9–7.25 (m, 4H). $[\alpha]_D^{21}$-45.6° (c=1, $CH_3OH$). Anal. ($C_{16}H_{20}NO_2F$) C, H, N.

Compound 12 (R=4-F): colorless oil;

$R_f$ 0.5 (10% MeOH in EtOAc); Elemental analysis: calculated C, 69.29; H, 7.27; N, 5.05. found C, 69.35; H, 7.26; N, 5.00. IR 2900, 1750, 1500 cm-1, $^1$H-NMR (100 MHz, $CDCl_3$) δ 1.1–1.8 (m, 4H), 1.9–2.6 (m, 3H), 2.25 (s, 3H), 3.1–3.7 (m, 3H), 3.59 (s, 3H), 6.8–7.3 (m, 4H).

EXAMPLE 5

2β-Carboxy-3β-(4-fluorophenyl)tropane (Compound 5 (R=4-F), FIG. 3)

2β-Methoxycarbonyl-3β-(4-fluorophenyl)tropane (WIN 35,428), 4 (1.25 g, 4.54 mmol) was refluxed for 24 h in a 1:1 dioxane-water (80 mL) solution. The solvent was removed in vacuo and the residue was almost completely dissolved in $CHCl_3$ (275 mL). Remaining undissolved solid was filtered off, toluene (30 mL) was added, and the solution was reduced in vacuo by approximately 75%. After cooling the resulting white suspension in the freezer for 2 h, the white solid was removed by filtration and was washed with cold 1:1 $CHCl_3$-toluene. The solid was pumped dry to yield the product 5 as a white solid (1.11 g, 95%).

$^1$H-NMR ($CDCl_3$) δ 1.7–1.8 (m, 1H), 1.94 (dd, J=9 Hz, 2H) 2.24–2.34 (m, 2H), 2.25 (m, 3H), 2.57 (ddd, J=13.7 Hz, 1H), 2.62–2.68 (m, 1H), 3.16 (ddd, J=13 Hz, 1H), 3.5–3.6 (m, 2H), 6.8 (m, 2H), 7.18–7.24 (m, 2H).

EXAMPLE 6

2β-Carboxy-3β-(3,4-dichlorophenyl)tropane (Compound 5 (R=3,4-$Cl_2$), FIG. 3)

2β-Methoxycarbonyl-3β-(3,4-dichlorophenyl)tropane, 4 (1.14 g, 3.47 mmol) was dissolved in THF:MeOH (1:1; 46 mL) to which was added a solution of $LiOH.H_2O$ (153 mg) in water (11 mL). The solution was heated to reflux for 24 h, cooled to 0° C. and neutralized (pH=7) with conc. HCl. Silica (1.75 g) was added directly to the solution and solvent was removed in vacuo. The material was purified by flash chromatography column (eluent 20% MeOH/$CHCl_3$ (900 mL) followed by 30% MeOH/$CHCl_3$ (2 L)). Fractions containing the product were collected and combined, evaporated in vacuo and the residue was dried at high vacuum. The product was obtained (310 mg; 28%).

$R_f$ 0.08 (30% MeOH/$CHCl_3$); $^1$H-NMR ($CDCl_3$) δ 1.8–1.9 (m, 1H), 2.1–2.2 (m, 2H) 2.3–2.5 (m, 2H), 2.6–2.9 (m, 2H), 2.78 (s, 3H), 3.3–3.4 (m, 1H), 3.93 (m, 2H), 7.25 (dd, J=8.2 Hz, 2.2 Hz, 1H), 7.41 (d, J=8.2 Hz, 1H), 7.48 (d, J=2.2 Hz, 1H).

EXAMPLE 7

2β-Methoxymethylcarbamoyl-3β-(4-fluorophenyl)tropane (Compound 6 (R=4-F), FIG. 3)

To a stirred suspension of the acid 5 (1.1 g) in anhydrous $CH_2Cl_2$ (80 mL) containing DMF (50 μL) was added oxalyl chloride (1 mL, 11.4 mmol) dropwise resulting in copious bubbling and dissolution of the suspension. The reaction was allowed to stir for 45 min during which time the solution became yellow. The solution was then reduced in vacuo and pumped at high vacuum overnight, care being taken to bleed nitrogen into the evacuated flask when transferring from the rotary to the pump.

To the acid chloride dissolved in $CH_2Cl_2$ (80 mL) was added (MeO)MeNH HCl (450 mg; dried immediately prior to use over $P_2O_5$ under high vacuum followed immediately by pyridine (1.1 mL). The reaction was allowed to stir for 1 h and was partitioned across $CHCl_3$ (20 mL) and 2M $Na_2CO_3$ (20 mL). The aqueous layer was extracted $CHCl_3$ (2×10 mL) and the combined organic extracts were dried over $Na_2SO_4$, filtered and reduced in vacuo to yield 1.09 g of a yellow solid. The crude product was dissolved in $CH_2Cl_2$ and purified by flash chromatography ($SiO_2$, 43 g; 20% hexanes/EtOAc, 5% $Et_3N$). Product containing fractions were combined and concentrated to yield a light yellow solid 6 (960 mg; 75%).

Mp. 120.1–122.5° C.; $R_f$ 0.14 (25% hexanes/EtOAc, 5% TEA); Elemental analysis: calculated C, 66.65; H, 7.57; N, 9.14. found C, 66.78; H, 7.63; N, 9.01. IR (KBr) 2900, 1680, 1500 cm$^{-1}$; $^1$H-NMR ($CDCl_3$) δ 1.5–1.8 (m, 3H), 2.0–2.3 (m, 2H), 2.24 (m, 3H), 2.79 (ddd, 1H), 3.0 (m, 1H), 3.05 (s, 3H), 3.1 (m, 1H), 3.4 (m, 1H), 3.47 (m, 1H), 3.57 (s, 3H), 6.9 (m, 2H), 7.25 (m, 2H).

EXAMPLE 8

2β-Methoxymethylcarbamoyl-3β-(3,4-dichlorophenyl)tropane (Compound 6 (R=3,4-$Cl_2$), FIG. 3)

To a stirred solution of 2β-carboxy-3β-(3,4-dichlorophenyl)tropane, 5 (300 mg, 9.55 mmol) in anh. $CH_2Cl_2$ (30 mL) was added anh. DMF (40 μL) and oxalyl chloride (450 μL) dropwise. The solution was stirred at room temperature for 40 min. The solvent was removed in vacuo and the residue dried at high vacuum overnight.

To the dry residue was added methoxy methylamine hydrochloride (103 mg, 1.05 mmol). The flask was flushed with nitrogen and $CH_2Cl_2$ (30 mL) was added by cannula followed immediately by pyridine (400 μL). The reaction was stirred for 2.5 h. The resultant mixture was partitioned between $CH_2C_2$ (40 mL) and 1M $Na_2CO_3$ (25 mL). The aqueous layer was extracted with $CHCl_3$ and the combined organic extracts were dried and concentrated to yield a yellow solid (298 mg). The solid was purified on a chromatography column (eluent 50% EtOAc/hexane/5% $Et_3N$). Like fractions were combined, solvent removed and the product dried at high vacuum to yield Compound 6 (39 mg; 11%).

$R_f$ 0.1 (50% EtOAc/hexane/5% $Et_3N$); $^1$H-NMR ($CDCl_3$) δ 1.5–1.74 (m, 3H), 2.0–2.3 (m, 2H), 2.21 (m, 3H), 2.72 (ddd, 1H), 2.93 (m, 1H), 3.04 (s, 3H), 3.13 (m, 1H), 3.38 (m, 1H), 3.5 (m, 1H), 3.62 (s, 3H), 7.13 (dd, 1H), 7.30 (d, 1H), 7.31 (d, 1H).

EXAMPLE 9

2β-(1-Propanoyl)-3β-(4-fluorophenyl)tropane (Compound 7 (R=4-F), FIG. 3)

A solution of 2β-(N-methoxy-N-methylcarbamoyl)-3β-(4-fluorophenyl)-tropane, 6 (823 mg, 2.7 mmol) in THF (10 mL) was cooled to 0° C. and $EtMgBr/Et_2O$ (3M; 3 mL) was added dropwise over 4 min. The reaction was warmed to room temperature for 30 min and then heated to 65° C. for 45 min. The mixture was cooled to 0° C. and quenched by addition of ethereal HCl (3M). The resulting cloudy solution was basified with 2M $Na_2CO_3$. Ether (5 mL) was added and the layers separated and the aqueous layer washed with $Et_2O$ (1×10 mL) and $CHCl_3$ (2×10 mL). The combined organic extracts were dried over $Na_2SO_4$, filtered and concentrated. The product was purified by flash column chromatography (eluent 25% EtOAc/hexanes/5% TEA) to provide 7 (485 mg, 65%).

$R_f$ 0.3 (20% EtOAc/hexanes/5% $Et_3N$); mp 118–119.5° C.; Elemental analysis: calculated C, 74.15; H, 8.05; N, 5.09. found C, 74.05; H, 8.09; N, 5.00. IR (KBr) 2900, 1710, 1500. 1250 $cm^{-1}$; $^1$H-NMR ($CDCl_3$) δ 0.85 (t, 3H), 1.5–1.8 (m, 4H), 2.0–2.4 (m, 3H), 2.23 (m, 3H), 2.5–2.6 (m, 1H), 2.9–3.0 (m, 2H), 3.36 (m, 1H), 3.48 (m, 1H), 6.69 (m, 2H), 7.17 (m, 2H).

EXAMPLE 10

2β-(1-Propanoyl)-3β-(3,4-dichlorophenyl)tropane (Compound 7 (R=3,4-$Cl_2$), FIG. 3)

A solution of 2β-methoxymethylcarbamoyl-3β-(3,4-dichlorophenyl), 6 (168 mg, 0.47 mmol) in THF (30 mL) was cooled to 0° C. and $EtMgBr/Et_2O$ (3M; 1 mL) was added dropwise over 3 min. The reaction was warmed to room temperature for 60 min and then heated to reflux for 10 min. The mixture was cooled to room temperature and quenched by addition to ethereal HCl (3M, 20 mL). The resulting cloudy solution was basified with saturated aqueous $NaHCO_3$ and brought to pH=10 by addition of $Na_2CO_3$. Ether was added and the layers separated and the aqueous layer washed with $Et_2O$ (3×25 mL). The combined organic extracts were dried over $Na_2SO_4$, filtered and concentrated. The product (166 mg) was purified by flash column chromatography (eluent 30% EtOAc/hexanes/5% $Et_3N$) to provide 7 (108 mg, 71%).

$R_f$ 0.32 (50% EtOAc/hexanes/5% $Et_3N$); $^1$H-NMR ($CDCl_3$) δ 0.9 (t, 3H), 1.5–1.8 (m, 4H), 2.0–2.3 (m, 3H), 2.2 (m, 3H), 2.35–2.55 (m, 2H), 2.82–2.92 (m, 1H), 2.96 (m, 1H), 3.34 (m, 1H), 3.54 (m, 1H), 7.75 (dd, 1H), 7.27 (d, 1H), 7.29 (d, 1H).

EXAMPLE 11

2β-(1-Propanoyl)-3β-(4-fluorophenyl)nortropane (Compound 8 (R=4-F), FIG. 3)

2β-(1-Propanoyl)-3β-(4-fluorophenyl)tropane, 7 (335 mg) was combined with 1-chloroethyl chloroformate (5 mL) and the solution was heated to reflux for 5 h. The excess chloroformate was removed in vacuo and the residue was refluxed in methanol for 1.5 h. The methanol was removed in vacuo and the residue was dissolved in $CHCl_3$ (15 mL) and shaken with 2M $Na_2CO_3$. The aqueous layer was extracted $CHCl_3$ (2×15 mL) and the combined organic extracts were dried ($Na_2SO_4$), filtered and concentrated to yield 369 mg. This residue was chromatographed (eluent: 100 mL EtOAc, 150 mL 5% $Et_3N$/EtOAc, 100 mL 10% $Et_3N$/EtOAc, 300 mL 20% $Et_3N$/EtOAc, and 300 mL 30% $Et_3N$/EtOAc). Like fractions were combined to yield 8 (104 mg, 33%).

$R_f$ 0.36 (10% $Et_3N$/EtOAc); $^1$H-NMR ($CDCl_3$) δ 0.70 (t, 3H), 1.4–1.8 (m, 5H), 1.9–2.3 (m, 3H), 2.4 (m, 1H), 2.88 (m, 1H), 3.18 (m, 1H), 3.56 (m, 1H), 3.70 (m, 1H), 6.94 (m, 2H), 7.10 (m, 2H).

EXAMPLE 12

2β-(1-Propanoyl)-3β-(3,4-dichlorophenyl)nortropane (Compound 8 (R=3,4-$Cl_2$), FIG. 3)

2β-(1-Propanoyl)-3β-(3,4-dichlorophenyl)tropane 7 (107 mg, 0.32 mmol) was combined with 1-chloroethyl chloroformate (2 mL) and the solution was heated to reflux for 5 h. The excess chloroformate was removed in vacuo and the residue was refluxed in methanol for 45 min. The methanol was removed in vacuo and the residue was dissolved in $CH_2Cl_2$ and shaken with $NaHCO_3/Na_2CO_3$ (pH=9). The aqueous layer was extracted $CH_2Cl_2$ (4×10 mL) and the combined organic extracts were dried ($Na_2SO_4$), filtered and concentrated to yield 127 mg. This residue was chromatographed (1×100 mL 5% $Et_3N$/EtOAc; 3×100 mL 10% $Et_3N$/EtOAc). Like fractions were combined to yield 8 (30 mg, 29%).

$^1$H-NMR ($CDCl_3$) δ 0.76 (t, 3H), 1.4–2.5 (m, 9H), 2.92 (m, 1H), 3.09–3.2 (m, 1H), 3.6 (m, 1H), 3.72 (m, 1H), 7.0 (m, 1H), 7.25 (d, 1H), 7.32 (d, 1H).

EXAMPLE 13

N-[2-(3'-N'-Propyl-(1"R)-3"β-(4-fluorophenyl)tropane-2"β-(1-propanoyl))((2-((triphenylmethyl)thio)ethyl)amino)acetyl]-S-(triphenyl)-2-aminoethanethiol (Compound 9 (R=4-F), FIG. 3) (O-1507)

2β-(1-Propanoyl)-3β-(4-fluorophenyl)nortropane 8 (27 mg) was combined with MAMA'-Cl (86 mg), KI (34 mg, 2.0 eq.), and NaHCO$_3$ (43 mg, 5 eq.) in anhydrous MeCN (4 mL) and brought to reflux for 4 h. The solvent was removed under vacuum and the residue was partitioned between CHCl$_3$ and saturated aqueous NaHCO$_3$. The aqueous layer was extracted CHCl$_3$ (2×5 mL) and the combined organic extracts were dried (Na$_2$SO$_4$), filtered and concentrated to yield a brown foam. The foam was applied to a chromatography column (10 g silica; 40% EtOAc in hexanes/1% TEA). Fractions containing the product were combined and concentrated to yield 9 as a light foam (47 mg, 46%).

$R_f$ 0.09 (60% EtOAc/hexanes, 1% Et$_3$N). Elemental analysis: calculated C, 72.15; H, 6.34; N, 3.96. found C, 71.99; H, 6.41; N, 3.92. $^1$H-NMR (CDCl$_3$) δ 0.77 (t, 3H), 1.2–3.1 (m, 29H), 3.3–3.5 (m, 2H), 6.9–7.0 (m, 2H), 7.1–7.6 (m, 32H).

EXAMPLE 14

N-[2-(3'-N'-Propyl-(1"R)-3"β-(3,4-dichlorophenyl)tropane-2"β-(1-propanoyl))((2-((triphenylmethyl)thio)ethyl)amino)acetyl]-S-(triphenyl)-2-aminoethanethiol (Compound 9 (R=3,4-Cl$_2$), FIG. 3)

2μ-(1-Propanoyl)-3β-(3,4-dichlorophenyl)nortropane 8 (30 mg, 0.096 mmol) was combined with MAMA'-Cl (87 mg, 0.115 mmol, 1.2 eq.), KI (32 mg, 0.19 mmol, 2.0 eq.), and NaHCO$_3$ (40 mg, 0.48 mmol, 5 eq.) in anhydrous MeCN (4 mL) and brought to reflux for 4 h then cooled to room temperature and allowed to stir overnight. The solvent was removed under vacuum and the residue was partitioned between CH$_2$Cl$_2$ (15 mL) and saturated aqueous NaHCO$_3$ (15 mL). The aqueous layer was extracted with CH$_2$Cl$_2$ (3×10 mL) and the combined organic extracts were dried (Na$_2$SO$_4$), filtered and concentrated to yield a yellow oil (115 mg). The oil was applied to a chromatography column (10 g SiO$_2$; 30% EtOAc in hexanes/1% Et$_3$N). Fractions containing the product were combined and concentrated to yield 9 as a light foam (41 mg, 41%).

$R_f$ 0.14 (60% EtOAc/hexanes, 1% Et$_3$N). $^1$H-NMR (CDCl$_3$) δ 0.81 (t, 3H), 1.2–3.1 (m, 29H), 3.34 (m, 1H), 3.52 (m, 1H), 7.0–7.6 (m, 33H).

EXAMPLE 15

N-[(2-((3'-N'-Propyl-(1"R)-3"β-(4-fluorophenyl)tropane-2"β-1-propanoyl)(2-mercaptoethyl) amino)acetyl)-2-aminoethane-thiolato]rhenium (V) oxide (Compound 10 (R=4-F), FIG. 3) (O-1508R)

N-[2-(3'-N'-Propyl-(1"R)-3"β-(4-fluorophenyl)tropane-2"β-(1-propanoyl))((2-((triphenylmethyl)thio)ethyl)amino)acetyl]-S-(triphenyl)-2-aminoethanethiol (22 mg, 0.023 mmol) was dissolved in boiling EtOH (abs. 4 mL) and SnCl$_2$ (8.5 mg, in 0.5 mL of 0.05M HCl). The reaction was maintained at reflux for a further 6 h and silica was added and the solvents removed by evaporation. The silica adsorbed product was applied to a silica column (3 g eluent: 30% EtOAc in hexanes with 5% Et$_3$N). The compound was obtained as a foam (6.7 mg, 44%).

$R_f$ 0.07 (60% EtOAc in hexanes+NH$_4$OH (0.5%)) Accurate Mass calc for C$_{25}$H$_{35}$FN$_3$O$_3$ReS$_2$: 695.172. found 695.162. $^1$H-NMR (CDCl$_3$) δ 0.7–0.9 (2t, 2H), 1.4–4.1 (m, 26H), 4.5–4.6 (m, 1H), 4.73 (d, J=16.5 Hz, 0.5H) 4.87 (d, J=16.5 Hz, 0.5H), 6.93 (m, 2H), 7.14 (m, 2H).

EXAMPLE 16

2β-(Carboxylic acid)-3α-(4-fluorophenyl)tropane (Compound 13 (R=4-F), FIG. 4)

A solution of 2β-methoxycarbonyl-3α-(4-fluorophenyl)-tropane 12 (1.0 g, 3.6 mmol) was refluxed for 24 h in 80 mL dioxane water (1:1). The solvent was removed in vacuo and the brown solid was purified by column chromatography (eluent 30% MeOH/CHCl$_3$). The product (890 mg, 94%) was obtained as a white foam.

$R_f$ 0.43 (30% MeOH/CHCl$_3$); NMR $^1$H-NMR (CDCl$_3$) δ 1.48–1.62 (m, 1H), 1.75–2.1 (m, 3H), 2.36–2.46 (m, 1H), 2.60 (s, 3H), 2.7–2.82 (m, 1H), 3.22 (brs, 1H), 3.5–3.62 (m, 2H), 3.76–3.84 (m, 1H), 6.9–7.1 (m, 2H), 7.4–7.5 (m, 2H).

EXAMPLE 17

2β-(Carboxylic acid)-3α-(3,4-dichlorophenyl)tropane (Compound 13 (R=3,4-Cl$_2$), FIG. 4)

A solution of 2β-methoxycarbonyl-3α-(3,4-dichlorophenyl)tropane 12 (750 mg, 2.29 mmol) and LiOH (335 mg, 8.0 mmol) was brought to reflux for 4 h in water (10 mL) and THF:MeOH (33 mL; 1:1). The reaction was neutralized by dropwise addition of conc. HCl. The solvent was removed in vacuo and the product purified by column chromatography (eluent 15% MeOH/CHCl$_3$). The product 13 (521 mg, 72%) was obtained as a solid.

$R_f$ 0.15 (30% MeOH/CHCl$_3$); $^1$H-NMR (CD$_3$OD) δ 1.59 (m, 1H), 1.8–1.9 (m, 1H), 2.1–2.2 (m, 2H), 2.6–2.7 (m, 2H), 2.76 (s, 3H), 3.25 (brs, 1H), 3.35 (brs, 1H), 3.85 (m, 1H), 3.93 (m, 1H), 7.5 (d, 1H), 7.53 (dd, 1H), 7.8 (d, 1H).

EXAMPLE 18

2β-Methoxymethylcarbamoyl-3α-(4-fluorophenyl)tropane (Compound 14 (R=4-F), FIG. 4) (O-1403)

To a stirred suspension of Compound 13 (930 mg, 3.6 mmol) in anhydrous CH$_2$Cl$_2$ (80 mL) containing DMF (50 μL) was added oxalyl chloride (1 mL, 11.4 mmol) dropwise resulting in copious bubbling and dissolution of the suspension. The reaction was allowed to stir for 45 min during which time the solution became yellow. It was then reduced in vacuo and pumped at high vacuum overnight, care being taken to bleed nitrogen into the evacuated flask when transferring from the rotary to the pump.

To the acid chloride dissolved in CH$_2$Cl$_2$ (70 mL) was added (MeO)MeNH.HCl (382 mg, 3.9 mmol) followed immediately by pyridine (1 mL). The reaction was allowed to stir for 1 h and then partitioned between CHCl$_3$ (20 mL) and 2M Na$_2$CO$_3$ (20 mL). The aqueous layer was extracted with CHCl$_3$ (2×10 mL) and the combined organic extracts were dried over Na$_2$SO$_4$, filtered and reduced in vacuo to yield a yellow oil. The oil was dissolved in toluene and concentrated to yield a yellow solid (653 mg). The crude product was dissolved in a minimum volume of CHCl$_3$, and applied to a chromatography column (28 g SiO$_2$; eluent 25% hexanes in EtOAc, 5% Et$_3$N; followed by 25% MeOH in CHCl$_3$). Product containing fractions were combined and concentrated to yield the amide (540 mg; 50%).

R$_f$ 0.25 (25% hexanes/EtOAc, 5% Et$_3$N); mp. 139.8–141.7° C.; $^1$H-NMR (CDCl$_3$) δ 1.24 (dd, 1H), 1.4–1.8 (m, 3H), 2.1–2.3 (m, 2H), 2.23 (s, 3H), 2.4–2.6 (m, 1H), 2.7 (brd, 1H), 3.05 (s, 3H), 3.05–3.1 (m, 1H), 3.25–3.5 (m, 2H), 3.41 (s, 3H), 6.86–6.96 (m, 2H), 7.13–7.22 (m, 2H); IR (KBr) 2900, 1656, 1500 cm$^{-1}$. Elemental analysis: calculated C, 66.65; H, 7.57; N, 9.14. found C, 66.37; H, 7.59; N, 9.0.

EXAMPLE 19

2β-Methoxymethylcarbamoyl-3α-(3,4-dichlorophenyl)tropane (Compound 14 (R=3,4-Cl$_2$), FIG. 4)

To a stirred suspension of the acid 13 (210 mg, 0.67 mmol) in anhydrous CH$_2$Cl$_2$ (10 mL) containing DMF (30 μL) was added oxalyl chloride (0.3 mL, 2.0 mmol) dropwise. The reaction was allowed to stir for 1 h and then reduced in vacuo and pumped at high vacuum overnight, care being taken to bleed nitrogen into the evacuated flask when transferring from the rotary to the pump.

To the acid chloride in CH$_2$Cl$_2$ (10 mL) was added (MeO)MeNH. HCl (72 mg, 0.74 mmol) followed immediately by pyridine (0.3 mL). The reaction was allowed to stir for 1.5 h and was partitioned between CH$_2$Cl$_2$ (10 mL) and 1M Na$_2$CO$_3$ solution (5 mL). The aqueous layer was extracted with CH$_2$Cl$_2$ (10 mL) and the combined organic extracts were dried over Na$_2$SO$_4$, filtered and reduced in vacuo to yield a yellow solid. The solid was purified by column chromatography (14 g SiO2, eluent 25% hexanes/EtOAc, 5% Et$_3$N). Product containing fractions were combined and concentrated to yield the amide (115 mg; 48%).

R$_f$ 0.14 (40% hexanes/EtOAc, 5% Et$_3$N); $^1$H-NMR (CDCl$_3$) δ 1.17 (ddd, 1H), 1.48 (ddd, 1H), 1.63 (ddd, 1H), 2.1–2.34 (m, 2H), 2.21 (s, 3H), 2.42–2.54 (m, 1H), 2.65 (brd, 1H), 3.06 (s, 3H), 3.08 (brs, 1H), 3.22–3.32 (m, 1H), 3.34–3.46 (m, 1H), 3.48 (s, 3H), 7.05 (dd, 1H), 7.25 (d, 1H), 7.27 (d, 1H).

EXAMPLE 20

2β-(1-Propanoyl)-3α-(4-fluorophenyl)-tropane (Compound 15 (R=4-F), FIG. 4) (O-1369)

A 250 mL round bottom flask containing the 2β-methoxymethylcarbamoyl-3α-(4-fluorophenyl)tropane 14 (471 mg) was flushed with nitrogen and charged with anhydrous THF (70 mL). At room temperature, EtMgBr/Et$_2$O (3.0 mL; 3.0M) was added dropwise over 3 min. The reaction was stirred at room temperature for 30 min and was then heated to 65° C. for 1 h at which point no starting material was observed by TLC (TLC sample was prepared by adding an aliquot of the reaction to ethereal HCl, and basifying with 2M Na$_2$CO$_3$; R$_f$ (product) 0.42; R$_f$ (starting material) 0.13 (20% EtOAc/hexanes, 5% Et$_3$N). The reaction was cooled in an ice bath and quenched by slow addition of ethereal HCl. The cloudy solution was basified with 2M Na$_2$CO$_3$ and diluted with ether (25 mL). The layers were separated and the aqueous layer was extracted with ether (1×10 mL) and CHCl$_3$ (2×20 mL). The combined organic extracts were dried (Na$_2$SO$_4$), filtered and reduced in vacuo to yield the crude residue (484 mg). This residue was then chromatographed (25 g SiO2; eluent 25% EtOAc/hexanes, 5% Et$_3$N).

Fractions containing the product were combined and concentrated to yield 15 (300 mg, 70%);

Mp. 60.5–61.3° C.; R$_f$ 0.49 (33% EtOAc/hexanes; 5% Et$_3$N); $^1$H-NMR (CDCl$_3$) δ 0.86 (t, 3H), 1.27 (ddd, 1H), 1.4–1.6 (m, 2H), 2.0–2.5 (m, 6H), 2.23 (s, 3H), 3.12 (brd, 1H), 3.2–3.3 (m, 2H), 6.85–7.0 (m, 2H), 7.05–7.15 (m, 2H); IR (KBr) 2900, 1740, 1500 cm$^{-1}$; Elemental analysis: calculated C, 74.15; H, 8.05; N, 5.09. found C, 74.00; H, 8.13; N, 4.98.

EXAMPLE 21

2β-(1-Propanoyl)-3α-(3,4-dichlorophenyl)tropane (Compound 15 (R=3,4-Cl$_2$), FIG. 4)

2β-Methoxymethylcarbamoyl-3α-(3,4-dichlorophenyl)tropane, 14 (105 mg, 0.29 mmol) was flushed with nitrogen and charged with anhydrous THF (15 mL). At room temperature, EtMgBr/Et$_2$O (0.8 mL; 3.0M) was added dropwise over 3 min. The reaction was stirred at room temperature for 1 h and was then heated to 55° C. for 30 min at which point no starting material was observed by TLC. The reaction was cooled in an ice bath and quenched by slow addition of ethereal HCl. The cloudy solution was basified with 2M Na$_2$CO$_3$ and diluted with ether (15 mL) and water (15 mL). The layers were separated and the aqueous layer was extracted with CHCl$_3$ (2×15 mL). The combined organic extracts were dried (Na$_2$SO$_4$), filtered and reduced in vacuo to yield a residue (95 mg) which was chromatographed (5 g SiO$_2$, eluent 25% EtOAc in hexanes, 5% Et$_3$N). Fractions containing the product were combined and concentrated to yield 15 (80 mg, 80%).

R$_f$ 0.28 (30% EtOAc/hexanes; 5% Et$_3$N); $^1$H-NMR (CDCl$_3$) 0.93 (t, J=7.4 Hz, 3H), 1.27 (ddd, 1H), 1.42–1.62 (m, 2H), 2.06–2.30 (m, 6H), 2.21 (s, 3H), 3.32–2.52 (m, 3H), 3.14 (brd 1H), 3.2–3.36 (m, 2H), 7.10 (dd, 1H), 7.24 (d, 1H), 7.29 (d, 1H).

EXAMPLE 21a

2β-(1-Propanoyl)-3α-(3,4-dichlorophenyl)tropane (Compound 15 (R-3,4-Cl$_2$), FIG. 4)

To commercially available ethylmagnesium bromide (1M in THF, 12.6 mL, 12.6 mmol) in a flask equipped with an addition funnel under nitrogen was added triethylamine (5.0 g, 50.4 mmol). To the resulting mixture was added dropwise a solution of compound 12 (R=Cl$_2$, 750 mg, 2.29 mmol) in benzene (10 mL) at 5–10° C. over a period of 1 hour. The reaction mixture was then stirred at 5–10° C. for 5 hours and then treated with 4 M HCl (2.9 mL, 11.6 mmol). The organic layer was washed with water (1×50 mL), 5% NaHCO$_3$ (aq) (1×50 mL) and water (2×50 mL). The organic phase was then dried (K$_2$CO$_3$), filtered and the concentrated. The residue was chromatographed (SiO$_2$.25% EtOAc in hexanes with 5% Et$_3$N) and gave 670 mg (85%) of compound 15 with the same physical and spectral characteristics as previously reported (Example 21).

EXAMPLE 22

2β-(1-Propanoyl)-3α-(4-fluorophenyl)nortropane (Compound 16 (R=4-F), FIG. 4) (O-1370)

2β-(1-Propanoyl)-3α-(4-fluorophenyl)tropane 15 (O-1369) (556 mg, 2 mmol) and ACE-Cl (7 mL) were combined and brought to reflux for 4 h. All volatiles were removed by evaporation and methanol (100 mL) was added to the residue. The resulting mixture was brought to reflux for 90 min. Volatiles were removed and the residue was taken up in CHCl$_3$ and washed with aq. 2M Na$_2$CO$_3$. The aqueous mixture was extracted with CHCl$_3$ (2×10 mL) and organic fractions combined, dried (Na$_2$SO$_4$), filtered and reduced. The dark brown oil (615 mg) was chromatographed (SiO$_2$, 20 g; 0–10% Et3N in EtOAc) and gave 390 mg (74%) of a yellow oil.

R$_f$ 0.25 (5% Et$_3$N in EtOAc); $^1$H-NMR (CDCl$_3$) δ 0.86 (t, 3H), 1.27 (ddd, 1H), 1.50–1.72 (m, 2H), 1.8–2.1 (m, 3H), 2.2–2.4 (m, 2H), 2.56 (dd, J=10.7, 1 Hz, 1H), 3.07 (ddd, J=11.3, 10.9, 7.1 Hz, 1H), 3.43 (brd 1H), 3.62 (brt, 1H), 6.89–6.99 (m, 2H), 7.09–7.16 (m, 2H). IR (KBr) 2900, 1711, 1500 cm$^{-1}$; Elemental analysis: calculated (0.2H$_2$O) C, 72.52; H, 7.77; N, 5.25. found C, 72.65; H, 7.81; N, 5.27.

EXAMPLE 23

2β-(1-Propanoyl)-3α-(3,4-dichlorophenyl)nortropane (Compound 16 (R=3,4-Cl$_2$), FIG. 4)

2β-(1-Propanoyl)-3-(3,4-dichlorophenyl)tropane, 15 (80 mg, 2.45 mmol) was combined with 1-chloroethyl chloroformate (3 mL) and the solution was heated to reflux for 5 h. The excess chloroformate was removed in vacuo and the residue was refluxed in methanol for 1 h. The methanol was removed in vacuo and the residue was dissolved in CHCl$_3$ and washed with 2M Na$_2$CO$_3$. The aqueous layer was extracted with CHCl$_3$ (2×5 mL) and the combined organic extracts were dried (Na$_2$SO$_4$), filtered and concentrated to yield pure compound (77 mg; 100%).

R$_f$ 0.3 (5% Et$_3$N/EtOAc); $^1$H-NMR (CDCl$_3$) δ 0.91 (t, 3H), 1.25 (ddd, 1H, 1.52–1.74 (m, 2H), 1.8–2.56 (m, 7H), 3.06–3.2 (m, 1H), 3.45 (d, 1H), 3.62 (brt, 1H), 7.01 (dd, 1H), 7.25 (d, 1H), 7.31 (d, 1H).

EXAMPLE 24

N-[2-(3'-N'-Propyl-(1"R)-3"α-(4-fluorophenyl)tropane-2"β-(1-propanoyl))((2-((triphenylmethyl)thio)ethyl)amino)acetyl]-S-(triphenyl)-2-aminoethanethiol (compound 17 (R=4-F), FIG. 4) (O-1506)

2β-(1-Propanoyl)-3α-(4-fluorophenyl)nortropane 16 (24 mg, 0.09 mmol), MAMA'-Cl (147 mg, 0.19 mmol), KI (31 mg, 19 mmol) were all dissolved in CH$_3$CN (3 mL) and brought to reflux for 3 h. Solvent was removed in vacuo and the residue partitioned between satd. aq NaHCO$_3$ and CHCl$_3$. The aqueous layer was further extracted with CHCl$_3$, all organic fractions were combined and dried (Na$_2$SO$_4$), filtered and concentrated. Column chromatography (20% EtOAc, 79% Hexane, 1% Et$_3$N) gave pure product as a golden foam (11.5 mg, 13%).

R$_f$ 0.15 (50% EtOAc in hexanes+5% Et$_3$N); Elemental analysis: calculated (0.1H$_2$O) C, 75.79; H, 6.87; N, 4.21. found C, 75.35; H, 6.81; N, 4.13. $^1$H-NMR (CDCl$_3$) δ 0.85 (t, 3H), 1.19 (ddd, 1H), 1.3–1.5 (m, 6H), 1.8–2.6 (m, 14H), 2.85 (brs, 2H), 3.0 (m, 2H), 3.08–3.30 (m, 3H), 6.88–6.96 (m, 2H), 7.06–7.42 (m, 32H).

EXAMPLE 25

N-[2-(3'-N'-Propyl-(1"R)-3"α-(3,4-dichlorophenyl)tropane-2"β-(1'''-propanoyl))((2-((triphenylmethyl)thio)ethyl)amino)acetyl]-S-(triphenyl)-2-aminoethanethiol (Compound 17 (R=3,4-Cl$_2$), FIG. 4) (O-1546)

2β-(1-Propanoyl)-3α-(3,4-dichlorophenyl)nortropane 16 (75 mg, 0.24 mmol) was combined with N-(((2-(2-(triphenylmethyl)thio)ethyl)(N'-3'-chloropropyl)amino)-acetyl)-S-(triphenylmethyl)-2-aminoethanethiol (MAMA'-Cl) (218 mg, 0.29 mmol), KI (80 mg, 0.48 mmol), and NaHCO$_3$ (101 mg, 1.2 mmol) in anhydrous MeCN (20 mL) and brought to reflux for 4 h then cooled to room temperature. The solvent was removed under vacuum and the residue was partitioned between CH$_2$Cl$_2$ (20 mL) and saturated aqueous NaHCO$_3$ (15 mL). The aqueous layer was extracted with CH$_2$Cl$_2$ (1×10 mL) and the combined organic extracts were dried (Na$_2$SO$_4$), filtered and concentrated to yield a brown oil. The oil was applied to a chromatography column (30 g SiO$_2$; eluent: 25% EtOAc/hexanes/1% Et$_3$N). Fractions containing the product were combined and concentrated to yield 17 (51 mg, 17%).

R$_f$ 0.3 (60% EtOAc in hexanes, 1% Et$_3$N); Elemental analysis: calculated (1.33 H$_2$O) C, 71.71; H, 6.46; N, 3.98. found C, 71.85; H, 6.52; N, 3.91. $^1$H-NMR (CDCl$_3$) δ 0.89 (t, 3H), 1.0–1.7 (m, 8H), 1.8–2.5 (m, 14H), 2.6–3.4 (m, 6H), 6.9–7.6 (m, 33H).

EXAMPLE 26

N-[(2-((3'-N'-Propyl-(1"R)-3"α-(4-fluorophenyl)tropane-2"β-1'''-propanoyl)(2-mercaptoethyl)amino)acetyl)-2-aminoethane-thiolato]rhenium (V) oxide (Compound 18 (R=4-F), FIG. 4) (O-1505)

A solution of N-[2-(3'-N'-Propyl-(1"R)-3"α-(4-fluorophenyl)tropane-2"β-(1'''-propanoyl))((2-((triphenylmethyl)thio)ethyl)amino)acetyl]-S-(triphenyl)-2-aminoethanethiol, 17 (22 mg) in EtOH (4 mL) was heated to reflux. A solution of SnCl$_2$ (7.8 mg, 0.04 mmol) in 0.005 M HCl (0.5 mL) was added quickly followed immediately by NaReO$_4$ (12.4 mg, 0.04 mmol) in 0.005 M HCl (0.5 mL). The cloudy solution was refluxed for 6 h and was then loaded onto 0.5 g silica and pumped overnight. The silica-adsorbed material was applied to a chromatography column (3 g SiO$_2$; eluent 30% EtOAc/hexanes/5% TEA). The purple brown solid obtained was triturated with pentane and dried at high vacuum overnight to yield 18 as a foam (9.9 mg; 71%).

Accurate Mass calc 695.161 (found, 695.172). R$_f$ 0.30 (75% EtOAc in hexane +0.5% NH$_4$OH); $^1$H-NMR (CDCl$_3$) δ 0.75–0.95 (2t, 3H), 1.0–2.0 (m, 8H), 2.0–2.5 (m, 6H), 2.8–3.0 (m, 1H), 3.0–3.5 (m, 7H), 3.6–3.8 (m, 1H), 3.9–4.2 (m, 3H), 4.5–4.65 (m, 1H), 4.73, 5.12 (2d, J=16.7 Hz), 6.9–7.0 (m, 2H), 7.08–7.15 (m, 2H).

EXAMPLE 27

N-[(2-((3'-N'-Propyl-(1"R)-3"α-(3,4-dichlorophenyl)tropane-2"β-1'''-propanoyl)(2-mercaptoethyl)amino)acetyl)-2-aminoethane-thiolato]rhenium (V) oxide (Compound 18 (R=3,4-Cl$_2$), FIG. 4)

A solution of N-[2-(3'-N'-Propyl-(1"R)-3"α-(3,4-dichlorophenyl)tropane-2"β-(1-propanoyl))(2-((triphenylmethyl)thio)ethyl)amino)acetyl]-S-(triphenyl)-2-aminoethanethiol, 17, (24 mg, 0.024 mmol) in EtOH (5 mL) was heated to reflux. A solution of $SnCl_2$ (9 mg, 0.05 mmol) in 0.005 M HCl (0.5 mL) was added quickly followed immediately by $NaReO_4$ (14.5 mg, 0.05 mmol) in 0.005 M HCl (0.5 mL). The solution was refluxed for 4 h and was then loaded onto 0.5 g silica and pumped at high vacuum overnight. The silica-adsorbed material was applied to a chromatography column (4 g $SiO_2$; eluent 30% EtOAc/hexanes/5% $Et_3N$). The solid obtained was concentrated to yield 18 (4.6 mg; 27%).

$^1$H-NMR ($CDCl_3$) δ 0.8–1.0 (2t, 3H), 1.1–2.5 (m, 14H), 2.8–3.0 (m, 1H), 3.0–3.5 (m, 7H), 3.6–3.8 (m, 1H), 3.9–4.2 (m, 3H), 4.4–4.65 (m, 1H), 4.70, 5.06 (2d, 2×J=16.7 Hz, 1H), 7.0 (dd, 1H), 7.3 (d, 1H), 7.34 (d, 1H).

EXAMPLE 28

2β-(Methoxymethylcarbamoyl-3α-(4-fluorophenyl) nortropane (compound 20 (R=4-F), FIG. 5)

2β-(1-Propanoyl)-3α-(4-fluorophenyl)tropane 14 (112 mg, 0.37 mmol) was combined with 1-chloroethyl chloroformate (2.2 mL) and the solution was heated to reflux for 5 h. The excess chloroformate was removed in vacuo and the residue was refluxed in methanol for 45 min. The MeOH was removed in vacuo and the residue was dissolved in $CHCl_3$ and $NaHCO_3/Na_2CO_3$ (pH=9). The aqueous layer was extracted $CHCl_3$ (3×10 mL) and the combined organic extracts were dried ($Na_2SO_4$), filtered and concentrated to yield 104 mg. This residue was chromatographed (eluent: 10–20% $Et_3N$ in EtOAc). Like fractions were combined to yield 20 (65 mg, 60%).

$R_f$ 0.13 (10% $Et_3N$ in EtOAc); $^1$H-NMR ($CDCl_3$) δ 1.30 (ddd, 1H), 1.5–1.75 (m, 2H), 1.85–2.15 (m, 2H), 2.2–2.35 (m, 1H), 2.7–2.9 (m, 1H), 3.05 (s, 3H), 3.1–3.22 (m, 1H), 3.38 (s, 3H), 3.4–3.5 (m, 1H), 3.6–3.7 (m, 1H), 6.9–7.0 (m, 2H), 7.13–7.23 (m, 2H).

EXAMPLE 29

N-[2-(3'-N'-Propyl-(1"R)-3"α-(4-fluorophenyl)tropane-2"β-(methoxymethylcarbamoyl))((2-((triphenylmethyl)thio)ethyl)-amino) acetyl]-S-(triphenyl)-2-aminoethanethiol (Compound 21 (R=4-F), FIG. 5) (O-1450)

2β-(1-Propanoyl)-3α-(4-fluorophenyl)nortropane 20 (65 mg, 0.22 mmol) was combined with MAMA'-Cl (203 mg, 0.27 mmol, 1.2 eq.), KI (74 mg, 0.45 mmol), and $K_2CO_3$ (309 mg, 2.2 mmol) in anhydrous MeCN (10 mL) and brought to reflux for 6 h then cooled to room temperature. The solvent was removed under vacuum and the residue was partitioned between $CHCl_3$ and water. The aqueous layer was extracted with $CHCl_3$ (3×5 mL) and the combined organic extracts were dried ($Na_2SO_4$), filtered and concentrated to yield a yellow oil which was applied to a chromatography column (15 g $SiO_2$ eluent 120 mL of 50% EtOAc/hexanes/5% $Et_3N$). Fractions containing the product were combined and concentrated to yield 21 as a light yellow oil (142 mg, 41%).

$R_f$ 0.7 (5% $Et_3N$/EtOAc); Elemental analysis: calculated (0.3$H_2O$) C, 71.02; H, 6.96; N, 5.26. found C, 71.20; H, 6.45; N, 5.14. $^1$H-NMR ($CDCl_3$) δ 1.2–3.5 (m, 24H), 2.85 (s, 2H), 3.02 (s, 3H), 3.42 (s, 3H), 6.85–7.0 (m, 2H), 7.1–7.7 (m, 32H).

EXAMPLE 30

N-[(2-((3'-N'-Propyl-(1"R)-3"α-(4-fluorophenyl) tropane-2"β-methoxymethylcarbamoyl)(2-mercaptoethyl)amino)acetyl)-2-aminoethane-thiolato]rhenium (V) oxide (Compound 22 (Re: R=4-F), FIG. 5) (O-1451)

N-[2-(3'-N'-propyl-(1"R)-3"α-(4-fluorophenyl)tropane-2"β-(methoxymethyl-carbamoyl))(2-((triphenylmethyl)thio)ethyl)amino)acetyl]-S-(triphenyl)-2-aminoethane-thiol 21 (21 mg, 0.02 mmol) in EtOH (4 mL) was heated to reflux. A solution of $SnCl_2$ (8.4 mg, 0.04 mmol) in 0.005 M HCl (0.5 mL) was added quickly followed immediately by $NaReO_4$ (13 mg, 0.04 mmol) in 0.005 M HCl (0.5 mL). The solution was refluxed for 10 h and was then loaded onto 0.5 g silica and pumped overnight. The silica-adsorbed material was applied to a chromatography column (3 g $SiO_2$, eluent 30% EtOAc/hexanes/5% $Et_3N$). Like fractions were combined and concentrated to yield as a purple foam (3.7 mg; 26%).

$R_f$ 0.5 (25% hexanes in EtOAc); $^1$H-NMR ($CDCl_3$) δ 1.1–4.2 (m, 30H), 4.5–4.6 (m, 1H), 4.75, 5.12 (2d, J=16.7 Hz, 2×6β, 1H), 6.8–7.0 (m, 2H), 7.1–7.2 (m, 2H).

EXAMPLE 31

2β-Methoxymethylcarbamoyl-3α-(4-fluorophenyl) nortropane (Compound 20A (R=4-F), FIG. 5)

2β-(1-Propanoyl)-3α-(4-fluorophenyl)tropane (143 mg, 0.50 mmol) was combined with 1-chloroethyl chloroformate (2 mL) and the solution was heated to reflux for 2 h. The excess chloroformate was removed in vacuo and the residue was refluxed in methanol (30 mL) for 45 min. The methanol was removed in vacuo and the residue was dissolved in $CHCl_3$ and $NaHCO_3/Na_2CO_3$ (pH=9). The aqueous layer was extracted $CHCl_3$ (3×10 mL) and the combined organic extracts were dried ($Na_2SO_4$), filtered and concentrated. The residue was chromatographed (10–20% $Et_3N$ in EtOAc). Like fractions were combined to yield 80 mg (58%).

$^1$H-NMR ($CDCl_3$) δ 1.50 (m, 1H), 1.7 (m, 2H), 1.95–2.22 (m, 2H), 2.5 (ddd, 1H), 2.92 (s, 3H), 3.1–3.4 (m, 2H), 3.3 (s, 3H), 3.6 (m, 1H), 3.72 (m, 1H), 6.9–7.0 (m, 2H), 7.1–7.3 (m, 2H).

EXAMPLE 32

N-[2-(3'-N'-Propyl-(1"R)-3"β-(4-fluorophenyl)tropane-2"β-methoxymethylcarbamoyl)((2-((triphenylmethyl)thio)ethyl)-amino)acetyl]-S-(triphenyl)-2-aminoethanethiol (Compound 21A (R=4-F), FIG. 5)

2β-(1-Propanoyl)-3β-(4-fluorophenyl)nortropane (80 mg, 0.28 mmol) was combined with MAMA'-Cl (244 mg, 0.32 mmol,), KI (84 mg, 0.5 mmol, 2.0 eq.), and $K_2CO_3$ (322 mg, 2.3 mmol) in anhydrous MeCN (10 mL) and brought to reflux overnight then cooled to room temperature. The solvent was removed under vacuum and the residue was applied to a chromatography column (5% $Et_3N$ in EtOAc). Fractions containing the product were combined and concentrated to yield the product as a light yellow foam (80 mg, 29%).

$R_f$ 0.65 (5% $Et_3N$ in EtOAc); $^1$H-NMR ($CDCl_3$) δ 1.2–3.1 (m, 28H), 3.37 (m, 1H), 3.51 (s, 3H), 3.55 (m, 1H), 6.9–7.0 (m, 2H), 7.1–7.5 (m, 32H).

EXAMPLE 33

N-((2-((3'-N'-Propyl-(1"R)-3"β-(4-fluorophenyl)tropane-2"β-methoxymethylcarbamoyl)(2-mercaptoethyl)amino)acetyl)-2aminoethanethiolato]rhenium (V) oxide (Compound 22A (Re: R=4-F), FIG. 5) (O-1451)

N-[2-(3'-N'-propyl-(1"R)-3"β-(4-fluorophenyl)tropane-2"β-methoxymethyl-carbamoyl)((2-((triphenylmethyl)thio)ethyl)amino)acetyl]-S-(triphenyl)-2-amino-ethanethiol (22 mg, 0.02 mmol) in EtOH (10 mL) was heated to reflux. A solution of $SnCl_2$ (8.4 mg, 0.05 mmol) in 0.005 M HCl (1.0 mL) was added quickly followed immediately by $NaReO_4$ (13 mg, 0.05 mmol) in 0.005 M HCl (0.5 mL). The solution was refluxed for 10 h and was then applied to a chromatography column (65% EtOAc/hexanes/5% $Et_3N$). Like fractions were combined and concentrated to yield a foam (10 mg; 65%).

$R_f$ 0.44 (5% $Et_3N$, 30% hexanes in EtOAc); $^1$H-NMR (CDCl$_3$) δ 1.5–4.2 (m, 30H), 4.4–4.6 (m, 1H), 4.72, 5.05 (2d, J=16.5 Hz, 1H), 6.8–7.0 (m, 2H), 7.1–7.3 (m, 2H).

EXAMPLE 34

(1R)-N-Methyl-2-hydroxymethyl-3-(4-fluorophenyl)-8-azabicyclo[3.2.1]oct-2-ene (Compound 38 (R=4-F), FIG. 9) (O-1337)

(1 R)-N-Methyl-2-methoxycarbonyl-3-(4-fluorophenyl)-8-azabicyclo[3.2.1]oct-2-ene 3 (500 mg, 1.82 mmol) was dissolved in benzene (15 mL) and LAH (70 mg, 1.82 mmol) was added. The reaction was heated to 60° C. overnight. The reaction was cooled to 0° C., and water (70 μL), 15% NaOH (70 μL), water (200 μL) were added. The reaction was stirred for 15 min and then the salts were filtered off through a pad of celite. The filtrate was dried over $Na_2SO_4$ filtered and concentrated to yield 38 (454 mg, 90%) which was purified by column chromatography (30 g $SiO_2$; eluent: 4% $Et_3N$ in 10% MeOH/CHCl$_3$). Like fractions were combined, reduced and pumped at high vacuum overnight to yield 38 (336 mg, 74%).

Mp. 106.6–108.7° C.; $R_f$ 0.2 (10% MeOH/CHCl$_3$; 5% $Et_3N$); $^1$H-NMR (CDCl$_3$) δ 1.5–1.7 (m, 1H), 1.9–2.0 (m, 3H), 2.1–2.3 (m, 2H), 2.4 (s, 3H), 2.72 (brd, J=18 Hz, 1H), 3.31 (br s, 1H), 3.55 (d, J=4.1 Hz, 1H), 3.89 (d, J=12.3 Hz, 1H), 4.02 (d, J=12.3 Hz, 1H), 6.9–7.0 (m, 2H), 7.1–7.2 (m, 2H). Elemental analysis: calculated C, 72.85; H, 7.34; N, 5.66. found C, 72.94; H, 7.33; N, 5.73.

EXAMPLE 35

(1R)-N-Methyl-2-hydroxymethyl-3-(3,4-dichlorophenyl)-8-azabicyclo[3.2.1]oct-2-ene (Compound 38 (R=3,4-Cl$_2$), FIG. 9)

(1R)-N-Methyl-2-methoxycarbonyl-3-(3,4-dichlorophenyl)-8-azabicyclo[3.2.1]-oct-2-ene 3 (508 mg, 1.56 mmol) was dissolved in benzene (20 mL) and LAH (62 mg, 1.56 mmol) was added. The reaction was heated to reflux overnight. The reaction was cooled to 0° C., and water (80 μL), 10% KOH (90 μL), water (300 μL) were added. The reaction was stirred for 15 min and then the salts were filtered off through a pad of celite. The filtrate was dried over $Na_2SO_4$ filtered and concentrated to yield a yellow foam (420 mg, 90%) and purified by column chromatography (3% $Et_3N$/7% MeOH in CHCl$_3$) to give 280 mg (60%).

$R_f$ 0.2 (5% MeOH/CHCl$_3$; 3% $Et_3N$); $^1$H-NMR (CDCl$_3$) δ 1.5–1.66 (m, 1H), 1.84–1.98 (m, 2H), 2.0 (m, 2H), 2.08–2.24 (m, 2H), 2.39 (s, 3H), 2.7 (dd, 1H), 3.3 (m, 1H), 3.54 (d, J=5.5 Hz, 1H), 3.89 (d, J=11.8 Hz, 1H), 4.01 (d, J=11.8 Hz, 1H), 6.99 (dd, 1H), 7.25 (d, 1H), 7.37 (d, 1H).

EXAMPLE 36

(1R)-N-Methyl-2-carbonyl-3-(4-fluorophenyl)-8-azabicyclo[3.2.1]-oct-2-ene (compound 39 (R=4-F), FIG. 9)

A solution of (COCl)$_2$ (55 mg, 40 μL, 0.43 mmol) and CH$_2$Cl$_2$ (2 mL) was cooled to −78° C. and DMSO (65 μL) was added dropwise over 3 min. The reaction was stirred for a further 5 min at −78° C. and compound 38 (90 mg, 0.36 mmol) in CH$_2$Cl$_2$ (2 mL) was added dropwise over 10 min. After a further 20 min, $Et_3N$ (250 μL, 1.80 mmol) was added over 30 min. The reaction was stirred for a further 10 min and then allowed to warm to room temperature. CH$_2$Cl$_2$ (20 mL) and 1M NaOH was added, the layers partitioned and the aqueous layer was washed with CH$_2$Cl$_2$ (1×15 mL). Combined organic extracts were dried over $Na_2SO_4$, filtered, concentrated and pumped at high vacuum. The yellow oil obtained (86 mg) was purified by column chromatography (4.5 g $SiO_2$; 30% EtOAc/hexanes/5% $Et_3N$) and like fractions were combined, concentrated and dried at high vacuum to yield the product 39 (62 mg, 63%).

$R_f$ 0.2 (20% EtOAc/hexane, 5% $Et_3N$); $^1$H-NMR (CDCl$_3$) δ 1.55–1.65 (m, 1H), 1.72–1.82 (m, 2H), 2.14–2.3 (m, 2H), 2.40 (s, 3H), 2.9–3.0 (m, 1H), 3.36–3.44 (m, 1H), 4.02–4.30 (m, 1H), 7.0–7.1 (m, 2H), 7.16–7.24 (m, 2H), 9.45 (s, 1H).

EXAMPLE 37

(1R)-N-Methyl-2-carbonyl-3-(3,4-dichlorophenyl)-8-azabicyclo[3.2.1]oct-2-ene (Compound 39 (R=3,4-Cl$_2$), FIG. 9)

A solution of (COCl)$_2$ (125 mg, 87 μL, 1.0 mmol) and CH$_2$Cl$_2$ (20 mL) was cooled to −78° C. and DMSO (150 μL) was added dropwise over 3 min. The reaction was stirred for a further 5 min at −78° C. and compound 38 (245 mg, 0.82 mmol) in CH$_2$Cl$_2$ (5 mL) was added dropwise over 7 min. After a further 30 min, $Et_3N$ (600 μL, 4.0 mmol) was added over about 15 min. The reaction was stirred for a further 10 min. and then allowed to warm to room temperature. CH$_2$Cl$_2$ (20 mL) and $Na_2CO_3$ (20 mL; 1M) was added, the layers partitioned and the aqueous layer was washed with CH$_2$Cl$_2$ (1×20 mL). Combined organic extracts were dried $Na_2SO_4$, filtered, concentrated and pumped at high vacuum. The residue was purified by column chromatography (25 g $SiO_2$; 60% EtOAc/hexanes/5% $Et_3N$) and like fractions were combined, concentrated and dried at high vacuum to yield the product 39 (154 mg, 63%).

$R_f$ 0.2 (75% EtOAc/hexane, 5% $Et_3N$); $^1$H-NMR (CDCl$_3$) δ 1.5–1.7 (m, 1H), 1.7–1.85 (m, 1H), 2.1–2.3 (m, 2H), 2.38 (s, 3H), 2.93 (dd, 1H), 3.39 (m, 1H), 4.05 (dd, 1H), 7.08 (dd, 1H), 7.34 (d, 1H), 7.46 (d, 1H), 9.45 (s, 1H).

EXAMPLE 38

(1R)-N-Methyl-2-(2-hyroxypropyl)-3-(4-fluorophenyl)-8-azabicyclo[3.2.1]oct-2-ene (Compound 40 (R=4-F), FIG. 9)

Compound 39 (62 mg, 0.26 mmol) was dissolved in anhydrous THF at room temperature and EtMgBr/Et$_2$O (3M; 900 µl) was added dropwise. The reaction was stirred at room temperature for 20 min and then at 65° C. overnight, and then added slowly to a mixture of 1M HCl (50 mL) and Et$_2$O (50 mL) at 0° C. The mixture was basified with saturated aq. Na$_2$CO$_3$ and separated. The aqueous layer was extracted with CHCl$_3$ (2×20 mL), dried (Na$_2$SO$_4$), filtered, evaporated and dried at high vacuum. The residue (90 mg) was purified by column chromatography (6 g SiO$_2$; 5% Et$_3$N/EtOAc) and like fractions were combined, evaporated and dried at high vacuum to yield 40 (82 mg, 52%).

R$_f$ 0.4 (10% MeOH/CHCl$_3$/5% Et$_3$N); $^1$H-NMR (CDCl$_3$) β 0.83 (t, J=7.6 Hz, 3H), 1.4–1.7 (m, 4H), 1.81 (d, J=18 Hz, 1H), 2.0 (m, 1H), 2.1–2.3 (m, 2H), 2.42 (s, 3H), 2.7 (m, 1H), 3.3 (m, 1H), 3.53 (m, 1H), 4.1–4.2 (m, 1H), 6.9–7.1 (m, 4H)

EXAMPLE 39

(1R)-N-Methyl-2-(2-hyroxypropyl)-3-(3,4-dichlorophenyl)-8-azabicyclo[3.2.1]oct-2-ene (Compound 40 (R=3,4-Cl$_2$), FIG. 9)

Compound 39 (150 mg, 0.5 mmol) was dissolved in anhydrous THF (25 mL) at room temperature and EtMgBr/Et$_2$O (3M; 350 µl, 1.05 mmol) was added dropwise over 2 min. The reaction was stirred at room temperature for 2.75 h and then added slowly to a mixture of 1M HCl (20 mL) and Et$_2$O (20 mL). The mixture was basified with saturated aq. Na$_2$CO$_3$ and separated. The aqueous layer was extracted with CHCl$_3$ (3×20 mL) dried (Na$_2$SO$_4$), filtered, evaporated and dried at high vacuum.

The residue (197 mg) was purified by column chromatography (20 g SiO$_2$; 5% Et$_3$N/EtOAc) and like fractions were combined, evaporated and dried at high vacuum to yield 40 (109 mg, 66%).

R$_f$ 0.07 (5% Et$_3$N, 20% hexane in EtOAc); $^1$H-NMR (CDCl$_3$) δ 0.85 (t, J=7.4 Hz, 3H), 1.4–1.7 (m, 4H), 1.79 (d, J=17.6 Hz, 1H), 1.95–2.1 (m, 1H), 2.1–2.3 (m, 2H), 2.42 (s, 3H), 2.68 (dd, J=4, 18 Hz, 1H), 3.3 (m, 1H), 3.38 (d, 1H), 3.52 (d, J=5 Hz, 1H), 4.1–4.2 (m, 1H), 6.94 (dd, 1H), 7.20 (dd, 1H).

EXAMPLE 40

(1R)-2-Propanoyl-3-(4-fluorophenyl)-8-azabicyclo[3.2.1]oct-2-ene (Compound 26 (R=4-F), FIG. 9)

Tropane 40 (28 mg, 0.1 mmol) in CH$_2$Cl$_2$ was added dropwise to a cold (−78° C.) solution of (COCl)$_2$ (5.5 µL, 0.12 mmol) and DMSO (20 µL, 0.26 mmol) in CH$_2$Cl$_2$.

After stirring for 30 min at −78° C., Et$_3$N (75 µL, 0.5 mmol) was added and the reaction was warmed to room temperature. CH$_2$Cl$_2$ and 1M NaOH were added and the layers separated. The organic layer was dried (Na$_2$SO$_4$), filtered and evaporated and the product applied to a chromatography column (5% Et$_3$N, 25% hexane, 70% EtOAc) to give 18.6 mg of product (66%).

R$_f$ 0.2 (5% Et$_3$N, 25% Hexanes, 70% EtOAc); $^1$H-NMR (CDCl$_3$) δ 0.80 (t, 3H), 1.6 (m, 1H), 1.8–2.3 (m, 6H), 2.40 (s, 3H), 2.75 (dd, 1H), 3.35 (m, 1H), 3.73 (m, 1H), 7.0 (m, 2H), 7.05–7.15 (m, 2H).

EXAMPLE 41

(1R)-2-Methoxycarbonyl-3-(4-fluorophenyl)-8-norazabicyclo[3.2.1]-oct-2-ene (Compound 29 (R=4-F), FIG. 7) (O-1131)

2-Methoxycarbonyl-3-(4-fluorophenyl)tropene 3 (362 mg, 1.3 mmol) was combined with 1-chloroethyl chloroformate (1 mL) and the solution was heated to reflux for 2 h. The excess chloroformate was removed in vacuo and the residue was refluxed in methanol (30 mL) for 45 min. The methanol was removed in vacuo and the residue was dissolved in CHCl and NaHCO$_3$/Na$_2$CO$_3$ (pH=9). The aqueous layer was extracted CHCl (3×10 mL) and the combined organic extracts were dried (Na$_2$SO$_4$), filtered and concentrated. The residue was chromatographed (eluent: 1–3% Et$_3$N in EtOAc+0.5% NH4OH). Like fractions were combined to yield a yellow solid (234 mg, 68%).

R$_f$ 0.7 (10% MeOH in hexanes+0.5% NH$_4$OH); mp. 67–68° C.; $^1$H-NMR (CDCl$_3$) δ 1.50–3.0 (m, 6H), 3.8 (m, 1H), 4.2 (m, 1H), 6.8–7.2 (m, 4H). Elemental analysis: calculated C, 68.95; H, 6.17; N, 5.36. found C, 68.81; H, 6.24; N, 5.40.

EXAMPLE 42

(1R)-2-Methoxycarbonyl-3-(3,4-dichlorophenyl)-8-norazabicyclo[3.2.1]oct-2-ene (Compound 29 (R=3,4-Cl$_2$), FIG. 7) (O-1130)

2-Methoxycarbonyl-3-(3,4-dichlorophenyl)tropene (200 mg, 0.61 mmol) was combined with 1-chloroethyl chloroformate (4 mL) and the solution was heated to reflux for 2 h. The excess chloroformate was removed in vacuo and the residue was refluxed in methanol (30 mL) for 45 min. The methanol was removed in vacuo and the residue was dissolved in CHCl$_3$ and NaHCO$_3$/Na$_2$CO$_3$ (pH=9). The aqueous layer was extracted CHCl$_3$ (3×10 mL) and the combined organic extracts were dried (Na$_2$SO$_4$), filtered and concentrated. The residue was chromatographed (eluent: 5–15% Et$_3$N in EtOAc). Like fractions were combined to yield a yellow oil.

R$_f$ 0.3 (10% Et$_3$N in EtOAc); $^1$H-NMR (CDCl$_3$) δ 1.50–2.3 (m, 5H), 2.5–2.9 (m, 1H), 3.53 (s, 3H), 3.8 (m, 1H), 4.2 (m, 1H), 6.9 (dd, 1H), 7.2 (dd, 1H), 7.4 (d, 1H). Elemental analysis: calculated C, 57.71; H, 4.84; N, 4.49. found C, 57.45; H, 4.87; N, 4.47.

EXAMPLE 43

N-[2-(3'-N'-Propyl-(1"R)-3"-(4-fluorophenyl)trop-2-ene-2"-(methoxycarbonyl))((2-((triphenylmethyl)thio)ethyl)amino)acetyl]-S-(triphenyl)-2-aminoethanethiol (Compound 30 (R=4-F), FIG. 7)

2-(1-Methoxycarbonyl)-3-(4-fluorophenyl)nortrop-2-ene (134 mg, 0.5 mmol) was combined with MAMA'-Cl (387 mg, 0.5 mmol,), KI (85 mg, 0.5 mmol), and K$_2$CO$_3$ (707 mg, 5 mmol) in anhydrous MeCN (10 mL) and brought to reflux overnight then cooled to room temperature. The solvent was removed under vacuum and the residue was applied to a chromatography column (1–6% Et$_3$N in EtOAc). Fractions containing the product were combined and concentrated to yield the product as a light yellow foam (148 mg, 29%).

R$_f$ 0.18 (10% Et$_3$N in hexane); $^1$H-NMR (CDCl$_3$) δ 1.3–3.15 (m, 22H), 3.2–3.4 (m, 1H), 3.5 (s, 3H), 3.8–3.9 (m, 1H), 6.8–7.8 (m, 34H).

EXAMPLE 44

N-[2-(3'-N'-Propyl-(1"R)-3"-(3,4-dichlorophenyl)trop-2-ene-2"-(methoxycarbonyl)((2-((triphenylmethyl)thio)ethyl)amino)acetyl]-S-(triphenyl)-2-aminoethanethiol (Compound 30 (R=3,4-Cl$_2$), FIG. 7)

2-(1-Methoxycarbonyl)-3-(3,4-dichlorophenyl)nortrop-2-ene (107 mg, 0.34 mmol) was combined with MAMA'-Cl (258 mg, 0.34 mmol,), KI (57 mg, 0.34 mmol), and K$_2$CO$_3$ (472 mg, 3.4 mmol) in anhydrous MeCN (10 mL) and brought to reflux overnight then cooled to room temperature. The solvent was removed under vacuum and the residue was applied to a chromatography column (1–6% Et$_3$N in EtOAc).

Fractions containing the product were combined and concentrated to yield the product as a foam (111 mg, 31%).

R$_f$ 0.18 (5% Et$_3$N in hexane); $^1$H-NMR (CDCl$_3$) δ 1.4–3.2 (m, 22H), 3.2–3.4 (m, 1H), 3.5 (s, 3H), 3.8–3.9 (m, 1H), 6.8–7.6 (m, 33H).

EXAMPLE 45

N-[(2-((3'-N'-Propyl-(1"R)-3"-(4-fluorophenyl)trop-2-ene-2"-methoxycarbonyl)(2-mercaptoethyl)amino)acetyl)-2-aminoethane-thiolato]rhenium (V) oxide (Compound 31 (Re: R=4-F), FIG. 7) (O–1135)

A solution of N-[2-(3'-N'-propyl-(1"R)-3"-(4-fluorophenyl)trop-2-ene-2"-(methoxycarbonyl)(2-((triphenylmethyl)thio)ethyl)amino)acetyl]-S-(triphenyl)-2-aminoethanethiol (130 mg, 0.13 mmol) in EtOH (10 mL) was heated to reflux. A solution of SnCl$_2$ (28 mg, 0.15 mmol) in 0.005 M HCl (1.0 mL) was added quickly followed immediately by NaReO$_4$ (40 mg, 0.15 mmol) in 0.005 M HCl (0.5 mL). The solution was refluxed for 10 h and was then applied to a chromatography column (1–10% Et$_3$N in EtOAc). Like fractions were combined and concentrated to yield a foam (34 mg; 37%).

R$_f$ 0.09 (10% Et$_3$N in EtOAc); $^1$H-NMR (CDCl$_3$) δ 1.4–4.3 (m, 23H), 3.5 (s, 3H), 4.5–4.9 (m, 2H), 6.9–7.2 (m, 4H). Elemental analysis: calculated C, 41.49; H, 4.50; N, 6.05. found C, 41.77; H, 4.44; N, 5.93. Accurate mass calculated 696.1348. found 696.1405.

EXAMPLE 46

N-[(2-((3'-N'-Propyl-(1"R)-3"-(3,4-dichlorophenyl)trop-2-ene-2"-methoxycarbonyl)(2-mercaptoethyl)amino)acetyl)-2-aminoethane-thiolato]rhenium (V) oxide (Compound 31 (Re: R=3,4-Cl$_2$), FIG. 7) (O-1136)

A solution of N-[2-(3'-N'-propyl-(1"R)-3"-(3,4-dichlorophenyl)trop-2-ene-2"-(methoxycarbonyl)(2-((triphenylmethyl)thio)ethyl)amino)acetyl] -S-(triphenyl)-2-aminoethanethiol (100 mg, 0.1 mmol) in EtOH (10 mL) was heated to reflux. A solution of SnCl$_2$ (20 mg, 0.1 mmol) in 0.005 M HCl (1.0 mL) was added quickly followed immediately by NaReO$_4$ (29 mg, 0.11 mmol) in 0.005 M HCl (0.5 mL). The solution was refluxed for 10 h and was then applied to a chromatography column (1–10% Et$_3$N in EtOAc). Like fractions were combined and concentrated to yield a foam (56 mg; 78%).

R$_f$ 0.09 (10% Et$_3$N in EtOAc); $^1$H-NMR (CDCl$_3$) δ 1.4–4.2 (m, 23H), 3.55 (s, 3H), 4.4–4.9 (m, 2H), 6.95 (dd, 1H), 7.2 (d, 1H), 7.4 (d, 1H). Elemental analysis: calculated C, 38.65; H, 4.05; N, 5.63. found C, 38.91; H, 3.96; N, 5.57. Accurate mass calculated 746.0663. found 746.0689.

EXAMPLE 47

N-[2-(3'-N'-Propyl-(1"R-3"-(4-fluorophenyl)-2"β-methoxycarbonyl-tropane))((2-((triphenylmethyl)thio)ethyl)amino)acetyl]-2-amino-ethanethiol (Compound 33 (R=4-F), FIG. 8)

To a solution of nor-3β-(4-fluorophenyl)-2β-methoxycarbonyltropane (52.6 mg, 0.2 mmol) in dry acetonitrile (10 mL) was added in succession N-[2-((3-chloropropyl)-(2-((triphenylmethyl)thio)ethyl)amino)acetyl]-S-(triphenylmethyl)-2-aminoethanethiol (151 mg, 0.2 mmol), KI (33 mg, 0.2 mmol), and K$_2$CO$_3$ (280 mg, 2.0 mmol). The resulting slurry was then boiled overnight. Once the reaction was complete then the solution was allowed to cool to room temperature and then 2 g of silica gel was added and the solvent evaporated. The resulting solid was layered onto a silica gel column and eluted with 0.5% NH$_4$OH in 1:1 solution of EtOAc and hexanes. The title compound was recovered as a foam in 72% yield (141 mg). This was converted to the dihydrochloride.

Mp. 166–168° C.; IR (KBr) 1666 cm$^{-1}$; $^1$H-NMR (CDCl$_3$) δ 1.8–3.8, (m, 24H), 3.3 (s, 3H), 3.9–4.0 (m, 1H), 4.2–4.3 (m, 1H), 4.4–4.5 (m, 1H), 6.9–7.4 (m, 34 H). Elemental analysis: calculated (2 HCl.2 H$_2$O): C, 68.24; H, 6.47; N, 3.85. Found: C, 38.03; H, 6.40; N, 3.82.

EXAMPLE 48

(RS)-N-[2-((3'-N'-Propyl-(1"R-3"β-(3,4-dichlorophenyl)-2"β-methoxycarbonyltropane))(2-mercaptoethyl)amino)acetyl)-2-aminoethanethiol (Compound 33 (R=3,4-Cl$_2$), FIG. 8) (O-863)

Prepared identically to the compound in Example 47 above.

Mp. 108° C., IR (KBr) 1724, 1653, 957 cm$^{-1}$; $^1$H-NMR (CDCl$_3$) δ 1.5–3.9 (m, 22H), 3.55 & 3.50 (2s, 3H), 3.9–4.2 (m, 2H), 4.5–4.7 (m, 1H), 4.80 (d, 16.4 Hz, 1H), 7.0–7.4 (m, 3H); Accurate mass calculated for C$_{24}$H$_{33}$Cl$_2$N$_3$S$_2$O$_4$Re [MH]$^+$748.0819. found 748.0856. Elemental analysis: calculated, C, 38.55; H, 4.31; N, 5.62. Found C, 38.79; H, 4.38; N, 5.41.

EXAMPLE 49

(RS)-N-[2-((3'-N'-Propyl-(1"R-3"β-(4-fluorophenyl)-2"β-methoxycarbonyltropane))(2-mercaptoethyl)amino)acetyl)-2-aminoethane-thiolato]rhenium (V) oxide (Compound 34 (Re: R=4-F), FIG. 8) (O-861)

N-[2-((3'-N'-Propyl-3"β-(4-fluorophenyl)tropane-2"β-carboxylic acid methyl ester)(2-((triphenylmethyl)thio)ethyl)amino)acetyl]-S-(triphenylmethyl)-2-aminoethanethiol (98 mg, 0.1 mmol) were dissolved in boiling ethanol (1.5 mL). To this was added a solution of SnCl$_2$ (21 mg, in 200 mL of 0.05 M HCl), followed immediately by a solution of NaReO$_4$ (30 mg in 200 mL of 0.05 M HCl). Boiling was continued overnight, after which boiling CH$_3$CN (10 mL) was added and the resulting solution filtered through a pad of celite. The cake was further washed two more times with boiling CH$_3$CN (2×20 mL). To the filtrate was added silica gel (1 g) and the solvent evaporated.

The solid was then layered onto a silica gel column and eluted with EtOAc. The title compound was isolated as a mixture of diastereomers in 90% yield (608 mg).

Mp 101.9° C., IR (KBr) 1720, 1666, 957 cm$^{-1}$; $^1$H-NMR (CDCl$_3$) δ 1.4–4.2, (m, 24H), 3.46 & 3.5 (2s, 3H), 4.4–4.7 (m, 1H), 4.80 & 4.82 (2d, 16 Hz, 1H), 6.8–7.3 (m, 4H); Accurate mass calculated for C$_{24}$H$_{34}$FN$_3$S$_2$O$_4$Re [MH]+ 698.1505. found 698.1557. This was converted to a hydrochloride for analysis: Elemental analysis: calculated (HCl.2 H$_2$O) C, 37.47; H, 4.98; N, 5.46. Found C, 37.45; H, 4.95; N, 5.40.

EXAMPLE 50

(RS)-N-[2-((3'-N'-Propyl-(1"R-3"β-(3,4-dichlorophenyl)-2"β-methoxycarbonyltropane))(2-mercaptoethyl)amino)acetyl)-2-aminoethane thiolato rhenium (V) oxide (Compound 34 (Re: R=3,4-Cl$_2$), FIG. 8) (O-863)

Prepared identically to the compound in Example 49 above.

Mp. 108° C., IR (KBr) 1724, 1653, 957 cm$^{-1}$; $^1$H-NMR (CDCl$_3$) δ 1.5–3.9 (m, 22H), 3.55 & 3.50 (2s, 3H), 3.9–4.2 (m, 2H), 4.5–4.7 (m, 1H), 4.80 (d, 16.4 Hz, 1H), 7.0–7.4 (m, 3H); Accurate mass calculated for C$_{24}$H$_{33}$Cl$_2$N$_3$S$_2$O$_4$Re [MH]$^+$748.0819. found 748.0856. Elemental analysis: calculated, C, 38.55; H, 4.31; N, 5.62. Found C, 38.79; H, 4.38; N, 5.41.

EXAMPLE 51

(1R)-2β-Methoxycarbonyl-3α-(3,4-dichlorophenyl)-8-azabicyclo[3.2.1]octane (Compound 35 (R=3,4-Cl$_2$), FIG. 8)

(1R)-N-Methyl-2β-methoxycarbonyl-3α-(3,4-dichlorophenyl)-8-azabicyclo[3.2.1]-octane 12 (375 mg, 1.14 mmol) and α-chloroethyl chloroformate (ACE-Cl) (3 mL) were combined and heated at 100° C. (oil bath temperature) for 1 h. Excess ACE-Cl was then removed under reduced pressure, and methanol (50 mL) was added to the residue. The mixture was then heated at reflux for 30 min and then concentrated to dryness. The residue obtained was dissolved in CH$_2$Cl$_2$ (75 mL), washed with aqueous NH$_4$OH, dried over Na$_2$SO$_4$, filtered, and concentrated to afford the crude demethylated product. Purification by flash chromatography (1% NH$_4$OH, 50–0% hexanes, 50–90% EtOAc 0–10% methanol) gave 250 mg (70%) of 35.

R$_f$ 0.14, (5% Et$_3$N/EtOAc/hexanes 1:1); $^1$H-NMR (CDCl$_3$) δ 1.1–2.5 (m, 8H), 2.9–3.3 (m, 1H), 3.5–3.8 (m, 1H), 3.6 (s, 3H), 6.95–7.40 (m, 3H).

EXAMPLE 52

(1R)-2β-Methoxycarbonyl-3α-(4-fluorophenyl)-8-azabicyclo[3.2.1]-octane (Compound 35 (R=4-F), FIG. 8)

(1R)-N-Methyl-2β-methoxycarbonyl-3α-(4-fluorophenyl)-8-azabicyclo[3.2.1]-octane (95 mg, 0.34 mmol) and ACE-Cl (7 mL) were combined and heated at 100° C. (oil bath temperature) for 1 h. Excess ACE-Cl was then removed under reduced pressure, and methanol (50 mL) was added to the residue. The mixture was then heated at reflux for 30 min and then concentrated to dryness. The residue obtained was dissolved in CH$_2$Cl$_2$ (75 mL), washed with aqueous NH$_4$OH, dried over Na$_2$SO$_4$, filtered, and concentrated to afford the crude demethylated product. Purification by flash chromatography (0–5% NH$_4$OH, 10% MeOH in EtOAc) gave 86 mg (95%) of 35.

R$_f$ 0.66, (10% MeOH/EtOAc+0.5% NH$_4$OH); $^1$H-NMR (CDCl$_3$) δ 1.2 (ddd, 1H), 1.2–2.8 (m, 5H), 3.3–3.6 (m, 2H), 3.5 (s, 3H), 3.8–4.2 (m, 2H), 6.9–7.3 (m, 4H).

EXAMPLE 53

N-[2-(3'-N'-Propyl-(1"R)-3"α-(3,4-dichlorophenyl)-2"β-methoxycarbonyltropane))((2-((triphenylmethyl)thio)ethyl)amino)acetyl]-S-(triphenyl)-2-aminoethanethiol (Compound 36 (R=3,4-Cl$_2$), FIG. 8)

To a solution of (1R)-2β-methoxycarbonyl-3α-(3,4-dichlorophenyl)-8-azabicyclo [3.2.1]octane 35 (250 mg, 0.79 mmol) in dry CH$_3$CN (40 mL) was added in succession N-[[[2-(triphenylmethyl)thio]ethyl](N'-3'-chloropropyl)amino]acetyl]-S-(triphenyl-methyl)-2-aminoethanethiol (601 mg, 0.79 mmol), KI (132 mg), and K$_2$CO$_3$ (1.1 g). The resulting slurry was maintained at reflux overnight. Once the reaction was complete, the solution was allowed to cool to room temperature and then partitioned between concentrated aqueous NH$_4$OH and CH$_2$Cl$_2$. The layers were separated and the organic phase dried with Na$_2$SO$_4$. The solution was filtered and concentrated and the residue purified by flash chromatography (15 g, SiO$_2$; 0–5% Et$_3$N in a 1:1 mixture of EtOAc/hexanes) which gave 100 mg (12%) of a white foam.

R$_f$ 0.26 (2.5% NH$_4$OH in EtOAc/hexanes 1/1); $^1$H-NMR (CDCl$_3$) δ 1.20–1.54 (m, 5H), 1.80–2.50 (m, 15H), 2.81 (d, J=17 Hz, 1H), 2.88 (d, J=17 Hz, 1H), 3.00 (m, 2H), 3.16–3.40 (m, 3H), 3.54 (s, 3H), 7.03 (dd, J=2.2, 8.5 Hz, 1H), 7.14–7.53 (m, 32H). Elemental analysis: calculated, C, 72.07; H, 6.15; N, 4.07; Cl, 6.86. found C, 72.18; H, 6.21; N, 3.97; Cl, 6.75.

EXAMPLE 54

N-[2-(3'-N'-Propyl-(1"R)-3"α-(4-fluorophenyl)-2"β-methoxy-carbonyl-tropane))((2-((triphenylmethyl)thio)ethyl)amino)acetyl]-S-(triphenyl)-2-aminoethanethiol (Compound 36 (R=4-F), FIG. 8)

To a solution of (1R)-2β-methoxycarbonyl-3α-(4-fluorophenyl)-8-azabicyclo [3.2.1]octane 35 (230 mg, 0.87 mmol) in dry CH$_3$CN (25 mL) was added in succession N-[[[2-[2-(triphenylmethyl)thio]ethyl](N'-3'-chloropropyl)amino]acetyl]-S-(triphenyl-methyl)-2-aminoethanethiol (660 mg, 0.87 mmol), KI (145 mg, 0.87 mmol), and K$_2$CO$_3$ (1.21 g, 8.7 mmol). The resulting slurry was then maintained at reflux overnight. Once the reaction was complete, the solution was allowed to cool to room temperature and then partitioned between concentrated aqueous NH$_4$OH and CH$_2$Cl$_2$. The layers were separated and the organic phase dried with Na$_2$SO$_4$. The solution was filtered and concentrated and the residue purified by flash chromatography (50% EtOAc/hexanes+1% NH$_4$OH) which gave 435 mg (51%) of a foam.

R$_f$ 0.45 (1% Et$_3$N, 50% EtOAc, 49% hexanes); $^1$H-NMR (CDCl$_3$) δ 1.20 1.3 (m, 1H), 1.3–2.5 (m, 19H), 2.81 (d, J=17 Hz, 1H), 2.86 (d, J=17 Hz, 1H), 2.95–3.05 (m, 2H), 3.10–3.4 (m, 3H), 3.50 (s, 3H), 6.89–6.96 (m, 2H), 7.1–7.5 (m, 32H). Elemental analysis: calculated (0.75 H$_2$O), C, 74.78; H, 6.63; N, 4.22. found C, 74.80; H, 6.64; N, 4.17.

EXAMPLE 55

N-[(2-((3'-N'-Propyl-(1"R)-3"α-(4-fluorophenyl)-2"β-methoxy-carbonyltropane)(2-mercaptoethyl) amino)acetyl)-2-amino-ethanethiolato]-rhenium (V) oxide (Compound 37 (R=4-F), FIG. 8) (O-1186)

A solution of N-[2-(3'-N'-propyl-(1"R)-3"α-(4-fluorophenyl)-2"β-methoxy-carbonyltropane)(2-((triphenylmethyl) thio)ethyl)amino)acetyl]-S-(triphenyl)-2-aminoethane-thiol (226 mg, 0.23 mmol) in EtOH (10 mL) was heated to reflux. A solution of $SnCl_2$ (48 mg, 0.25 mmol) in 0.05 M HCl (1.0 mL) was added quickly followed immediately by $NaReO_4$ (69 mg, 0.25 mmol) in 0.05 M HCl (0.5 mL). The solution was refluxed for 10 h and was then applied to a chromatography column (5% $Et_3N$ in $Et_2O$). Like fractions were combined and concentrated to yield a foam (33 mg; 21%).

$R_f$ 0.38 (10% $Et_3N$ in EtOAc); $^1$H-NMR ($CDCl_3$) δ 0.9–4.3 (m, 24H), 3.53, 3.56 (2s, 3H), 4.4–4.7 (m, 1H), 4.75, 5.00 (2s, 1H), 6.8–7.4 (m, 4H). Elemental analysis: calculated (2/7 $Et_2O$) C, 42.06; H, 5.03; N, 5.85. found C, 42.08; H, 4.93; N, 5.85.

EXAMPLE 56

N-[(2-((3'-N-Propyl-(1"R)-3"α-(3,4-dichlorophenyl)-2"β-methoxy-carbonyltropane) (2-mercaptoethyl)amino)acetyl)-2-aminoethane-thiolato]rhenium (V) oxide (compound 37 (R=3,4-$Cl_2$), FIG. 8) (O-1196)

Prepare identically to the compound in Example 55.

$R_f$ 0.51 (10% $Et_3N$/EtOAc); $^1$H-NMR ($CDCl_3$) δ 1.2–1.4 (m, 1H), 1.4–2.5 (m, 11H), 2.89 (m, 1H), 3.10–3.40 (m, 5H), 3.56 & 3.60 (2s, 3H), 3.6–3.8 (m, 0.5H), 3.90–4.15 (m, 3.5H), 4.60 (m, 1H), 4.73 & 4.95 (2d, J=16.2 & 16.2 Hz, 2×0.5H), 7.0–7.1 (m, 1H), 7.24–7.36 (m, 2H). Elemental analysis: calculated ($H_2O$), C, 37.64; H, 4.48; N, 5.49. found C, 37.59; H, 4.31; N, 5.55.

EXAMPLE 57

(1R)-N-Methyl-2-methoxycarbonyl-3-(2-naphthyl)-8-azabicyclo[3.2.1]oct-2-ene (Compound 50, FIG. 10)

(1R)-2-(Methoxycarbonyl)-3-[[(trifluoromethyl)sulfonyl] oxy]trop-2-ene 2 (500 mg, 1.52 mmol), LiCl (142 mg, 3.34 mmol), $Pd_2dba_3$ (56 mg, 0.06 mmol), $Na_2CO_3$ (2.0 M solution in water, 2 mL), diethoxymethane (6 mL) were all charged to a flask and stirred vigorously. To this solution was added 2-naphthyl boronic acid (340 mg, 1.97 mmol). The reaction was then brought to reflux for two hours and then filtered through celite. The cake was washed with ether and all the organic solution was washed with concentrated ammonium hydroxide solution. The washed solvent was dried with potassium carbonate, filtered, and evaporated. The residue was charged to a column (1–4% $Et_3N$/EtOAc) and gave 240 mg (51%) of compound 50.

$R_f$ 0.48 (10% $Et_3N$/EtOAc). $^1$H-NMR ($CDCl_3$) δ 1.3–3.6 (m, 7H), 2.5 (s, 3H), 3.45 (s, 3H), 3.8–4.0 (m, 1H), 7.2–8.0 (m, 7H). Elemental analysis: calculated (0.5 $H_2O$) C, 77.24; H, 6.94; N, 4.50. found C, 77.27; H, 6.94; N, 4.48.

EXAMPLE 58

(1R)-2-Methoxycarbonyl-3-(2-naphthyl)-8-azabicyclo [3.2.1]-oct-2-ene (Compound 51, FIG. 10)

(1R)-N-Methyl-2-methoxycarbonyl-3-(2-naphthyl)-8-azabicyclo[3.2.1]-oct-2-ene 50 (100 mg, 0.33 mmol) was combined with ACE-Cl (0.25 mL) and the solution was heated to reflux for 5 h. The excess chloroformate was removed in vacuo and the residue was refluxed in methanol for 45 min. The methanol was removed in vacuo and the residue was dissolved in $CH_2Cl_2$ and shaken with $NaHCO_3$/$Na_2CO_3$ (pH=9). The aqueous layer was extracted $CH_2Cl_2$ (4×10 mL) and the combined organic extracts were dried ($Na_2SO_4$), filtered and concentrated. The residue was chromatographed (1–10% $Et_3N$/EtOAc). Like fractions were combined to yield compound 51 (27 mg, 28%).

$R_f$ 0.15 (10% $Et_3N$/EtOAc); $^1$H-NMR ($CDCl_3$) δ 1.6–2.5 (m, 5H), 2.7–3.1 (m, 1H), 3.45 (s, 3H), 3.8–3.9 (m, 1H), 4.2–4.35 (m, 1H), 7.1–8.0 (m, 7H).

EXAMPLE 59

N-[2-(3'-N'-Propyl-(1"R)-2"-methoxycarbonyl-3"-(2-naphthyl)-trop-2-ene))((2-((triphenylmethyl)thio) ethyl)amino)acetyl]-S-(triphenyl)-2-aminoethanethiol (Compound 52, FIG. 10)

To a solution of (1R)-2-methoxycarbonyl-3-(2-naphthyl)-8-azabicyclo[3.2.1]-oct-2-ene 51 (27 mg, 0.09 mmol) in dry $CH_3CN$ (10 mL) was added in succession N-[[[2-[2-(triphenylmethyl)thio]ethyl](N'-3'-chloropropyl)amino]acetyl]-S-(triphenyl-methyl)-2-aminoethanethiol (70 mg), KI (15 mg), and $K_2CO_3$ (127 mg). The resulting slurry was maintained at reflux overnight. Once the reaction was complete, the solution was allowed to cool to room temperature and partitioned between conc. aq. $NH_4OH$ and $CH_2Cl_2$. The layers were separated and the organic phase dried with $Na_2SO_4$. The solution was filtered and concentrated and the residue purified by flash chromatography (50–90% EtOAc/hexanes+3% $NH_4OH$) which gave 27 mg (29%) of 52.

$R_f$ 0.44 (1% NH40H in EtOAc); $^1$H-NMR ($CDCl_3$) δ 1.5–3.2 (m, 20H), 2.87 (s, 2H), 3.3–3.4 (m, 1H), 3.4 (s, 3H), 3.9–4.0 (m, 1H), 7.0–7.8 (m, 37H).

EXAMPLE 60

N-[(2-((3'-N'-Propyl-(1"R)-2"-methoxycarbonyl-3"-(2-naphthyl)-trop-2-ene) (2-mercaptoethyl)amino) acetyl)-2-aminoethane-thiolato]-rhenium (V) oxide (Compound 41, FIG. 10) (O-1185)

A solution of N-[2-(3'-N'-propyl-(1"R)-2"-methoxycarbonyl-3"-(2-naphthyl)trop-2-ene-))((2-((triphenylmethyl)thio) ethyl)amino)acetyl]-S-(triphenyl)-2-aminoethane-thiol 52 (27 mg, 0.027 mmol) in EtOH (10 mL) was heated to reflux. A solution of $SnCl_2$ (5.7 mg, 0.03 mmol) in 0.05 M HCl (1.0 mL) was added quickly followed immediately by $NaReO_4$ (8.2 mg, 0.03 mmol) in 0.05 M HCl (0.5 mL). The solution was refluxed for 10 h and was then applied to a chromatography column (5% $Et_3N$ in $Et_2O$). Like fractions were combined and concentrated to yield a mixture of the diastereomers (15 mg; 76%).

$R_f$ 0.15 (10% $Et_3N$ in EtOAc); IR (KBr) 967, cm$^{-1}$; Accurate mass calculated: 728.1599. found 728.1664. $^1$H-NMR ($CDCl_3$) δ 1.3–4.3 (m, 23H), 3.45 (s, 3H), 4.5–4.9 (m, 2H), 7.1–8.0 (m, 7H).

EXAMPLE 61

(1R)-N-Methyl-2β-methoxycarbonyl-3β-(2-naphthyl)-8-azabicyclo[3.2.1]octane (Compound 42, FIG. 10) (O-1229) and (1R)-N-Methyl-2β-methoxycarbonyl-3α-(2-naphthyl)-8-azabicyclo[3.2.1]octane (Compound 43, FIG. 10) (O-1228)

To (1R)-N-Methyl-2β-methoxycarbonyl-3-(2-naphthyl)-8-azabicyclo[3.2.1]-oct-2-ene 50 (510 mg, 1.66 mmol) in THF (15 mL) at −78° C. was added SmI$_2$ solution (0.1 M in THF, 116 mL, 11.6 mmol) dropwise. After 30 min at −78° C. MeOH (42 mL) was added and the resulting solution stirred at −78° C. for a further hour. The reaction was then quenched by adding TFA and water, the cold bath was also removed and the solution allowed to attain room temperature. The reaction was then made basic with NH$_4$OH and diluted with ether and then filtered through celite. The filter cake was washed with more ether and then all the organic phases were combined and washed with a sodium thiosulfate solution and then a brine solution. After drying with sodium sulfate the solution was filtered and concentrated and gave the crude products which were isolated by column chromatography (0–2% Et$_3$N in EtOAc). Compound 42 was isolated as a light yellow solid (110 mg, 22%).

Mp. 94–95° C. R$_f$ 0.28 (10% MeOH/CHCl$_3$); IR (KBr) 2900, 1750 cm$^{−1}$; $^1$H-NMR (CDCl$_3$) δ 1.5–2.3 (m, 5H), 2.25 (s, 3H), 2.7 (ddd, 1H), 2.9–3.3 (m, 2H), 3.45 (s, 3H), 3.3–3.4 (m, 1H), 4.5–4.6 (m, 1H), 7.3–7.5 (m, 3H), 7.7–7.9 (m, 4H). Elemental analysis: calculated (0.25 H$_2$O) C, 76.52; H, 7.55; N, 4.46. found C, 76.63; H, 7.57; N, 4.44.

Compound 43 was isolated as an off-white solid (113 mg, 23%).

M.p. 113–114° C., R$_f$ 0.56 (10% MeOH/CHCl$_3$); IR (KBr) 3000,1750 cm$^{−1}$; $^1$H NMR (CDCl$_3$) δ 1.4–1.6 (ddd, 1H), 1.4–1.8 (m, 3H), 2.0–2.4 (m, 2H), 2.3 (s, 3H), 2.4–2.7 (m, 1H), 2.65 (dd, 1H), 3.2–3.4 (m, 3H), 3.57 (s, 3H), 7.2–7.5 (m, 3H). Elemental analysis: calculated C, 77.64; H, 7.49; N, 4.53. found C, 77.48; H, 7.50; N, 4.45.

EXAMPLE 62

(1R)-2β-Methoxycarbonyl-3β-(2-naphthyl)-8-azabicyclo[3.2.1]-octane (Compound 44, FIG. 10)

(1R)-N-Methyl-2β-methoxycarbonyl-3β-(2-naphthyl)-8-azabicyclo[3.2.1]octane 42 (146 mg) was combined with ACE-Cl (5.5 mL) and the solution was heated to reflux for 5 h. The excess chloroformate was removed in vacuo and the residue was refluxed in methanol for 45 min. The methanol was removed in vacuo and the residue was dissolved in CH$_2$Cl$_2$ and shaken with NaHCO$_3$/Na$_2$CO$_3$ (pH=9). The aqueous layer was extracted CH$_2$Cl$_2$ and the combined organic extracts were dried (Na$_2$SO$_4$), filtered and concentrated. The residue was chromatographed (2% MeOH/EtOAc). Like fractions were combined to yield 44 (109 mg, 78%).

R$_f$ 0.27 (10% MeOH/EtOAc); $^1$H-NMR (CDCl$_3$) δ 1.5–2.4 (m, 5H), 2.68 (ddd, 1H),4.8–4.9 (m, 1H), 3.30 (s, 3H), 3.3–3.4 (m, 1H), 3.7–3.9 (m, 2H), 7.1–8.0 (m, 7H). Elemental analysis: calculated (0.25 H$_2$O) C, 76.10; H, 7.23; N, 4.67. found C, 75.98; H, 7.23; N, 4.60.

EXAMPLE 63

(1R)-2β-Methoxycarbonyl-3α-(2-naphthyl)-8-azabicyclo[3.2.1]-octane (Compound 45, FIG. 10)

(1R)-N-Methyl-2β-methoxycarbonyl-3α-(2-naphthyl)-8-azabicyclo[3.2.1]-octane, 43 (90 mg, 0.29 mmol) was combined with ACE-Cl (4 mL) and the solution was heated to reflux for 5 h. The excess chloroformate was removed in vacuo and the residue was refluxed in methanol for 45 min. The methanol was removed in vacuo and the residue was dissolved in CH$_2$Cl and shaken with NaHCO$_3$/Na$_2$CO$_3$ (pH=9). The aqueous layer was extracted CH$_2$Cl and the combined organic extracts were dried (Na$_2$SO$_4$), filtered and concentrated. The residue was chromatographed (2% MeOH/CHCl$_3$). Like fractions were combined to yield 45 (109 mg, 78%).

R$_f$ 0.29 (10% MeOH/CHCl$_3$).

EXAMPLE 64

N-[2-(3'-N'-Propyl-(1"R)-2"β-methoxycarbonyl-3"β-(2-naphthyl)-tropane))((2-((triphenylmethyl)thio)ethyl)amino)acetyl]-S-(triphenyl)-2-aminoethanethiol (Compound 46, FIG. 10)

To a solution of (1R)-2β-methoxycarbonyl-3β-(2-naphthyl)-8-azabicyclo[3.2.1]octane 44 (81 mg, 0.27 mmol) in dry CH$_3$CN (20 mL) was added in succession N-[[[2-[2-(triphenylmethyl)thio]ethyl](N'-3'-chloropropyl)amino]acetyl]-S-(triphenylmethyl)-2-aminoethanethiol (207 mg), KI (46 mg, 0.27 mmol), and K2CO$_3$ (378 mg). The resulting slurry was then maintained at reflux overnight. Once the reaction was complete, the solution was allowed to cool to room temperature and then partitioned between concentrated aqueous NH$_4$OH and CH$_2$Cl$_2$. The layers were separated and the organic phase dried with Na$_2$SO$_4$. The solution was filtered and concentrated and the residue purified by flash chromatography (0–90% EtOAc/hexanes+3% NH$_4$OH) which gave 150 mg (54%) of 46.

R$_f$ 0.36 (10% Et$_3$N in EtOAc); $^1$H-NMR (CDCl$_3$) δ 1.4–3.8 (m, 24H), 2.85 (s, 2H), 3.38 (s, 3H), 7.0–7.8 (m, 37H).

EXAMPLE 65

N-[2-(3'-N'-Propyl-(1"R)-2"β-methoxycarbonyl-3"α-(2-naphthyl)-tropane))((2-((triphenylmethyl)thio)ethyl)amino)acetyl]-S-(triphenyl)-2-aminoethanethiol (Compound 47, FIG. 10)

To a solution of (1R)-2β-methoxycarbonyl-3α-(2-naphthyl)-8-azabicyclo[3.2.1]octane 45 (17 mg, 0.06 mmol) in dry CH$_3$CN (10 mL) was added in uccession N-[[[2-[2-(triphenylmethyl)thio]ethyl](N'-3'-chloropropyl)amino]acetyl]-S-(triphenylmethyl)-2-aminoethanethiol (4.3 mg), KI (9.4 mg), and K2C03 (79 mg). The resulting slurry was then maintained at reflux overnight. Once the reaction was complete, the solution was allowed to cool to room temperature and then partitioned between concentrated aqueous NH$_4$OH and CH$_2$Cl$_2$. The layers were separated and the organic phase dried with Na$_2$SO$_4$. The solution was filtered and concentrated and the residue purified by flash chromatography (50–80% EtOAc/hexanes +3% NH$_4$OH) which gave 18 mg (31%) of 47.

R$_f$ 0.16 (50% EtOAc), 47% hexane, 3% NH$_4$OH).

EXAMPLE 66

N-[(2-((3'-N'-Propyl-(1"R)-2"β-methoxycarbonyl-3"β-(2-naphthyl)-tropane)(2-mercaptoethyl)amino)acetyl)-2-aminoethanethiolato]-rhenium (V) oxide (Compound 48, FIG. 10) (O-1339)

A solution of N-[2-(3'-N'-propyl-(1"R)-2"β-methoxycarbonyl-3"-(2-naphthyl)-trop-2-ene))((2-((triphenylmethyl)thio)ethyl)amino)acetyl]-S-(triphenyl)-2-amino-ethanethiol 46 (150 mg, 0.15 mmol) in EtOH (10 mL) was heated to reflux. A solution of SnCl$_2$ (31 mg, 0.16 mmol) in 0.05 M HCl (1.0 mL) was added quickly followed immediately by NaReO$_4$ (45 mg, 0.16 mmol) in 0.05 M HCl (0.5 mL). The solution was refluxed for 10 h and was then applied to a chromatography column (5% Et$_3$N in EtOAc). Like fractions were combined and concentrated to yield a mixture of the diastereomers (34 mg; 41%).

R$_f$ 0.39 (10% Et$_3$N in EtOAc); $^1$H-NMR (CDCl$_3$) δ 1.4–4.2 (m, 24H), 3.40,3.48 (2s, 3H), 4.4–4.7 (m, 1H), 8.25, 8.30 (2d, 1H), 7.2–8.0 (m, 7H). Elemental analysis: calculated (0.5 EtOAc) C, 46.97; H, 5.30; N, 5.39. found C, 46.91; H, 5.12; N, 5.19.

EXAMPLE 67

N-[(2-((3'-N'-Propyl-(1"R)-2'β-methoxycarbonyl-3"α-(2-naphthyl)-tropane)(2-mercaptoethyl)amino)acetyl)-2-aminoethanethiolato]-rhenium (V) oxide (Compound 49, FIG. 10)

A solution of N-[2-(3'-N'-propyl-(1"R)-2"β-methoxycarbonyl-3"α-(2-naphthyl)-trop-2-ene))((2-((triphenylmethyl)thio)ethyl)amino)acetyl]-S-(triphenyl)-2-amino-ethanethiol 47 (18 mg, 0.02 mmol) in EtOH (10 mL) was heated to reflux. A solution of SnCl$_2$ (5.3 mg) in 0.05 M HCl (1.0 mL) was added quickly followed immediately by NaReO$_4$ (3.7 mg) in 0.05 M HCl (0.5 mL). The solution was refluxed for 10 h and was then applied to a chromatography column (5% Et$_3$N in Et$_2$O). Like fractions were combined and concentrated to yield a mixture of the diastereomers (40%).

R$_f$ 0.46 (5% Et$_3$N in EtOAc); $^1$H-NMR (CDCl$_3$) δ 1.4–1.8 (m, 24H), 1.8–2.0 (m, 2H), 2.02–2.20 (m, 1H), 2.3–2.5 (m, 3H), 2.69, 2.71 (2s, 3H), 2.9–3.0 (2dd, 1H), 3.1–3.4 (m, 3H), 3.4–3.6 (m, 1H), 3.5,3.55 (2s, 3H), 3.6–3.8 (2ddd, 1H), 3.9–4.2 (m, 3H), 4.5–4.7 (m, 1H), 4.75, 4.98 (2d, 1H), 7.32 (d, 1H), 7.3–7.5 (m, 2H), 7.64 (s, 1H), 7.7–7.8 (m, 3H).

EXAMPLES 68–80

Tests were conducted to determine the binding affinity and selectivity of certain compounds for the dopamine transporter. The results are tabulated below.

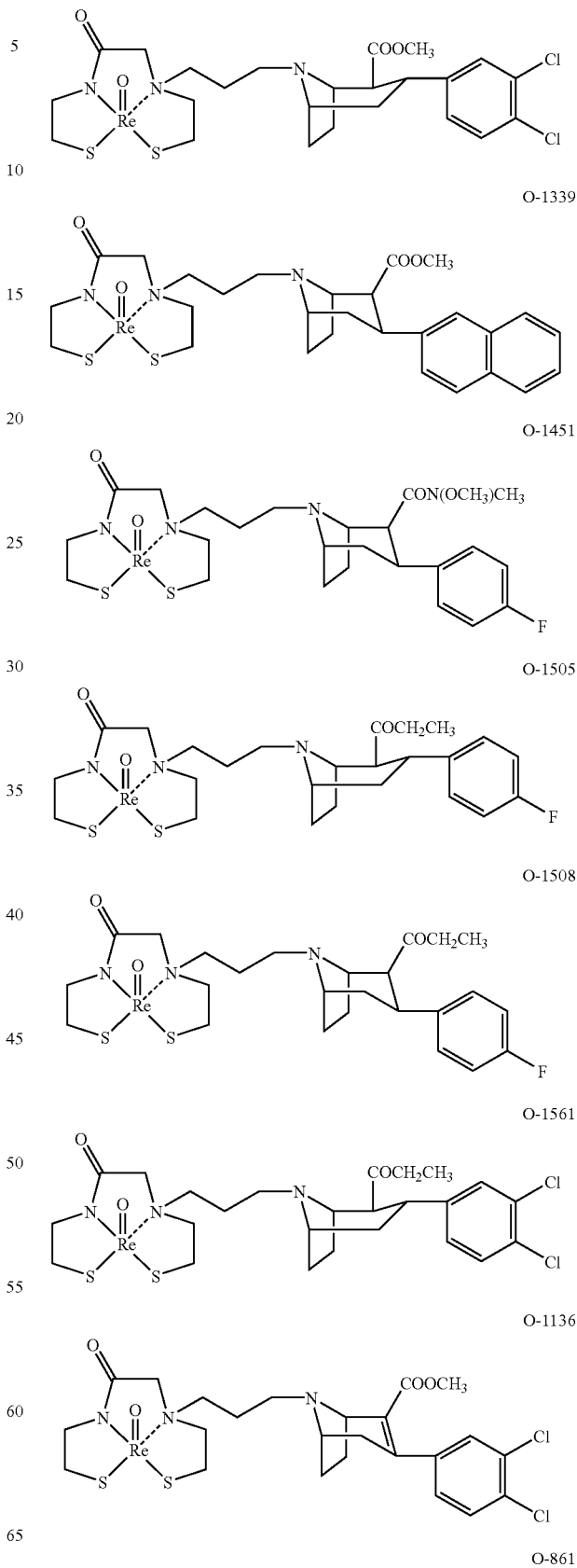

| Example | Compound | IC50 DAT | IC50 SERT | DAT/ SERT |
|---|---|---|---|---|
| 68 | O-1136 | 60 | 1693 | 28 |
| 69 | O-861 | 2.9 | 80 | 28 |
| 70 | O-863 | 40 | — | — |
| 71 | O-927 | 5.0 | 200 | 40 |
| 72 | O-928 | 3.0 | 30 | 10 |
| 73 | O-1185 | 63 | 960 | 15 |
| 74 | O-1186 | 3.8 | 1300 | 340 |
| 75 | O-1196 | 10 | 640 | 64 |
| 76 | O-1339 | 3.6 | 59 | 16 |
| 77 | O-1451 | 40 | 3260 | 80 |
| 78 | O-1505 | 2.0 | 497 | 249 |
| 79 | O-1508 | 5.9 | 200 | 34 |
| 80 | O-1561 | 5.3 | 337 | 63 |

EXAMPLES 81–91

$^{99m}$Tc Labeling

The following compounds were prepared by identical methods described below.

81   N-[(2-((3'-N'-Propyl-(1"R)-2"β-methoxycarbonyl-3"α-(3,4-dichlorophenyl)-tropane)-(2-mercaptoethyl)amino)acetyl)-2-aminoethanethiolato]-technetium (V) oxide (Compound 37 (R=3,4-Cl$_2$), FIG. 8) (O-1196)

82   N-[(2-((3'-N'-Propyl-(1"R)-2"β-1-propanoyl-3"α-(3,4-fluorophenyl)-tropane)-(2-mercaptoethyl)amino)acetyl)-2-aminoethanethiolato]technetium (V) oxide (Compound 19 (R=4-F), FIG. 4)

83   N-[(2-((3'-N'-Propyl-(1"R)-2"β-1-propanoyl-3"α-(3,4-dichlorophenyl)-tropane)(2-mercaptoethyl)amino)acetyl)-2-aminoethanethiolato]-technetium (V) oxide (Compound 19 (R=3,4-Cl$_2$), FIG. 4)

84   N-[(2-((3'-N'-Propyl-(1"R)-2"β-methoxymethylcarbamoyl-3"α-(4-fluorophenyl)-tropane)(2-mercaptoethyl)amino)acetyl)-2-aminoethanethiolato]-technetium (V) oxide (Compound 22 (R=4-F), FIG. 5) (O-1451)

85   (RS)-N-[2-((3'-N'-Propyl-(1"R-2"β-carbomethoxy-3"β-(4-fluorophenyl)-tropane))(2-mercaptoethyl)amino)acetyl)-2-aminoethanethiolato]technetium (V) oxide (Compound 34 (R=4-F), FIG. 8)

86   (RS)-N-[2-((3'-N'-Propyl-(1"R-2"β-carbomethoxy-3"β-(3,4-dichlorophenyl)-tropane))(2-mercaptoethyl)amino)acetyl)-2-aminoethanethiolato]-technetium (V) oxide (Compound 34 (R=3,4-Cl$_2$), FIG. 8)

87   N-[(2-((3'-N'-Propyl-(1"R)-2"-carbomethoxy-3"-(4-fluorophenyl)-tropene)(2-mercaptoethyl)amino)acetyl)-2-aminoethanethiolato]-technetium (V) oxide (Compound 31 (R=4-F), FIG. 7)

88   N-[(2-((3'-N'-Propyl-(1"R)-2"-methoxycarbonyl-3"-(3,4-dichlorophenyl)-tropene)(2-mercaptoethyl)amino)acetyl)-2-aminoethanethiolato]-technetium (V) oxide (Compound 31 (R=3,4-Cl$_2$), FIG. 7)

89   N-[(2-((3'-N'-Propyl-(1"R)-2"β-methoxycarbonyl-3"α-(4-fluorophenyl)-tropane)(2-mercaptoethyl)amino)acetyl)-2-aminoethane-thiolato]-technetium (V) oxide (Compound 37 (R=4-F), FIG. 8)

90   N-[(2-((3'-N'-Propyl-(1"R)-3"β-(4-fluorophenyl)tropane-2"β-1-propanoyl)-(2-mercaptoethyl)amino)acetyl)-2-aminoethanethiolato]technetium (V) oxide (Compound 11 (R=4-F), FIG. 3)

91 N-[(2-((3'-N'-Propyl-(1"R)-2"β-1-propanoyl-3"β-(3,4-dichlorophenyl)-tropane)(2-mercaptoethyl)amino)acetyl)-2-aminoethanethiolato]-technetium (V) oxide (Compound 11 (R=3,4-Cl$_2$), FIG. 3)

Deprotection of Tropane Analog for Radiolabeling:

The following is a description of the procedures that were employed:

Twenty microliter aliquots of TFA, CH$_2$Cl2, and (C$_2$H$_5$)$_3$SiH were added to 5.0 mg of each trityl protected precursor to cleave the thiol protecting group. After a 20 min. incubation, 200 μL of 1.0 M HCl/Ether was added to protonate the thiols. The solvent was evaporated off, followed by successive washes with hexanes to remove the trityl groups. The deprotected compound was then dissolved in DMSO to produce a stock solution at a concentration of 1 mg/mL.

Radiolabeling the Tropane Analog:

Approximately 200 mCi of sodium $^{99m}$Tc pertechnetate was added to a Glucoheptonate kit (Du Pont Pharmaceuticals, Billerica, Mass.) and allowed to incubate at room temperature for 15 min. 150 mCi of the resulting $^{99m}$Tc-Glucoheptonate was added to an equal volume of 50 mM Acetate Buffer, pH 5.2 (approximately 2 mL) and 50 µL of deprotected precursor stock solution (1 mg/mL in DMSO, 50 µg). This solution was incubated at room temperature for 20 min. The course of the radiolabeling was monitored with a Rainin HPLC system using a reverse phase Vydac C8 column (4.6×250 mm 5µm). The column was eluted with a 0.1M ammonium acetate/acetonitrile mobile phase; 1.5 mL/min. flow rate, and a gradient of 5–100% acetonitrile over 15 minutes. Radioactive detection is achieved with a Frisk-Tech Rate meter (Bicron Corp.). The final radiolabeled product was purified using a C18 Sep-Pak (Waters Inc.) eluted with ethanol. For all compounds, labeling yields and radiochemical purities were greater than 85% and 98%, respectively. Each product was diluted with sterile saline to yield a <10% ethanol solution followed by filtration through a 0.22 µm filter prior to injection. Typical HPLC chromatograms are shown in FIGS. 11–14.

Summary of Analytical Results, HPLC:

With the above methodology, it was observed that the retention times were dependent upon two features of the analog, i.e., the conformation and the substituents. As expected the dichloro-analogs eluted later than the monofluorinated compounds and the boat conformers eluted later than the respective chair compounds. Retention times for four specific $^{99m}$Tc labeled compounds are tabulated below. The reproducibility was ±0.1 min.

| Example No. | Compound | Retention Time(min.) |
|---|---|---|
| Example 82 | O-1505T | 16.6 |
| Example 90 | O-1508T | 15.2 |
| Example 83 | O-1561T | 17.1 |
| Example 91 | O-1506T | 16.1 |

Animal Model of Parkinson's Disease:

The neurotoxin MPTP (N-methyl-1,2,3,6-tetrahydropyridine), when administered to monkeys, produces a spectrum of motor, cognitive, biochemical and morphological changes that is not replicated in rodents. MPTP-treated monkeys develop neurological deficits (resting tremor, rigidity, akinesia, postural abnormalities), morphological changes (cell loss in the substantia nigra, ventral tegmental area, retrorubal fields) and biochemical changes (severe depletion of DA and decreases in norepinephrine and serotonin) that closely, parallel idiopathic PD and post-encephalitic Parkinsonism.

Two monkeys were treated with MPTP; 3–5 doses of 0.6 mg/kg administered over 10 days. Treatment was performed under ketamine anesthesia (15 mg/kg). This dose of MPTP, has previously been used to produce Parkinsonism within 2–3 weeks and depletion of $^3$H or $^{11}$C CFT binding sites by one month. Animals treated in this manner were expected to show an inverse relationship between SPECT tracer binding and motor dysfunction. The marked depletion of DA terminals produced by this treatment should provide definitive evidence of the selectivity and sensitivity of the SPECT tracers to detect full depletion of the nerve terminals.

SPECT Imaging

All SPECT images were acquired with a MultiSPECT 2 gamma camera (Siemens, Hoffman Estates, Ill.) equipped with fan-beam collimators and peaked to the 140 KeV photopeak of $^{99m}$Tc (15% window). This camera has intrinsic resolution of 4.6 mm (FWHM), and a sensitivity of ~240 cps/mCi. Images were acquired over 360° (60 projections/head, 128×128 matrix) in the continuous mode. Image reconstruction was performed using a conventional filtered back-projection algorithm to an in-plane resolution of 10 mm FWHM and attenuation correction via the Chang method.

Rhesus monkeys weighing approximately 7 kg were anesthetized with ketamine/xylazine (15.0 and 1.5 mg/kg) and positioned prone on the imaging bed of the SPECT camera. Before the start of imaging, a venous catheter was inserted in a peripheral vein for radiopharmaceutical administration. The heads of the animals were immobilized with a custom fabricated head holder. Approximately 20–25 mCi of $^{99m}$Tc labeled O-1505T, O-1508T, O-1561T or O-1560T was injected intravenously over 60 seconds. Dynamic SPECT imaging was initiated at the end of the infusion and consisted of 2 min. acquisitions during the first hour and 5 min. acquisitions thereafter.

Selectiuity of For DAT Sites in the Monkey Brain

For this study, a monkey was positioned supine on the imaging table of the MultiSPECT 2 gamma camera and injected with ~20 mCi of $^{99m}$Tc O-1560T as described above. At approximately 20 min. after radiopharmaceutical administration, the animal was injected with CFT (1.0 mg/kg) and imaging was continued for an additional 70 min.

Image Analysis

SPECT slices with greatest striatal activity or in which the occipital cortex was well visualized were summed and regions of interest (ROI's) were constructed. In the striatal planes, ROI's were placed on the right and left striatum (caudate+putamen). Radioactivity in the right and left striatum were averaged. ROI radioactivities (cpm/cc) were decay corrected to the time of injection. The difference between striatal and occipital cortex activity (specific binding) was calculated for each image and was plotted as a function of time. Corrections for scattered fraction and partial volume effects were not performed.

Radiation Dosimetry

Groups of male Sprague-Dawley rats were in injected with ~10 mCi of $^{99m}$Tc labeled O-1505T and O-1561T. At time intervals between 5 min. and 24 hrs after injection, groups of 6 animals injected with each radiopharmaceutical were sacrificed and biodistribution was measured. Samples of blood, heart, lung, liver, spleen, kidney, adrenal, stomach, GI tract, testes, bone, bone marrow and skeletal muscle were weighed and radioactivity was measured with a well type gamma counter (LKB model # 1282, Wallac Oy, Finland). To correct for radioactive decay and permit calculation of the concentration of radioactivity in each organ as a fraction of the administered dose, aliquots of the injected doses were counted simultaneously. The results were expressed as percent injected dose per gram (%I.D./g) and radiation dosimetry was estimated by the MIRdose method.

Results

SPECT Imaging with 99mTc Labeled O-1505T, O-1508T, O-1561 T and O-1560T

In the images acquired early after injection of $^{99m}$Tc O-1505T and $^{99m}$Tc O-1561T, diffuse accumulation of radioactivity was observed throughout the brain. Over the first several minutes after injection, accumulation of tracer in the striatum intensified and the level of radioactivity in all other structures decreased. By 30 minutes after injection there was excellent contrast between striatum and the rest of the brain. Trans-axial, sagittal and coronal images of monkey brains were acquired between 30 and 50 minutes after injection of $^{99m}$Tc labeled O-1505T, O-1508T, O-1561T and O-1560T. From these data, it is clear that the images acquired after injection of $^{99m}$Tc O-1505T and $^{99m}$Tc O-1561T (boat forms of the monofluoro and dichloro compounds, respectively)

display high concentrations of radiopharmaceutical in the striatum with minimal accumulation in other areas of the brain. In particular, lack of accumulation in the thalamus, hypothalamus or midbrain, regions that are rich in 5-HT transporters, supports the specificity of this tracer for DAT sites. Region of interest analysis yielded striatal to occipital cortex ratios of approximately ~2.5 to 1. In this experiment, images acquired after injection of $^{99m}$Tc O-1508T and $^{99m}$Tc O-1560T (chair forms of the monofluoro and dichloro compounds, respectively) differed with O-1508T failing to demonstrate significant accumulation of radioactivity in striatum or elsewhere in the brain while O-1560T provided results more like O-1505T and O-1561T.

SPECT of MPTP Treated Monkeys (Mid-striatal) trans-axial, sagittal and coronal SPECT images of the brain of a rhesus monkey injected with $^{99m}$Tc O-1505T were obtained one month after MPTP treatment. Compared with normal animals, after MPTP treatment, the level of accumulation decreased markedly and the striatum could not be differentiated from surrounding structures.

Selectivity of $^{99m}$Tc O-1505T for DAT Sites in Monkey Brain

SPECT images of monkey brain showed significant accumulation of $^{99m}$Tc O-1505T in the striatum. In the early images there was diffuse accumulation of radioactivity throughout the brain. Over the first several minutes after injection, accumulation of tracer in the striatum intensified and the level of radioactivity in all other structures decreased. By 30 minutes after injection there was excellent contrast between striatum and the rest of the brain. After injection of a receptor saturating dose of unlabeled CFT, striatal accumulation of radioactivity decreased and by 60 minutes after injection, there was no evidence of focal accumulation in the striatum.

Radiation Dosimetry

The biodistribution studies demonstrated that both $^{99m}$Tc O-1505T and $^{99m}$Tc O-1561 cleared rapidly from all tissues of the rat. For $^{99m}$Tc O-1505T, MIRdose calculations revealed urinary bladder to be the target organ with a dose of 0.29 rem/mCi. Total body effective dose was estimated at 0.037 rem/mCi

SUMMARY

These results demonstrate that $^{99m}$Tc labeled O-1505T and O-1561T are excellent SPECT ligands for DAT sites. These radiopharmaceuticals combine the the following important characteristics for obtaining useful diagnostic images: (1) high striatal to occipital cortex ratios; (2) high selectivity for DAT vs. 5-HT transporter (SET) sites; (3) convenient preparation at high specific activity and radiochemical purity; (4) favorable radiation dosimetry and (5) striatal localization rate that is well matched to the physical t½ of $^{99m}$Tc.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

We claim:
1. A compound having the following structural formula:

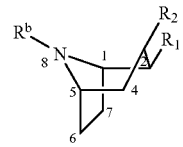

wherein
R$_1$ is α or β and COR$^a$;
R$_2$ is α and is selected from C$_6$H$_4$X, C$_6$H$_3$XY, C$_{10}$H$_7$X, and C$_{10}$H$_6$XY;
R$^a$ is C$_1$–C$_5$ alkyl;
X and Y are independently selected from R$^a$, H, Br, Cl, I, F, OH, and OCH$_3$;
wherein the compound is in the 1R or 1S configuration; and
Rb is either H or CH$_3$.

2. The compound according to claim 1, wherein R$^a$ is methyl.
3. The compound according to claim 1, wherein R$^a$ is ethyl.
4. The compound according to claim 1, wherein R$^a$ is propyl.
5. The compound according to claim 1, wherein R$^a$ is isopropyl.
6. The compound according to claim 1 selected from the group consisting of:
   a. 2β-(1-Propanoyl)-3β-(4-fluorophenyl)tropane;
   b. 2β-(1-Propanoyl)-3β-(3,4-dichlorophenyl)tropane;
   c. 2β-(1-Propanoyl)-3β-(4-fluorophenyl)nortropane; and
   d. 2β-(1-Propanoyl)-3β-(3,4-dichlorophenyl)nortropane.

7. A compound having the following structural formula:

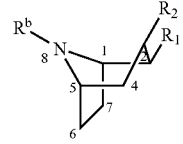

wherein R$_1$ is β and COR$^a$;
R$_2$ is α and is selected from C$_6$H$_4$X, C$_6$H$_3$XY, C$_{10}$H$_7$X, and C$_{10}$H$_6$XY;
R$^a$ is C$_1$–C$_5$ alkyl;
X and Y are independently selected from R$^a$, H, Br, Cl, I, F, OH, and OCH$_3$;
wherein the compound is in the 1R or 1S configuration; and
R$^b$ is either H or CH$_3$.

8. The compound of claim 7, wherein R$^a$ is ethyl.
9. The compound of claim 8, wherein R$_2$ is C$_6$H$_4$X.
10. The compound of claim 9, wherein X is F.
11. 2β-(1-Propanoyl)-3α-(4-fluorophenyl)-tropane.
12. (1R)-2β-(1-Propanoyl)-3α-(4-fluorophenyl)-tropane.

* * * * *